(12) United States Patent
Horton et al.

(10) Patent No.: US 8,426,396 B2
(45) Date of Patent: Apr. 23, 2013

(54) TREATMENT FOR ACHONDROPLASIA

(75) Inventors: William A. Horton, Portland, OR (US); Melanie B. Laederich, Portland, OR (US)

(73) Assignee: Shriners Hospitals for Children, Tampa, FL (US)

( * ) Notice: Subject to any disclaimer, the term of this patent is extended or adjusted under 35 U.S.C. 154(b) by 461 days.

(21) Appl. No.: 12/350,940

(22) Filed: Jan. 8, 2009

(65) Prior Publication Data

US 2009/0192133 A1 Jul. 30, 2009

Related U.S. Application Data

(60) Provisional application No. 61/019,759, filed on Jan. 8, 2008.

(51) Int. Cl.
*A61K 31/395* (2006.01)
*A61K 31/52* (2006.01)
*A61K 31/4196* (2006.01)

(52) U.S. Cl.
USPC .................. 514/183; 514/263.1; 514/383

(58) Field of Classification Search .................. None
See application file for complete search history.

(56) References Cited

U.S. PATENT DOCUMENTS

| | | | |
|---|---|---|---|
| 7,259,156 B2 | 8/2007 | Santi et al. | |
| 7,947,670 B2 * | 5/2011 | Austad et al. | 514/183 |
| 2010/0249118 A1 * | 9/2010 | Ibrahim et al. | 514/228.2 |

FOREIGN PATENT DOCUMENTS

WO WO 2007/129062 * 11/2007

OTHER PUBLICATIONS

Dodé et al. Loss-of-function mutations in FGFR1 cause autosomal dominant Kallmann syndrome. Nat Genet. Apr. 2003;33(4):463-5. Epub Mar. 10, 2003.*
Gartside et al. Loss-of-function fibroblast growth factor receptor-2 mutations in melanoma. Mol Cancer Res. Jan. 2009;7(1):41-54.*
Price et al. The heat shock protein 90 inhibitor, 17-allylamino-17-demethoxygeldanamycin, enhances osteoclast formation and potentiates bone metastasis of a human breast cancer cell line. Cancer Res. Jun. 1, 2005;65(11):4929-38.*
Shams et al. Lacrimo-auriculo-dento-digital syndrome is caused by reduced activity of the fibroblast growth factor 10 (FGF10)-FGF receptor 2 signaling pathway. Mol Cell Biol. Oct. 2007;27(19):6903-12. Epub Aug. 6, 2007.*
Snyder-Warwick et al. Analysis of a gain-of-function FGFR2 Crouzon mutation provides evidence of loss of function activity in the etiology of cleft palate. Proc Natl Acad Sci U S A. Feb. 9, 2010;107(6):2515-20. Epub Feb. 1, 2010.*
Toydemir et al. A novel mutation in FGFR3 causes camptodactyly, tall stature, and hearing loss (CATSHL) syndrome. Am J Hum Genet. Nov. 2006;79(5):935-41. Epub Sep. 26, 2006.*
Deng et al. Fibroblast growth factor receptor 3 is a negative regulator of bone growth. Cell. Mar. 22, 1996;84(6):911-21.*
Terry et al. Hsp90 inhibitor 17-allylamino-17-demethoxygeldanamycin prevents synovial sarcoma proliferation via apoptosis in in vitro models. Clin Cancer Res. Aug. 1, 2005;11(15):5631-8.*
U.S. Appl. No. 61/019,759, filed Jan. 8, 2008, Horton et al.
Citri et al., "Drug-induced ubiquitylation and degradation of ErbB receptor tyrosine kinases: implications for cancer therapy", EMBO. J. 21:2407-2417 (2002).
Citri et al., "Hsp90 restrains ErbB-2/HER2 signalling by limiting heterodimer formation", EMBO Rep. 5(12):1165-1170 (2004).
Germano et al., "Geldanamycins trigger a novel Ron degradative pathway, hampering oncogenic signaling", J. Biol. Chem. 281:21710-9 (2006).
Horton et al., "Achondroplasia", Lancet 370(9582):162-172 (2007).
Lotz et al., "Aha1 binds to the middle domain of Hsp90, contributes to client protein activation, and stimulates the ATPase activity of the molecular chaperone", J. Biol. Chem. 278(19):17228-17235 (2003).
Ornitz and Marie, "FGF signaling pathways in endochondral and intramembranous bone development and human genetic disease", Genes & Dev. 16:1446-1465 (2002).
Pearl and Prodromou, "Structure and mechanism of the Hsp90 molecular chaperone machinery", Annu. Rev. Biochem. 75:271-294 (2006).
Laederich et al., "Fibroblast Growth Factor Receptor 3 (FGFR3) Is a Strong Heat Shock Protein 90 (Hsp90) Client," *Journal of Biological Chemistry*, vol. 286, No. 22, pp. 19597-19604, Jun. 3, 2011.

* cited by examiner

*Primary Examiner* — David Romeo
(74) *Attorney, Agent, or Firm* — Fish & Richardson P.C.

(57) ABSTRACT

The present application provides, inter alia, methods of treating disorders mediated by FGFRs and methods of screening for Hsp90 inhibitor compounds.

26 Claims, 24 Drawing Sheets

FIG. 2A

SEQ ID NO: 1 - FGFR1 cDNA sequence (Accession No: NM_023110)

```
   1 agatgcaggg gcgcaaacgc caaaggagac caggctgtag gaagagaagg gcagagcgcc
  61 ggacagctcg gcccgctccc cgtcctttgg ggccgcggct ggggaactac aaggcccagc
 121 aggcagctgc aggggggcgga ggcggaggag ggaccagcgc gggtgggagt gagagagcga
 181 gccctcgcgc cccgccggcg catagcgctc ggagcgctct tgcggccaca ggcgcggcgt
 241 cctcggcggc gggcggcagc tagcgggagc cgggacgccg gtgcagccgc agcgcgcgga
 301 ggaacccggg tgtgccggga gctgggcggc cacgtccgga cgggaccgag accccctcgta
 361 gcgcattgcg gcgacctcgc cttccccggc cgcgagcgcg ccgctgcttg aaaagccgcg
 421 gaacccaagg acttttctcc ggtccgagct cggggcgccc cgcagggcgc acggtacccg
 481 tgctgcagtc gggcacgccg cggcgccggg gcctccgcag ggcgatggag cccggtctgc
 541 aaggaaagtg aggcgccgcc gctgcgttct ggaggagggg ggcacaaggt ctggagaccc
 601 cgggtggcgg acgggagccc tccccccgcc ccgcctccgg ggcaccagct ccggctccat
 661 tgttcccgcc cgggctggag gcgccgagca ccgagcgccg ccgggagtcg agcgccggcc
 721 gcggagctct tgcgaccccg ccaggacccg aacagagccc gggggcggcg ggccggagcc
 781 ggggacgcgg gcacacgccc gctcgcacaa gccacggcgg actctcccga ggcggaacct
 841 ccacgccgag cgagggtcag tttgaaaagg aggatcgagc tcactgtgga gtatccatgg
 901 agatgtggag ccttgtcacc aacctctaac tgcagaactg ggatgtggag ctggaagtgc
 961 ctcctcttct gggctgtgct ggtcacagcc acactctgca ccgctaggcc gtccccgacc
1021 ttgcctgaac aagcccagcc ctggggagcc cctgtggaag tggagtcctt cctggtccac
1081 cccggtgacc tgctgcagct tcgctgtcgg ctgcgggacg atgtgcagag catcaactgg
1141 ctgcgggacg gggtgcagct ggcggaaagc aaccgcaccc gcatcacagg ggaggaggtg
1201 gaggtgcagg actccgtgcc cgcagactcc ggcctctatg cttgcgtaac cagcagcccc
1261 tcgggcagtg acaccaccta cttctccgtc aatgtttcag atgctctccc ctcctcggag
1321 gatgatgatg atgatgatga ctcctcttca gaggagaaag aaacagataa caccaaacca
1381 aaccgtatgc ccgtagctcc atattggaca tccccagaaa agatggaaaa gaaattgcat
1441 gcagtgccgg ctgccaagac agtgaagttc aaatgccctt ccagtgggac cccaaacccc
1501 acactgcgct ggttgaaaaa tggcaaagaa ttcaaacctg accacagaat tggaggctac
1561 aaggtccgtt atgccacctg gagcatcata atggactctg tggtgccctc tgacaagggc
1621 aactacacct gcattgtgga gaatgagtac ggcagcatca accacacata ccagctggat
1681 gtcgtggagc ggtcccctca ccggcccatc ctgcaagcag ggttgcccgc aacaaaaaca
1741 gtggccctgg gtagcaacgt ggagttcatg tgtaaggtgt acagtgaccc gcagccgcac
1801 atccagtggc taaagcacat cgaggtgaat gggagcaaga ttggcccaga caacctgcct
1861 tatgtccaga tcttgaagac tgctggagtt aataccaccg acaaagagat ggaggtgctt
1921 cacttaagaa atgtctcctt tgaggacgca ggggagtata cgtgcttggc gggtaactct
1981 atcggactct cccatcactc tgcatggttg accgttctgg aagccctgga agagaggccg
2041 gcagtgatga cctcgcccct gtacctggag atcatcatct attgcacagg ggccttcctc
2101 atctcctgca tggtggggtc ggtcatcgtc tacaagatga agagtggtac caagaagagt
2161 gacttccaca gccagatggc tgtgcacaag ctggccaaga gcatccctct gcgcagacag
2221 gtaacagtgt ctgctgactc cagtgcatcc atgaactctg ggttcttct ggttcggcca
2281 tcacggctct cctccagtgg gactcccatg ctagcagggg tctctgagta tgagcttccc
2341 gaagaccctc gctgggagct gcctcgggac agactggtct taggcaaacc cctgggagag
```

FIG. 2A (cont'd)

```
2401 ggctgctttg ggcaggtggt gttggcagag gctatcgggc tggacaagga caaacccaac
2461 cgtgtgacca aagtggctgt gaagatgttg aagtcggacg caacagagaa agacttgtca
2521 gacctgatct cagaaatgga gatgatgaag atgatcggga agcataagaa tatcatcaac
2581 ctgctggggg cctgcacgca ggatggtccc ttgtatgtca tcgtggagta tgcctccaag
2641 ggcaacctgc gggagtacct gcaggcccgg aggcccccag ggctggaata ctgctacaac
2701 cccagccaca acccagagga gcagctctcc tccaaggacc tggtgtcctg cgcctaccag
2761 gtggcccgag gcatggagta tctggcctcc aagaagtgca tacaccgaga cctggcagcc
2821 aggaatgtcc tggtgacaga ggacaatgtg atgaagatag cagactttgg cctcgcacgg
2881 gacattcacc acatcgacta ctataaaaag acaaccaacg ccgactgcc tgtgaagtgg
2941 atggcacccg aggcattatt tgaccggatc tacacccacc agagtgatgt gtggtctttc
3001 ggggtgctcc tgtgggagat cttcactctg ggcggctccc catacccgg tgtgcctgtg
3061 gaggaacttt tcaagctgct gaaggagggt caccgcatgg acaagcccag taactgcacc
3121 aacgagctgt acatgatgat gcgggactgc tggcatgcag tgccctcaca gagacccacc
3181 ttcaagcagc tggtggaaga cctggaccgc atcgtggcct tgacctccaa ccaggagtac
3241 ctggacctgt ccatgccct ggaccagtac tcccccagct ttcccgacac ccggagctct
3301 acgtgctcct caggggagga ttccgtcttc tctcatgagc cgctgcccga ggagccctgc
3361 ctgccccgac acccagccca gcttgccaat ggcggactca acgccgctg actgccaccc
3421 acacgccctc cccagactcc accgtcagct gtaaccctca cccacagccc tgctgggcc
3481 caccacctgt ccgtccctgt cccctttcct gctggcagga gccggctgcc taccaggggc
3541 cttcctgtgt ggcctgcctt caccccactc agctcacctc tccctccacc tcctctccac
3601 ctgctggtga gaggtgcaaa gaggcagatc tttgctgcca gccacttcat ccctcccag
3661 atgttggacc aacacccctc cctgccacca ggcactgcct ggagggcagg gagtgggagc
3721 caatgaacag gcatgcaagt gagagcttcc tgagctttct cctgtcggtt tggtctgttt
3781 tgccttcacc cataagcccc tcgcactctg gtggcaggtg ccttgtcctc agggctacag
3841 cagtagggag gtcagtgctt cgtgcctcga ttgaaggtga cctctgcccc agataggtgg
3901 tgccagtggc ttattaattc cgatactagt ttgctttgct gaccaaatgc ctggtaccag
3961 aggatggtga ggcgaaggcc aggttggggg cagtgttgtg gccctggggc ccagccccaa
4021 actgggggct ctgtatatag ctatgaagaa aacacaaagt gtataaatct gagtatatat
4081 ttacatgtct tttaaaagg gtcgttacca gagatttacc catcgggtaa gatgctcctg
4141 gtggctggga ggcatcagtt gctatatatt aaaacaaaa aagaaaaaa aggaaaatgt
4201 ttttaaaaag gtcatatatt tttgctact tttgctgttt tatttttta aattatgttc
4261 taaacctatt tcagtttag gtccctcaat aaaaattgct gctgcttcat ttatctatgg
4321 gctgtatgaa aagggtggga atgtccactg gaaagaaggg acacccacgg gccctgggc
4381 taggtctgtc ccgagggcac cgcatgctcc cggcgcaggt tccttgtaac ctcttcttcc
4441 taggtcctgc acccagacct cacgacgcac ctcctgcctc tccgctgctt ttggaaagtc
4501 agaaaaagaa gatgtctgct tcgagggcag gaacccatc catgcagtag aggcgctggg
4561 cagagagtca aggcccagca gccatcgacc atggatggtt cctccaagg aaaccggtgg
4621 ggttgggctg ggaggggggc acctacctag gaatagccac ggggtagagc tacagtgatt
4681 aagaggaaag caagggcgcg gttgctcacg cctgtaatcc cagcactttg ggacaccgag
4741 gtgggcagat cacttcaggt caggagtttg agaccagcct ggccaactta gtgaaacccc
4801 atctctacta aaaatgcaaa aattatccag gcatggtggc acacgcctgt aatcccagct
4861 ccacaggagg ctgaggcaga atcccttgaa gctgggaggc ggaggttgca gtgagccgag
4921 attgcgccat tgcactccag cctgggcaac agagaaaaca aaaaggaaaa caaatgatga
4981 aggtctgcag aaactgaaac ccagacatgt gtctgccccc tctatgtggg catggttttg
```

FIG. 2A (cont'd)

```
5041 ccagtgcttc taagtgcagg agaacatgtc acctgaggct agttttgcat tcaggtccct
5101 ggcttcgttt cttgttggta tgcctcccca gatcgtcctt cctgtatcca tgtgaccaga
5161 ctgtatttgt tgggactgtc gcagatcttg gcttcttaca gttcttcctg tccaaactcc
5221 atcctgtccc tcaggaacgg ggggaaaatt ctccgaatgt ttttggtttt ttggctgctt
5281 ggaatttact tctgccacct gctggtcatc actgtcctca ctaagtggat tctggctccc
5341 ccgtacctca tggctcaaac taccactcct cagtcgctat attaaagctt atattttgct
5401 ggattactgc taaatacaaa agaaagttca atatgttttc atttctgtag ggaaaatggg
5461 attgctgctt taaatttctg agctagggat tttttggcag ctgcagtgtt ggcgactatt
5521 gtaaaattct ctttgtttct ctctgtaaat agcacctgct aacattacaa tttgtattta
5581 tgtttaaaga aggcatcatt tggtgaacag aactaggaaa tgaatttta gctcttaaaa
5641 gcatttgctt tgagaccgca caggagtgtc tttccttgta aaacagtgat gataatttct
5701 gccttggccc taccttgaag caatgttgtg tgaagggatg aagaatctaa aagtcttcat
5761 aagtccttgg gagaggtgct agaaaaatat aaggcactat cataattaca gtgatgtcct
5821 tgctgttact actcaaatca cccacaaatt tccccaaaga ctgcgctagc tgtcaaataa
5881 aagacagtga aattgacctg aaaaaaaaaa aaaaaaa
```

FIG. 2B

SEQ ID NO: 2 - FGFR1 amino acid sequence (Accession No. NP_075598)

```
1   mwswkcllfw avlvtatlct arpsptlpeq aqpwgapvev esflvhpgdl lqlrcrlrdd
61  vqsinwlrdg vqlaesnrtr itgeevevqd svpadsglya cvtsspsgsd ttyfsvnvsd
121 alpssedddd dddssseeke tdntkpnrmp vapywtspek mekklhavpa aktvkfkcps
181 sgtpnptlrw lkngkefkpd hriggykvry atwsiimdsv vpsdkgnytc iveneygsin
241 htyqldvver sphrpilqag lpanktvalg snvefmckvy sdpqphiqwl khievngski
301 gpdnlpyvqi lktagvnttd kemevlhlrn vsfedageyt clagnsigls hhsawltvle
361 aleerpavmt splyleiiiy ctgafliscm vgsivykmk sgtkksdfhs qmavhklaks
421 iplrrqvtvs adssasmnsg vllvrpsrls ssgtpmlagv seyelpedpr welprdrlvl
481 gkplgegcfg qvvlaeaigl dkdkpnrvtk vavkmlksda tekdlsdlis ememmkmigk
541 hkniinllga ctqdgplyvi veyaskgnlr eylqarrppg leycynpshn peeqlsskdl
601 vscayqvarg meylaskkci hrdlaarnvl vtednvmkia dfglardihh idyykkttng
661 rlpvkwmape alfdriythq sdvwsfgvll weiftlggsp ypgvpveelf kllkeghrmd
721 kpsnctnely mmmrdcwhav psqrptfkql vedldrival tsnqeyldls mpldqyspsf
781 pdtrsstcss gedsvfshep lpeepclprh paqlangglk rr
```

FIG. 3A

SEQ ID NO: 3 – FGFR2 cDNA sequence (Accession No. NM_000141)

```
   1 ggcggcggct ggaggagagc gcggtggaga gccgagcggg cgggcggcgg gtgcggagcg
  61 ggcgagggag cgcgcgcggc cgccacaaag ctcgggcgcc gcggggctgc atgcggcgta
 121 cctggcccgg cgcggcgact gctctccggg ctggcggggg ccggccgcga gccccggggg
 181 ccccgaggcc gcagcttgcc tgcgcgctct gagccttcgc aactcgcgag caaagtttgg
 241 tggaggcaac gccaagcctg agtcctttct tcctctcgtt ccccaaatcc gagggcagcc
 301 cgcgggcgtc atgcccgcgc tcctccgcag cctggggtac gcgtgaagcc cgggaggctt
 361 ggcgccggcg aagacccaag gaccactctt ctgcgtttgg agttgctccc cgcaaccccg
 421 ggctcgtcgc tttctccatc ccgacccacg cggggcgcgg ggacaacaca ggtcgcggag
 481 gagcgttgcc attcaagtga ctgcagcagc agcggcagcg cctcggttcc tgagcccacc
 541 gcaggctgaa ggcattgcgc gtagtccatg cccgtagagg aagtgtgcag atgggattaa
 601 cgtccacatg gagatatgga agaggaccgg ggattggtac cgtaaccatg gtcagctggg
 661 gtcgtttcat ctgcctggtc gtggtcacca tggcaacctt gtccctggcc cggccctcct
 721 tcagtttagt tgaggatacc acattagagc cagaagagcc accaaccaaa taccaaatct
 781 ctcaaccaga agtgtacgtg gctgcgccag gggagtcgct agaggtgcgc tgcctgttga
 841 aagatgccgc cgtgatcagt tggactaagg atgggtgca cttggggccc aacaatagga
 901 cagtgcttat tggggagtac ttgcagataa agggcgccac gcctagagac tccggcctct
 961 atgccttgtac tgccagtagg actgtagaca gtgaaacttg gtacttcatg gtgaatgtca
1021 cagatgccat ctcatccgga gatgatgagg atgacaccga tggtgcggaa gattttgtca
1081 gtgagaacag taacaacaag agagcaccat actggaccaa cacagaaaag atggaaaagc
1141 ggctccatgc tgtgcctgcg ccaacactg tcaagtttcg ctgcccagcc ggggggaacc
1201 caatgccaac catgcggtgg ctgaaaaacg ggaaggagtt taagcaggag catcgcattg
1261 gaggctacaa ggtacgaaac cagcactgga gcctcattat ggaaagtgtg gtcccatctg
1321 acaagggaaa ttatacctgt gtagtggaga atgaatacgg tcccatcaat cacacgtacc
1381 acctggatgt tgtggagcga tcgcctcacc ggcccatcct ccaagccgga ctgccggcaa
1441 atgcctccac agtggtcgga ggagacgtag agtttgtctg caaggtttac agtgatgccc
1501 agcccacat ccagtggatc aagcacgtgg aaaagaacgg cagtaaatac gggcccgacg
1561 ggctgcccta cctcaaggtt ctcaaggccg ccggtgttaa caccacggac aaagagattg
1621 aggttctcta tattcggaat gtaacttttg aggacgctgg ggaatatacg tgcttggcgg
1681 gtaattctat tgggatatcc tttcactctg catggttgac agttctgcca gcgcctggaa
1741 gagaaaagga gattacagct tccccagact acctggagat agccatttac tgcatagggg
1801 tcttcttaat cgcctgtatg gtggtaacag tcatcctgtg ccgaatgaag aacacgacca
1861 agaagccaga cttcagcagc cagccggctg tgcacaagct gaccaaacgt atcccctgc
1921 ggagacaggt aacagtttcg gctgagtcca gctcctccat gaactccaac accccgctgg
1981 tgaggataac aacacgcctc tcttcaacgg cagacacccc catgctggca ggggtctccg
2041 agtatgaact tccagaggac ccaaaatggg agtttccaag agataagctg acactgggca
2101 agccccctggg agaaggttgc tttgggcaag tggtcatggc ggaagcagtg ggaattgaca
2161 aagacaagcc caaggaggcg tcaccgtgg ccgtgaagat gttgaaagat gatgccacag
2221 agaaagacct ttctgatctg gtgtcagaga tggagatgat gaagatgatt gggaaacaca
2281 agaatatcat aaatcttctt ggagcctgca cacaggatgg gcctctctat gtcatagttg
2341 agtatgcctc taaaggcaac ctccgagaat acctccgagc ccggaggcca cccgggatgg
2401 agtactccta tgacattaac cgtgttcctg aggagcagat gaccttcaag gacttggtgt
2461 catgcaccta ccagctggcc agaggcatgg agtacttggc ttcccaaaaa tgtattcatc
```

FIG. 3A (cont'd)

```
2521 gagatttagc agccagaaat gttttggtaa cagaaaacaa tgtgatgaaa atagcagact
2581 ttggactcgc cagagatatc aacaatatag actattacaa aaagaccacc aatgggcggc
2641 ttccagtcaa gtggatggct ccagaagccc tgtttgatag agtatacact catcagagtg
2701 atgtctggtc cttcggggtg ttaatgtggg agatcttcac tttaggggggc tcgccctacc
2761 cagggattcc cgtggaggaa cttttttaagc tgctgaagga aggacacaga atggataagc
2821 cagccaactg caccaacgaa ctgtacatga tgatgaggga ctgttggcat gcagtgccct
2881 cccagagacc aacgttcaag cagttggtag aagacttgga tcgaattctc actctcacaa
2941 ccaatgagga atacttggac ctcagccaac ctctcgaaca gtattcacct agttaccctg
3001 acacaagaag ttcttgttct tcaggagatg attctgtttt ttctccagac cccatgcctt
3061 acgaaccatg ccttcctcag tatccacaca taaacggcag tgttaaaaca tgaatgactg
3121 tgtctgcctg tccccaaaca ggacagcact gggaacctag ctacactgag cagggagacc
3181 atgcctccca gagcttgttg tctccacttg tatatatgga tcagaggagt aaataattgg
3241 aaaagtaatc agcatatgtg taaagattta tacagttgaa aacttgtaat cttccccagg
3301 aggagaagaa ggtttctgga gcagtggact gccacaagcc accatgtaac ccctctcacc
3361 tgccgtgcgt actggctgtg gaccagtagg actcaaggtg gacgtgcgtt ctgccttcct
3421 tgttaatttt gtaataattg gagaagattt atgtcagcac acacttacag agcacaaatg
3481 cagtatatag gtgctggatg tatgtaaata tattcaaatt atgtataaat atatattata
3541 tatttacaag gagttatttt ttgtattgat tttaaatgga tgtcccaatg cacctagaaa
3601 attggtctct cttttttttaa tagctatttg ctaaatgctg ttcttacaca taatttctta
3661 attttcaccg agcagaggtg gaaaaatact tttgctttca gggaaaatgg tataacgtta
3721 atttattaat aaattggtaa tatacaaaac aattaatcat ttatagtttt ttttgtaatt
3781 taagtggcat ttctatgcag gcagcacagc agactagtta atctattgct tggacttaac
3841 tagttatcag atccttgaa aagagaatat ttacaatata tgactaattt ggggaaaatg
3901 aagttttgat ttatttgtgt ttaaatgctg ctgtcagacg attgttctta gacctcctaa
3961 atgccccata ttaaaagaac tcattcatag gaaggtgttt cattttggtg tgcaaccctg
4021 tcattacgtc aacgcaacgt ctaactggac ttcccaagat aaatggtacc agcgtcctct
4081 taaaagatgc cttaatccat tccttgagga cagaccttag ttgaaatgat agcagaatgt
4141 gcttctctct ggcagctggc cttctgcttc tgagttgcac attaatcaga ttagcctgta
4201 ttctcttcag tgaattttga taatggcttc cagactcttt ggcgttggag acgcctgtta
4261 ggatcttcaa gtcccatcat agaaaattga aacacagagt tgttctgctg atagttttgg
4321 ggatacgtcc atcttttaa gggattgctt tcatctaatt ctggcaggac ctcaccaaaa
4381 gatccagcct catacctaca tcagacaaaa tatcgccgtt gttccttctg tactaaagta
4441 ttgtgttttg ctttggaaac acccactcac tttgcaatag ccgtgcaaga tgaatgcaga
4501 ttacactgat cttatgtgtt acaaaattgg agaaagtatt taataaaacc tgttaatttt
4561 tatactgaca ataaaaatgt ttctacagat attaatgtta acaagacaaa ataaatgtca
4621 cgcaacttat tttttttaata aaaaaaaaaa aaaa
```

FIG. 3B

SEQ ID NO: 4 – FGFR2 amino acid sequence (Accession No. NP_000132)

```
  1 mgltstwryg rgpgigtvtm vswgrficlv vvtmatlsla rpsfslvedt tlepeepptk
 61 yqisqpevyv aapgeslevr cllkdaavis wtkdgvhlgp nnrtvligey lqikgatprd
121 sglyactasr tvdsetwyfm vnvtdaissg ddeddtdgae dfvsensnnk rapywtntek
181 mekrlhavpa antvkfrcpa ggnpmptmrw lkngkefkqe hriggykvrn qhwslimesv
241 vpsdkgnytc vveneygsin htyhldvver sphrpilqag lpanastvvg gdvefvckvy
301 sdaqphiqwi khvekngsky gpdglpylkv lkaagvnttd keievlyirn vtfedageyt
361 clagnsigis fhsawltvlp apgrekeita spdyleiaiy cigvfliacm vvtvilcrmk
421 nttkkpdfss qpavhkltkr iplrrqvtvs aessssmnsn tplvrittrl sstadtpmla
481 gvseyelped pkwefprdkl tlgkplgegc fgqvvmaeav gidkdkpkea vtvavkmlkd
541 datekdlsdl vsememmkmi gkhkniinll gactqdgply viveyaskgn lreylrarrp
601 pgmeysydin rvpeeqmtfk dlvsctyqla rgmeylasqk cihrdlaarn vlvtennvmk
661 iadfglardi nnidyykktt ngrlpvkwma pealfdrvyt hqsdvwsfgv lmweiftlgg
721 spypgipvee lfkllkeghr mdkpanctne lymmmrdcwh avpsqrptfk qlvedldril
781 tlttneeyld lsqpleqysp sypdtrsscs sgddsvfspd pmpyepclpq yphingsvkt
```

FIG. 4A

SEQ ID NO: 5 - Human FGFR3 cDNA sequence (Accession No. M64347)

```
1    aaggatggca cagggctggt gccctcggag cgtgtcctgg tggggcccca gcggctgcag
61   gtgctgaatg cctcccacga ggactccggg gcctacagct gccggcagcg gctcacgcag
121  cgcgtactgt gccacttcag tgtgcgggtg acagacgctc catcctcggg agatgacgaa
181  gacgggagg acgaggctga ggacacaggt gtggacacag gggcccctta ctggacacgg
241  cccgagcgga tggacaagaa gctgctggcc gtgccggccg ccaacaccgt ccgcttccgc
301  tgcccagccg ctggcaaccc cactccctcc atctcctggc tgaagaacgg cagggagttc
361  cgcggcgagc accgcattgg aggcatcaag ctgcggcatc agcagtggag cctggtcatg
421  gaaagcgtgg tgccctcgga ccgcggcaac tacacctgcg tcgtggagaa caagtttggc
481  agcatccggc agacgtacac gctggacgtg ctggagcgct cccgcaccg gcccatcctg
541  caggcggggc tgccggccaa ccagacggcg gtgctgggca cgacgtgga gttccactgc
601  aaggtgtaca gtgacgcaca gccccacatc cagtggctca agcacgtgga ggtgaatggc
661  agcaaggtgg gcccggacgg cacaccctac gttaccgtgc tcaagacggc gggcgctaac
721  accaccgaca aggagctaga ggttctctcc ttgcacaacg tcacctttga ggacgccggg
781  gagtacacct gcctggcggg caattctatt gggttttctc atcactctgc gtggctggtg
841  gtgctgccag ccgaggagga gctggtggag gctgacgagg cgggcagtgt gtatgcaggc
901  atcctcagct acggggtggg cttcttcctg ttcatcctgg tggtggcggc tgtgaccgtc
961  tgccgcctgc gcagcccccc caagaaaggc ctgggctccc ccaccgtgca aagatctcc
1021 cgcttcccgc tcaagcgaca ggtgtccctg gagtccaacg cgtccatgag ctccaacaca
1081 ccactggtgc gcatcgcaag gctgtcctca ggggagggcc ccacgctggc caatgtctcc
1141 gagctcgagc tgcctgccga ccccaaatgg gagctgtctc gggcccggct gaccctgggc
1201 aagcccttg ggagggctg cttcggccag gtggtcatgg cggaggccat cggcattgac
1261 aaggaccggg ccgccaagcc tgtcaccgta gccgtgaaga tgctgaaaga cgatgccact
1321 gacaaggacc tgtcggacct ggtgtctgag atggagatga tgaagatgat cgggaaacac
1381 aaaaacatca tcaacctgct gggcgcctgc acgcagggcg gccccctgta cgtgctggtg
1441 gagtacgcgg ccaagggtaa cctgcgggag tttctgcggg cgcggcggcc cccgggcctg
1501 gactactcct tcgacacctg caagccgccc gaggagcagc tcaccttcaa ggacctggtg
1561 tcctgtgcct accaggtggc ccggggcatg gagtacttgg cctcccagaa gtgcatccac
1621 agggacctgg ctgcccgcaa tgtgctggtg accgaggaca acgtgatgaa gatcgcagac
1681 ttcgggctgg cccgggacgt gcacaacctc gactactaca agaagacaac caacggccgg
1741 ctccccgtga gtggatggc gcctgaggcc ttgtttgacc gagtctacac tcaccagagt
1801 gacgtctggt cctttggggt cctgctctgg gagatcttca cgctgggggg ctcccccgtac
1861 cccggcatcc ctgtggagga gctcttcaag ctgctgaagg agggccaccg catggacaag
1921 cccgccaact gcacacacga cctgtacatg atcatgcggg agtgctggca tgccgcgccc
1981 tcccagaggc ccaccttcaa gcagctggtg gaggacctgg accgtgtcct taccgtgacg
2041 tccaccgacg agtacctgga cctgtcggcg cctttcgagc agtactcccc gggtggccag
2101 gacacccca gctccagctc ccaggggac gactccgtgt tgcccacga cctgctgccc
2161 ccggccccac ccagcagtgg gggctcgcgg acgtgaaggg ccactggtcc caacaatgt
2221 gaggggtccc tagcagccca ccctgctgct ggtgcacagc cactcccgg catgagactc
2281 agtgcagatg gagagacagc tacacagagc tttggtctgt gtgtgtgtgt gtgcgtgtgt
2341 gtgtgtgtgt gcacatccgc gtgtgcctgt gtgcgtgcgc atcttgcctc caggtgcaga
2401 ggtaccctgg gtgtccccgc tgctgtgcaa cggtctcctg actggtgctg cagcaccgag
2461 gggccttgt tctgggggga cccagtgcag aatgtaagtg ggcccacccg gtgggacccc
```

FIG. 4A (cont'd)

```
2521 gtggggcagg gagctgggcc cgacatggct cggcctctgc ctttgcacca cgggacatca
2581 cagggtgcgc tcggccccctc ccacacccaa agctgagcct gcagggaagc cccacatgtc
2641 cagcaccttg tgcctggggt gttagtggca ccgcctcccc acctccaggc tttcccactt
2701 cccaccctgc ccctcagaga ctgaaattac gggtacctga agatgggagc ctttacctt
2761 tatgcaaaag gtttattccg gaaactagtg tacatttcta taaatagatg ctgtgtatat
2821 ggtatatata catatatata tataacatat atggaagagg aaaaggctgg tacaacggag
2881 gcctgcgacc ctgggggcac aggaggcagg catggccctg ggcggggcgt gggggggcgt
2941 ggagggaggc cccaggggtc tcacccatgc aagcagagga ccagggcttt ttctggcacc
3001 gcagttttgt tttaaaactg gacctgtata tttgtaaagc tatttatggg cccctggcac
3061 tcttgttccc acaccccaac acttccagca tttagctggc cacatggcgg agagttttaa
3121 ttttttaactt attgacaacc gagaaggttt atcccgccga tagagggacg gccaagaatg
3181 tacgtccagc ctgccccgga gctggaggat cccctccaag cctaaaaggt tgttaatagt
3241 tggaggtgat tccagtgaag atattttatt tgctttgtcc ttttttcagga gaattagatt
3301 tctataggat ttttctttag gagatttatt ttttggactt caaagcaagc tggtattttc
3361 atacaaattc ttctaattgc tgtgtgtccc aggcagggag acggtttcca gggaggggcc
3421 ggccctgtgt gcaggttccg atgttattag atgttacaag tttatatata tctatatata
3481 taatttattg agtttttaca agatgtattt gttgtagact taacacttct tacgcaatgc
3541 ttctagagtt ttatagcctg gactgctacc tttcaaagct tggagggaag ccgtgaattc
3601 agttggttcg ttctgtactg ttactgggcc ctgagtctgg gcagctgtcc cttgcttgcc
3661 tgcagggcca tggctcaggg tggtctcttc ttggggccca gtgcatggtg gccagaggtg
3721 tcacccaaac cggcaggtgc gattttgtta acccagcgac gaactttccg aaaaataaag
3781 acacctggtt gctaacctga aaaaaaaaaa aaaaaaaaaa aaaaaaaa
```

FIG. 4B

SEQ ID NO: 6 - Human FGFR3 amino acid sequence (Accession No. NP_000133)

```
1   mgapacalal cvavaivaga sseslgteqr vvgraaevpg pepgqqeqlv fgsgdavels
61  cpppgggpmg ptvwvkdgtg lvpservlvg pqrlqvlnas hedsgayscr qrltqrvlch
121 fsvrvtdaps sgddedgede aedtgvdtga pywtrpermd kkllavpaan tvrfrcpaag
181 nptpsiswlk ngrefrgehr iggiklrhqq wslvmesvvp sdrgnytcvv enkfgsirqt
241 ytldvlersp hrpilqaglp anqtavlgsd vefhckvysd aqphiqwlkh vevngskvgp
301 dgtpyvtvlk taganttdke levlslhnvt fedageytcl agnsigfshh sawlvvlpae
361 cclvcadcag svyagilsyg vgfflfilvv aavtlcrlrs ppkkglgspt vhkisrfplk
421 rqvslesnas mssntplvri arlssgegpt lanvselelp adpkwelsra rltlgkplge
481 gcfgqvvmae aigidkdraa kpvtavkml kddatdkdls dlvsememmk migkhkniin
541 llgactqggp lyvlveyaak gnlreflrar rppgldysfd tckppeeqlt fkdlvscayq
601 vargmeylas qkcihrdlaa rnvlvtednv mkiadfglar dvhnldyykk ttngrlpvkw
661 mapealfdrv ythqsdvwsf gvllweiftl ggspypgipv eelfkllkeg hrmdkpanct
721 hdlymimrec whaapsqrpt fkqlvedldr vltvtstdey ldlsapfeqy spggqdtpss
781 sssgddsvfa hdllppapps sggsrt
```

FIG. 5A

SEQ ID NO: 7 - Human FGFR4 cDNA sequence (Accession No. NM_002011)

```
   1 ctcgctcccg gccgaggagc gctcgggctg tctgcggacc ctgccgcgtg caggggtcgc
  61 ggccggctgg agctgggagt gaggcggcgg aggagccagg tgaggaggag ccaggaaggc
 121 agttggtggg aagtccagct tgggtccctg agagctgtga aaggagatg cggctgctgc
 181 tggccctgtt ggggtcctg ctgagtgtgc ctgggcctcc agtcttgtcc ctggaggcct
 241 ctgaggaagt ggagcttgag ccctgcctgg ctcccagcct ggagcagcaa gagcaggagc
 301 tgacagtagc ccttgggcag cctgtgcgtc tgtgctgtgg gcgggctgag cgtggtggcc
 361 actggtacaa ggagggcagt cgcctggcac ctgctggccg tgtacggggc tggaggggcc
 421 gcctagagat tgccagcttc ctacctgagg atgctggccg ctacctctgc ctggcacgag
 481 gctccatgat cgtcctgcag aatctcacct tgattacagg tgactccttg acctccagca
 541 acgatgatga ggaccccaag tcccataggg acccctcgaa taggcacagt taccccccagc
 601 aagcacccta ctggacacac ccccagcgca tggagaagaa actgcatgca gtacctgcgg
 661 ggaacaccgt caagttccgc tgtccagctg caggcaaccc cacgcccacc atccgctggc
 721 ttaaggatgg acaggccttt catggggaga accgcattgg aggcattcgg ctgcgccatc
 781 agcactggag tctcgtgatg gagagcgtgg tgccctcgga ccgcggcaca tacacctgcc
 841 tggtagagaa cgctgtgggc agcatccgct ataactacct gctagatgtg ctggagcggt
 901 ccccgcaccg gcccatcctg caggccgggc tcccggccaa caccacagcc gtggtgggca
 961 gcgacgtgga gctgctgtgc aaggtgtaca gcgatgccca gccccacatc agtggctga
1021 agcacatcgt catcaacggc agcagcttcg gagccgacgg tttccctat gtgcaagtcc
1081 taaagactgc agacatcaat agctcagagg tggaggtcct gtacctgcgg aacgtgtcag
1141 ccgaggacgc aggcgagtac acctgcctcg caggcaattc catcggcctc tcctaccagt
1201 ctgcctggct cacggtgctg ccagaggagg accccacatg gaccgcagca gcgcccgagg
1261 ccaggtatac ggacatcatc ctgtacgcgt cgggctccct ggccttggct gtgctcctgc
1321 tgctggccgg gctgtatcga gggcaggcgc tccacggccg cgcccccgc ccgccgcca
1381 ctgtgcagaa gctctcccgc ttccctctgg cccgacagtt ctccctggag tcaggctctt
1441 ccggcaagtc aagctcatcc ctggtacgag gcgtgcgtct ctcctccagc ggccccgcct
1501 tgctcgccgg cctcgtgagt ctagatctac ctctcgaccc actatgggag ttcccccggg
1561 acaggctggt gcttgggaag ccctaggcg agggctgctt tggccaggta gtacgtgcag
1621 aggcctttgg catggaccct gcccggcctg accaagccag cactgtggcc gtcaagatgc
1681 tcaaagacaa cgcctctgac aaggacctgg ccgacctggt ctcggagatg gaggtgatga
1741 agctgatcgg ccgacacaag aacatcatca acctgcttgg tgtctgcacc caggaagggc
1801 ccctgtacgt gatcgtggag tgcgccgcca agggaaacct gcgggagttc ctgcgggccc
1861 ggcgcccccc aggccccgac ctcagccccg acggtcctcg gagcagtgag gggccgctct
1921 ccttcccagt cctggtctcc tgcgcctacc aggtggcccg aggcatgcag tatctggagt
1981 cccggaagtg tatccaccgg gacctggctg cccgcaatgt gctggtgact gaggacaatg
2041 tgatgaagat tgctgacttt gggctggccc gcggcgtcca ccacattgac tactataaga
2101 aaaccagcaa cggccgcctg cctgtgaagt ggatggcgcc cgaggccttg tttgaccggg
2161 tgtacacaca ccagagtgac gtgtggtctt ttgggatcct gctatgggag atcttcaccc
2221 tcggggggctc cccgtatcct ggcatcccgg tggaggagct gttctcgctg ctgcgggagg
2281 gacatcggat ggaccgaccc ccacactgcc ccccagagct gtacgggctg atgcgtgagt
2341 gctggcacgc agcgcccctcc cagaggccta ccttcaagca gctggtggag gcgctggaca
2401 aggtcctgct ggccgtctct gaggagtacc tcgacctccg cctgaccttc ggacccatt
2461 cccctctgg tggggacgcc agcagcacct gctcctccag cgattctgtc ttcagccacg
```

FIG. 5A (cont'd)

```
2521 accccctgcc attgggatcc agctccttcc ccttcgggtc tggggtgcag acatgagcaa
2581 ggctcaaggc tgtgcaggca cataggctgg tggccttggg ccttggggct cagccacagc
2641 ctgacacagt gctcgacctt gatagcatgg ggcccctggc ccagagttgc tgtgccgtgt
2701 ccaagggccg tgcccttgcc cttggagctg ccgtgcctgt gtcctgatgg cccaaatgtc
2761 agggttctgc tcggcttctt ggaccttggc gcttagtccc catcccgggt ttggctgagc
2821 ctggctggag agctgctatg ctaaacctcc tgcctcccaa taccagcagg aggttctggg
2881 cctctgaacc ccctttcccc acacctcccc ctgctgctgc tgccccagcg tcttgacggg
2941 agcattggcc cctgagccca gagaagctgg aagcctgccg aaaacaggag caaatggcgt
3001 tttataaatt atttttttga aataaaaaaa aaaaaaaaa
```

FIG. 5B

SEQ ID NO: 8 - Human FGFR4 amino acid sequence (Accession No. NP_002002 )

```
1    mrlllallgv llsvpgppvl slcasccvcl cpclapslcq qcqcltvalg qpvrlccgra
61   ergghwykeg srlapagrvr gwrgrleias flpedagryl clargsmivl qnltlitgds
121  ltssnddedp kshrdpsnrh sypqqapywt hpqrmekklh avpagntvkf rcpaagnptp
181  tirwlkdgqa fhgenriggi rlrhqhwslv mesvvpsdrg tytclvenav gsirynylld
241  vlcrsphrpi lqaglpantt avvgsdvcll ckvysdaqph iqwlkhivin gssfgadgfp
301  yvqvlktadi nssevevlyl rnvsaedage ytclagnsig lsyqsawltv lpeedptwta
361  aapearytdi ilyasgslal avllllagly rgqalhgrhp rppatvqkls rfplarqfsl
421  esgssgksss slvrgvrlss sgpallaglv sldlpldplw efprdrlvlg kplgegcfgq
481  vvracafgmd parpdqastv avkmlkdnas dkdladlvsc mcvmkligrh kniinllgvc
541  tqegplyviv ecaakgnlre flrarrppgp dlspdgprss egplsfpvlv scayqvargm
601  qylesrkcih rdlaarnvlv tednvmkiad fglargvhhi dyykktsngr lpvkwmapea
661  lfdrvythqs dvwsfgillw eiftlggspy pgipveelfs llreghrmdr pphcppelyg
721  lmrccwhaap sqrptfkqlv caldkvllav sccyldlrlt fgpyspsggd asstcsssds
781  vfshdplplg sssfpfgsgv qt
```

FIG. 6A

SEQ ID NO: 9 - Human Hsp90 cDNA sequence (Accession No. NM_001017963 )

```
   1 gactgcgcag gcgtgctcac ctggcgtgct ccacccgact gggcgtccgc aggctcctcc
  61 cccgggtgtg gcctccgggc ggcatggctg cttcccaggt gatgccggct tcagctagtg
 121 gggtctagtt gaccgttccg cagccgccag ggccagcgga aagccggtca gggggaaccg
 181 cggcggggct ggtgtcatga gcctgaggtg aacttgaggg tgcctcctca gcggtctccc
 241 gccctgccct gaggggcgcc gggaccccaa agagcggagg aagagcgcca ccccgacggc
 301 caccgcttcg gagccagcac gcggggtacc ctacggggag cgcggatgcc cccgtgttcg
 361 ggcggggacg gctccacccc tcctgggccc tcccttcggg acagggactg tcccgcccag
 421 agtgctgaat cccgcgcga ccgtctggat ccccgccag gaagcccctc tgaagcctcc
 481 tcgccgccgt ttctgagaag cagggcacct gttaactggt accaagaaaa ggcccaagtg
 541 tttctctggc atctgatggt gtctggatcc accactctac tctgtctctg gaaacagccc
 601 ttccacgtct ctgcattccc tgtcaccgcg tcactggcct tcagacagag ccaaggtgca
 661 gggcaacacc tctacaagga tctgcagcca tttatattgc ttaggctact gatgcctgag
 721 gaaacccaga cccaagacca accgatggag gaggaggagg ttgagacgtt cgcctttcag
 781 gcagaaattg cccagttgat gtcattgatc atcaatactt tctactcgaa caaagagatc
 841 tttctgagag agctcatttc aaattcatca gatgcattgg acaaaatccg gtatgaaagc
 901 ttgacagatc ccagtaaaat agactctggg aaagagctgc atattaacct tataccgaac
 961 aaacaagatc gaactctcac tattgtggat actggaattg gaatgaccaa ggctgacttg
1021 atcaataacc ttggtactat cgccaagtct gggaccaaag cgttcatgga gctttgcag
1081 gctggtgcag atatctctat gattggccag ttcggtgttg gttttattc tgcttatttg
1141 gttgctgaga agtaactgt gatcaccaaa cataacgatg atgagcagta cgcttgggag
1201 tcctcagcag ggggatcatt cacagtgagg acagacacag gtgaacctat gggtcgtgga
1261 acaaaagtta tcctacacct gaaagaagac caaactgagt acttggagga acgaagaata
1321 aaggagattg tgaagaaaca ttctcagttt attggatatc ccattactct ttttgtggag
1381 aaggaacgtg ataaagaagt aagcgatgat gaggctgaag aaaaggaaga caaagaagaa
1441 gaaaaagaaa agaagagaa agagtcggaa gacaaacctg aaattgaaga tgttggttct
1501 gatgaggaag aagaaaagaa ggatggtgac aagaagaaga agaagaagat taaggaaaag
1561 tacatcgatc aagaagagct caacaaaaca aagcccatct ggaccagaaa tcccgacgat
1621 attactaatg aggagtacgg agaattctat aagagcttga ccaatgactg ggaagatcac
1681 ttggcagtga agcatttttc agttgaagga cagttggaat tcagagccct tctatttgtc
1741 ccacgacgtg ctcctttga tctgtttgaa acagaaaga aaagaacaa catcaaattg
1801 tatgtacgca gagtttcat catggataac tgtgaggagc taatccctga atatctgaac
1861 ttcattagag gggtggtaga ctcggaggat ctccctctaa acatatcccg tgagatgttg
1921 caacaaagca aaattttgaa agttatcagg aagaatttgg tcaaaaaatg cttagaactc
1981 tttactgaac tggcggaaga taaagagaac tacaagaaat tctatgagca gttctctaaa
2041 aacataaagc ttggaataca cgaagactct caaaatcgga gaagctttc agagctgtta
2101 aggtactaca catctgcctc tggtgatgag atggtttctc tcaaggacta ctgcaccaga
2161 atgaaggaga accagaaaca tatctattat atcacaggtg agaccaagga ccaggtagct
2221 aactcagcct tgtggaacg tcttcggaaa catggcttag aagtgatcta tatgattgag
2281 cccattgatg agtactgtgt ccaacagctg aaggaatttg aggggaagac tttagtgtca
2341 gtcaccaaag aaggcctgga acttccagag gatgaagaag agaaaagaa gcaggaagag
2401 aaaaaaacaa agtttgagaa cctctgcaaa atcatgaaag acatattgga gaaaaagtt
2461 gaaaaggtgg ttgtgtcaaa ccgattggtg acatctccat gctgtattgt cacaagcaca
```

FIG. 6A (cont'd)

```
2521 tatggctgga cagcaaacat ggagagaatc atgaaagctc aagccctaag agacaactca
2581 acaatgggtt acatggcagc aaagaaacac ctggagataa accctgacca ttccattatt
2641 gagaccttaa ggcaaaaggc agaggctgat aagaacgaca agtctgtgaa ggatctggtc
2701 atcttgcttt atgaaactgc gctcctgtct tctggcttca gtctggaaga tccccagaca
2761 catgctaaca ggatctacag gatgatcaaa cttggtctgg gtattgatga agatgaccct
2821 actgctgatg ataccagtgc tgctgtaact gaagaaatgc caccccttga aggagatgac
2881 gacacatcac gcatggaaga agtagactaa tctctggctg agggatgact tacctgttca
2941 gtactctaca attcctctga taatatattt tcaaggatgt ttttctttat ttttgttaat
3001 attaaaaagt ctgtatggca tgacaactac tttaagggga agataagatt tctgtctact
3061 aagtgatgct gtgatacctt aggcactaaa gcagagctag taatgctttt tgagtttcat
3121 gttggttttat tttcacagat tggggtaacg tgcactgtaa gacgtatgta acatgatgtt
3181 aactttgtgg tctaaagtgt ttagctgtca agccggatgc ctaagtagac caaatcttgt
3241 tattgaagtg ttctgagctg tatcttgatg tttagaaaag tattcgttac atcttgtagg
3301 atctactttt tgaacttttc attccctgta gttgacaatt ctgcatgtac tagtcctcta
3361 gaaataggtt aaactgaagc aacttgatgg aaggatctct ccacagggct tgttttccaa
3421 agaaaagtat tgtttggagg agcaaagtta aaagcctacc taagcatatc gtaaagctgt
3481 tcaaaaataa ctcagaccca gtcttgtgga tggaaatgta gtgctcgagt cacattctgc
3541 ttaaagttgt aacaaataca gatgagttaa aagatattgt gtgacagtgt cttatttagg
3601 gggaaagggg agtatctgga tgacagttag tgccaaaatg taaaacatga ggcgctagca
3661 ggagatggtt aaacactagc tgctccaagg gttgacatgg tcttcccagc atgtactcag
3721 caggtgtggg gtggagcaca cgtaggcaca gaaaacagga atgcagacaa catgcatccc
3781 ctgcgtccat gagttacatg tgttctctta gtgtccacgt tgttttgatg ttattcatgg
3841 aataccttct gtgttaaata cagtcactta attccttggc cttaaaa
```

FIG. 6B

SEQ ID NO: 10 - Human Hsp90 amino acid sequence (Accession No. NP_001017963)

```
1   mppcsggdgs tppgpslrdr dcpaqsaeyp rdrldprpgs pseassppfl rsrapvnwyq
61  ekaqvflwhl mvsgsttllc lwkqpfhvsa fpvtaslafr qsqgagqhly kdlqpfillr
121 llmpeetqtq dqpmeeeve tfafqaeiaq lmsliintfy snkeiflrel isnssdaldk
181 iryesltdps kldsgkelhi nlipnkqdrt ltivdtgigm tkadlinnlg tiaksgtkaf
241 mealqagadi smigqfgvgf ysaylvaekv tvitkhndde qyawessagg sftvrtdtge
301 pmgrgtkvil hlkedqteyl eerrikeivk khsqfigypi tlfvekerdk evsddeaeek
361 edkeeekeke ekesedkpei edvgsdeeee kkdgdkkkkk kikekyidqe elnktkpiwt
421 rnpdditnee ygefyksltn dwedhlavkh fsvegqlefr allfvprrap fdlfenrkkk
481 nniklyvrrv fimdnceeli peylnfirgv vdsedlplni sremlqqski lkvirknlvk
541 kclelftela edkenykkfy eqfskniklg ihedsqnrkk lsellryyts asgdemvslk
601 dyctrmkenq khiyyitget kdqvansafv erlrkhglev iymiepidey cvqqlkefeg
661 ktlvsvtkeg lelpedeeek kkqeekktkf enlckimkdi lekkvekvvv snrlvtspcc
721 ivtstygwta nmerimkaqa lrdnstmgym aakkhleinp dhsiietlrq kaeadkndks
781 vkdlvillye tallssgfsl edpqthanri yrmiklglgi deddptaddt saavteempp
841 legdddtsrm eevd
```

FIG. 16
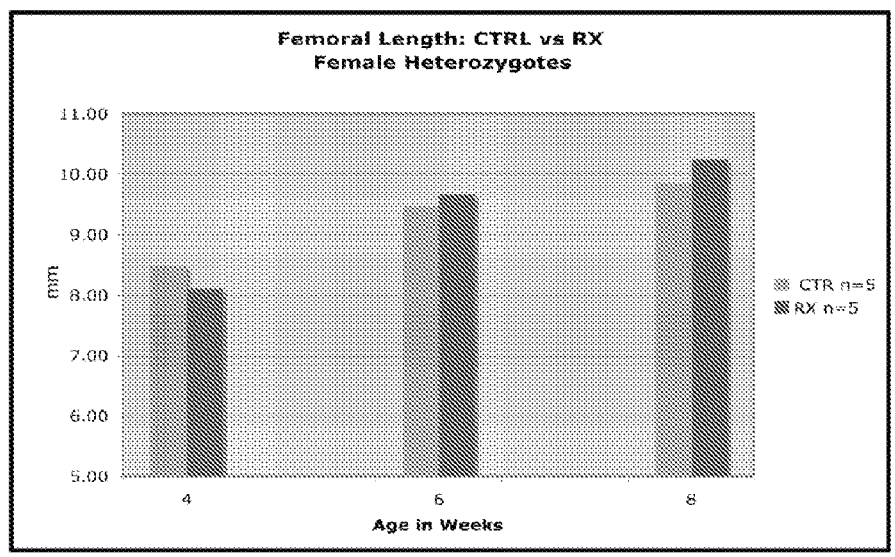
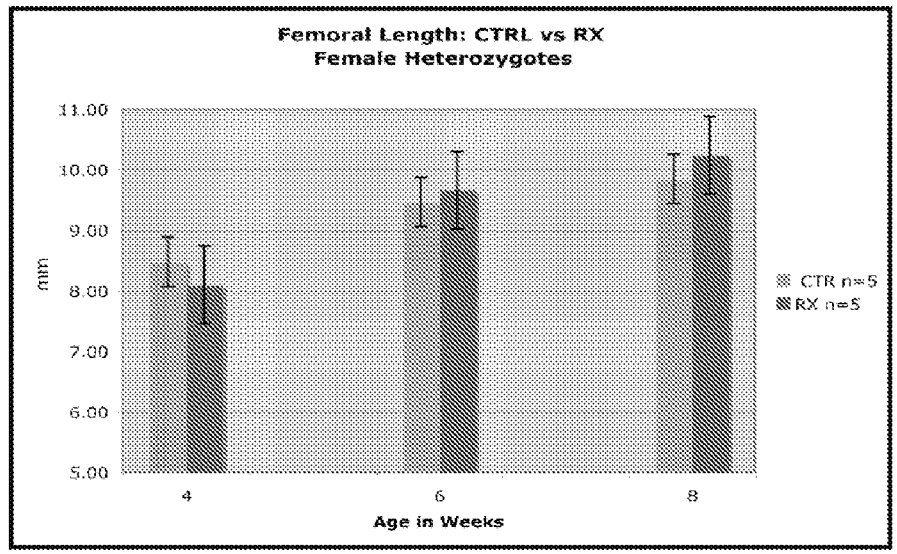

FIG. 17
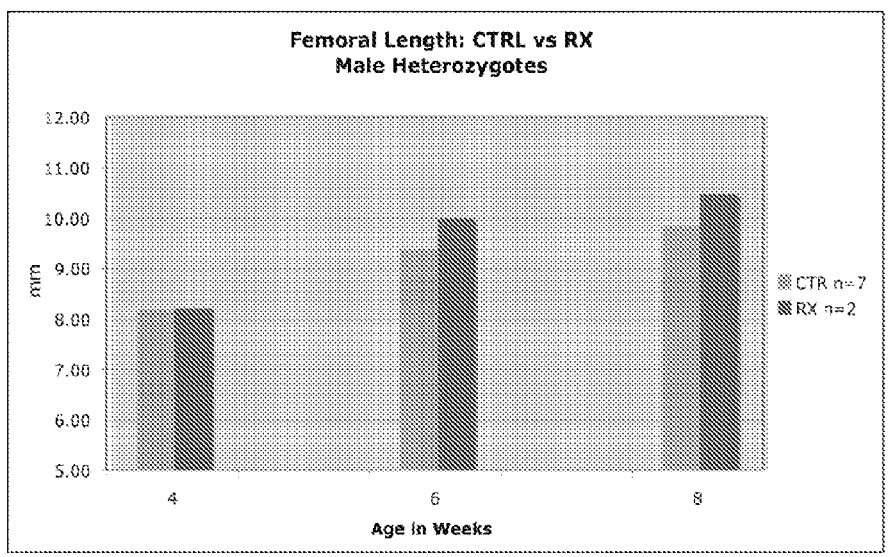
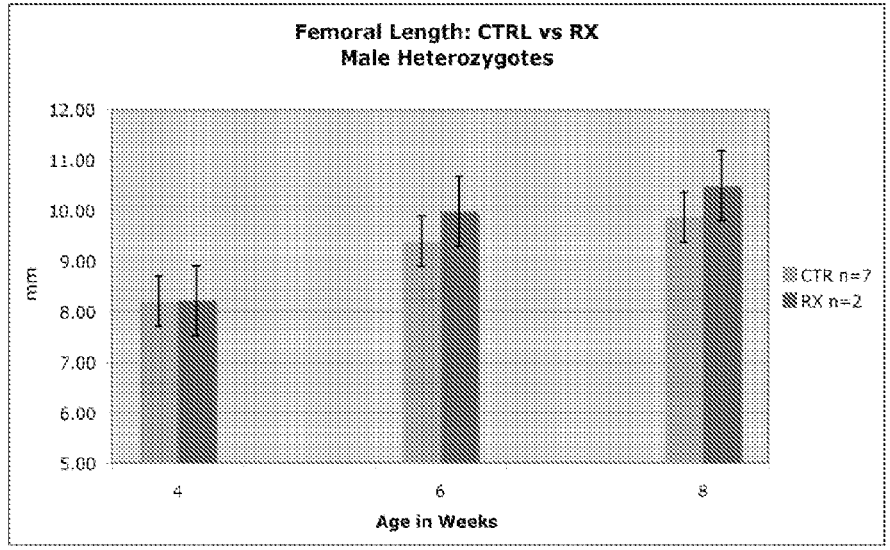

SEQUENCE LISTING

```
<160> NUMBER OF SEQ ID NOS: 16

<210> SEQ ID NO 1
<211> LENGTH: 5917
<212> TYPE: DNA
<213> ORGANISM: Homo sapiens

<400> SEQUENCE: 1
agatgcaggg gcgcaaacgc caaaggagac caggctgtag gaagagaagg gcagagcgcc      60
ggacagctcg gcccgctccc cgtcctttgg ggccgcggct ggggaactac aaggcccagc     120
aggcagctgc aggggcgga ggcggaggag ggaccagcgc gggtgggagt gagagagcga     180
gccctcgcgc cccgccggcg catagcgctc ggagcgctct tgcggccaca ggcgcggcgt     240
cctcggcggc gggcggcagc tagcgggagc cgggacgccg gtgcagccgc agcgcgcgga     300
ggaacccggg tgtgccggga gctgggcggc cacgtccgga cgggaccgag accccctcgta     360 gcgcattgcg gcgacctcgc cttccccggc cgcgagcgcg ccgctgcttg aaaagccgcg     420
gaacccaagg acttttctcc ggtccgagct cggggcgccc cgcagggcgc acggtacccg     480
tgctgcagtc gggcacgccg cggcgccggg gcctccgcag ggcgatggag cccggtctgc     540
aaggaaagtg aggcgccgcc gctgcgttct ggaggagggg ggcacaaggt ctggagaccc     600 cgggtggcg acgggagccc tccccccgcc ccgcctccgg ggcaccagct ccggctccat     660
tgttcccgcc cgggctggag gcgccgagca ccgagcgccg ccgggagtcg agcgccggcc     720
gcggagctct tgcgaccccg ccaggacccg aacagagccc gggggcggcg ggccggagcc     780
ggggacgcgg gcacacgccc gctcgcacaa gccacggcgg actctcccga ggcggaacct     840
ccacgccgag cgagggtcag tttgaaaagg aggatcgagc tcactgtgga gtatccatgg     900
agatgtggag ccttgtcacc aacctctaac tgcagaactg ggatgtggag ctggaagtgc     960
ctcctcttct gggctgtgct ggtcacagcc acactctgca ccgctaggcc gtccccgacc    1020
ttgcctgaac aagcccagcc ctggggagcc cctgtggaag tggagtcctt cctggtccac    1080
cccggtgacc tgctgcagct tcgctgtcgg ctgcgggacg atgtgcagag catcaactgg    1140
ctgcgggacg gggtgcagct ggcggaaagc aaccgcaccc gcatcacagg ggaggaggtg    1200
gaggtgcagg actccgtgcc cgcagactcc ggcctctatg cttgcgtaac cagcagcccc    1260
tcgggcagtg acaccaccta cttctccgtc aatgtttcag atgctctccc ctcctcggag    1320
gatgatgatg atgatgatga ctcctcttca gaggagaaag aaacagataa caccaaacca    1380
```

| | |
|---|---|
| aaccgtatgc ccgtagctcc atattggaca tccccagaaa agatggaaaa gaaattgcat | 1440 |
| gcagtgccgg ctgccaagac agtgaagttc aaatgccctt ccagtgggac cccaaacccc | 1500 |
| acactgcgct ggttgaaaaa tggcaaagaa ttcaaacctg accacagaat tggaggctac | 1560 |
| aaggtccgtt atgccacctg gagcatcata atggactctg tggtgccctc tgacaagggc | 1620 |
| aactacacct gcattgtgga gaatgagtac ggcagcatca accacacata ccagctggat | 1680 |
| gtcgtggagc ggtcccctca ccggcccatc ctgcaagcag ggttgcccgc caacaaaaca | 1740 |
| gtggccctgg gtagcaacgt ggagttcatg tgtaaggtgt acagtgaccc gcagccgcac | 1800 |
| atccagtggc taaagcacat cgaggtgaat gggagcaaga ttggcccaga caacctgcct | 1860 |
| tatgtccaga tcttgaagac tgctggagtt aataccaccg acaaagagat ggaggtgctt | 1920 |
| cacttaagaa atgtctcctt tgaggacgca ggggagtata cgtgcttggc gggtaactct | 1980 |
| atcggactct cccatcactc tgcatggttg accgttctgg aagccctgga agagaggccg | 2040 |
| gcagtgatga cctcgcccct gtacctggag atcatcatct attgcacagg ggccttcctc | 2100 |
| atctcctgca tggtggggtc ggtcatcgtc tacaagatga gagtggtac caagaagagt | 2160 |
| gacttccaca gccagatggc tgtgcacaag ctggccaaga gcatccctct gcgcagacag | 2220 |
| gtaacagtgt ctgctgactc cagtgcatcc atgaactctg ggttcttct ggttcggcca | 2280 |
| tcacggctct cctccagtgg gactcccatg ctagcagggg tctctgagta tgagcttccc | 2340 |
| gaagaccctc gctgggagct gcctcgggac agactggtct taggcaaacc cctgggagag | 2400 |
| ggctgctttg gcaggtggt gttggcagag gctatcgggc tggacaagga caaacccaac | 2460 |
| cgtgtgacca aagtggctgt gaagatgttg aagtcggacg caacagagaa agacttgtca | 2520 |
| gacctgatct cagaaatgga gatgatgaag atgatcggga gcataagaa tatcatcaac | 2580 |
| ctgctggggg cctgcacgca ggatggtccc ttgtatgtca tcgtggagta tgcctccaag | 2640 |
| ggcaacctgc gggagtacct gcaggccgg aggcccccag ggctggaata ctgctacaac | 2700 |
| cccagccaca cccagaggga gcagctctcc tccaaggacc tggtgtcctg cgcctaccag | 2760 |
| gtggcccgag gcatggagta tctggcctcc aagaagtgca tacaccgaga cctggcagcc | 2820 |
| aggaatgtcc tggtgacaga ggacaatgtg atgaagatag cagactttgg cctcgcacgg | 2880 |
| gacattcacc acatcgacta ctataaaaag acaaccaacg gccgactgcc tgtgaagtgg | 2940 |
| atggcacccg aggcattatt tgaccggatc tacacccacc agagtgatgt gtggtctttc | 3000 |
| ggggtgctcc tgtgggagat cttcactctg ggcggctccc catacccgg tgtgcctgtg | 3060 |
| gaggaacttt tcaagctgct gaaggagggt caccgcatgg acaagccag taactgcacc | 3120 |
| aacgagctgt acatgatgat gcgggactgc tggcatgcag tgccctcaca gagacccacc | 3180 |
| ttcaagcagc tggtggaaga cctggaccgc atcgtggcct tgacctccaa ccaggagtac | 3240 |
| ctggacctgt ccatgcccct ggaccagtac tcccccagct ttcccgacac ccggagctct | 3300 |
| acgtgctcct caggggagga ttccgtcttc tctcatgagc cgctgcccga ggagcctgc | 3360 |
| ctgccccgac acccagccca gcttgccaat ggcggactca aacgccgctg actgccaccc | 3420 |
| acacgccctc cccagactcc accgtcagct gtaaccctca cccacagccc ctgctgggcc | 3480 |
| caccacctgt ccgtccctgt cccctttcct gctggcagga gccggctgcc taccaggggc | 3540 |
| cttcctgtgt ggcctgcctt caccccactc agctcacctc tccctccacc tcctctccac | 3600 |
| ctgctggtga gaggtgcaaa gaggcagatc tttgctgcca gccacttcat cccctcccag | 3660 |
| atgttggacc aacaccctc cctgccacca ggcactgcct ggagggcagg gagtgggagc | 3720 |
| caatgaacag gcatgcaagt gagagcttcc tgagctttct cctgtcggtt tggtctgttt | 3780 |

```
tgccttcacc cataagcccc tcgcactctg gtggcaggtg ccttgtcctc agggctacag    3840
cagtagggag gtcagtgctt cgtgcctcga ttgaaggtga cctctgcccc agataggtgg    3900
tgccagtggc ttattaattc cgatactagt ttgctttgct gaccaaatgc ctggtaccag    3960
aggatggtga ggcgaaggcc aggttggggg cagtgttgtg gccctggggc ccagccccaa    4020
actgggggct ctgtatatag ctatgaagaa acacaaagt gtataaatct gagtatatat     4080
ttacatgtct ttttaaaagg gtcgttacca gagatttacc catcgggtaa gatgctcctg    4140
gtggctggga ggcatcagtt gctatatatt aaaacaaaa aagaaaaaaa aggaaaatgt     4200
ttttaaaaag gtcatatatt ttttgctact tttgctgttt tatttttta aattatgttc     4260 taaacctatt ttcagtttag gtccctcaat aaaaattgct gctgcttcat ttatctatgg    4320
gctgtatgaa aagggtggga atgtccactg gaaagaaggg acacccacgg gccctggggc    4380
taggtctgtc ccgagggcac cgcatgctcc cggcgcaggt tccttgtaac ctcttcttcc    4440 taggtccctgc acccagacct cacgacgcac ctcctgcctc tccgctgctt ttggaaagtc   4500 agaaaagaa gatgtctgct tcgagggcag gaaccccatc catgcagtag aggcgctggg     4560
cagagagtca aggcccagca gccatcgacc atggatggtt tcctccaagg aaaccggtgg    4620
ggttgggctg gggagggggc acctacctag gaatagccac ggggtagagc tacagtgatt    4680
aagaggaaag caagggcgcg gttgctcacg cctgtaatcc cagcactttg ggacaccgag    4740
gtgggcagat cacttcaggt caggagtttg agaccagcct ggccaactta gtgaaacccc    4800
atctctacta aaaatgcaaa aattatccag gcatggtggc acacgcctgt aatcccagct    4860
ccacaggagg ctgaggcaga atcccttgaa gctgggaggc ggaggttgca gtgagccgag    4920
attgcgccat tgcactccag cctgggcaac agagaaaaca aaaggaaaa caatgatga      4980 aggtctgcag aaactgaaac ccagacatgt gtctgccccc tctatgtggg catggttttg    5040
ccagtgcttc taagtgcagg agaacatgtc acctgaggct agttttgcat tcaggtccct    5100
ggcttcgttt cttgttggta tgcctcccca gatcgtcctt cctgtatcca tgtgaccaga    5160
ctgtatttgt tgggactgtc gcagatcttg gcttcttaca gttcttcctg tccaaactcc    5220
atcctgtccc tcaggaacgg ggggaaaatt ctccgaatgt ttttggtttt ttggctgctt    5280
ggaatttact tctgccacct gctggtcatc actgtcctca ctaagtggat tctggctccc    5340
ccgtacctca tggctcaaac taccactcct cagtcgctat attaaagctt atattttgct    5400
ggattactgc taaatacaaa agaaagttca atatgttttc atttctgtag ggaaaatggg    5460
attgctgctt taaatttctg agctagggat ttttggcag ctgcagtgtt ggcgactatt      5520
gtaaaattct ctttgtttct ctctgtaaat agcacctgct aacattacaa tttgtattta    5580
tgtttaaaga aggcatcatt tggtgaacag aactaggaaa tgaattttta gctcttaaaa    5640
gcatttgctt tgagaccgca caggagtgtc tttccttgta aaacagtgat gataatttct    5700
gccttggccc taccttgaag caatgttgtg tgaagggatg aagaatctaa aagtcttcat    5760
aagtccttgg gagaggtgct agaaaaatat aaggcactat cataattaca gtgatgtcct    5820
tgctgttact actcaaatca cccacaaatt tccccaaaga ctgcgctagc tgtcaaataa    5880
aagacagtga aattgacctg aaaaaaaaaa aaaaaaa                             5917
```

<210> SEQ ID NO 2
<211> LENGTH: 822
<212> TYPE: PRT
<213> ORGANISM: Homo sapiens

<400> SEQUENCE: 2

-continued

```
Met Trp Ser Trp Lys Cys Leu Leu Phe Trp Ala Val Leu Val Thr Ala
  1               5                  10                 15

Thr Leu Cys Thr Ala Arg Pro Ser Pro Thr Leu Pro Glu Gln Ala Gln
                 20                  25                  30

Pro Trp Gly Ala Pro Val Glu Val Glu Ser Phe Leu Val His Pro Gly
             35                  40                  45

Asp Leu Leu Gln Leu Arg Cys Arg Leu Arg Asp Asp Val Gln Ser Ile
         50                  55                  60

Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
                 85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430
```

-continued

```
Ser Ser Ala Ser Met Asn Ser Gly Val Leu Leu Val Arg Pro Ser Arg
        435                 440                 445
Leu Ser Ser Gly Thr Pro Met Leu Ala Gly Val Ser Glu Tyr Glu
    450                 455                 460
Leu Pro Glu Asp Pro Arg Trp Glu Leu Pro Arg Asp Arg Leu Val Leu
465                 470                 475                 480
Gly Lys Pro Leu Gly Glu Gly Cys Phe Gly Gln Val Val Leu Ala Glu
                485                 490                 495
Ala Ile Gly Leu Asp Lys Asp Lys Pro Asn Arg Val Thr Lys Val Ala
                500                 505                 510
Val Lys Met Leu Lys Ser Asp Ala Thr Glu Lys Asp Leu Ser Asp Leu
            515                 520                 525
Ile Ser Glu Met Glu Met Met Lys Met Ile Gly Lys His Lys Asn Ile
            530                 535                 540
Ile Asn Leu Leu Gly Ala Cys Thr Gln Asp Gly Pro Leu Tyr Val Ile
545                 550                 555                 560
Val Glu Tyr Ala Ser Lys Gly Asn Leu Arg Glu Tyr Leu Gln Ala Arg
                565                 570                 575
Arg Pro Pro Gly Leu Glu Tyr Cys Tyr Asn Pro Ser His Asn Pro Glu
                580                 585                 590
Glu Gln Leu Ser Ser Lys Asp Leu Val Ser Cys Ala Tyr Gln Val Ala
            595                 600                 605
Arg Gly Met Glu Tyr Leu Ala Ser Lys Lys Cys Ile His Arg Asp Leu
            610                 615                 620
Ala Ala Arg Asn Val Leu Val Thr Glu Asp Asn Val Met Lys Ile Ala
625                 630                 635                 640
Asp Phe Gly Leu Ala Arg Asp Ile His His Ile Asp Tyr Tyr Lys Lys
                645                 650                 655
Thr Thr Asn Gly Arg Leu Pro Val Lys Trp Met Ala Pro Glu Ala Leu
            660                 665                 670
Phe Asp Arg Ile Tyr Thr His Gln Ser Asp Val Trp Ser Phe Gly Val
            675                 680                 685
Leu Leu Trp Glu Ile Phe Thr Leu Gly Gly Ser Pro Tyr Pro Gly Val
        690                 695                 700
Pro Val Glu Glu Leu Phe Lys Leu Leu Lys Glu Gly His Arg Met Asp
705                 710                 715                 720
Lys Pro Ser Asn Cys Thr Asn Glu Leu Tyr Met Met Met Arg Asp Cys
                725                 730                 735
Trp His Ala Val Pro Ser Gln Arg Pro Thr Phe Lys Gln Leu Val Glu
            740                 745                 750
Asp Leu Asp Arg Ile Val Ala Leu Thr Ser Asn Gln Glu Tyr Leu Asp
            755                 760                 765
Leu Ser Met Pro Leu Asp Gln Tyr Ser Pro Ser Phe Pro Asp Thr Arg
        770                 775                 780
Ser Ser Thr Cys Ser Ser Gly Glu Asp Ser Val Phe Ser His Glu Pro
785                 790                 795                 800
Leu Pro Glu Glu Pro Cys Leu Pro Arg His Pro Ala Gln Leu Ala Asn
                805                 810                 815
Gly Gly Leu Lys Arg Arg
                820

<210> SEQ ID NO 3
<211> LENGTH: 4654
<212> TYPE: DNA
```

<213> ORGANISM: Homo sapiens

<400> SEQUENCE: 3

| | | | | | | |
|---|---|---|---|---|---|---|
| ggcggcggct | ggaggagagc | gcggtggaga | gccgagcggg | cgggcggcgg | gtgcggagcg | 60 |
| ggcgagggag | cgcgcgcggc | cgccacaaag | ctcgggcgcc | gcggggctgc | atgcggcgta | 120 |
| cctggcccgg | cgcggcgact | gctctccggg | ctggcggggg | ccggccgcga | gccccggggg | 180 |
| ccccgaggcc | gcagcttgcc | tgcgcgctct | gagccttcgc | aactcgcgag | caaagtttgg | 240 |
| tggaggcaac | gccaagcctg | agtcctttct | tcctctcgtt | ccccaaatcc | gagggcagcc | 300 |
| cgcgggcgtc | atgcccgcgc | tcctccgcag | cctggggtac | gcgtgaagcc | cgggaggctt | 360 |
| ggcgccggcg | aagacccaag | gaccactctt | ctgcgtttgg | agttgctccc | cgcaaccccg | 420 |
| ggctcgtcgc | tttctccatc | ccgacccacg | cggggcgcgg | ggacaacaca | ggtcgcggag | 480 |
| gagcgttgcc | attcaagtga | ctgcagcagc | agcggcagcg | cctcggttcc | tgagcccacc | 540 |
| gcaggctgaa | ggcattgcgc | gtagtccatg | cccgtagagg | aagtgtgcag | atgggattaa | 600 |
| cgtccacatg | gagatatgga | agaggaccgg | ggattggtac | cgtaaccatg | gtcagctggg | 660 |
| gtcgtttcat | ctgcctggtc | gtggtcacca | tggcaacctt | gtccctggcc | cggccctcct | 720 |
| tcagtttagt | tgaggatacc | acattagagc | cagaagagcc | accaaccaaa | taccaaatct | 780 |
| ctcaaccaga | agtgtacgtg | gctgcgccag | gggagtcgct | agaggtgcgc | tgcctgttga | 840 |
| aagatgccgc | cgtgatcagt | tggactaagg | atggggtgca | cttggggccc | aacaatagga | 900 |
| cagtgcttat | tggggagtac | ttgcagataa | agggcgccac | gcctagagac | tccggcctct | 960 |
| atgcttgtac | tgccagtagg | actgtagaca | gtgaaacttg | gtacttcatg | gtgaatgtca | 1020 |
| cagatgccat | ctcatccgga | gatgatgagg | atgacaccga | tggtgcggaa | gattttgtca | 1080 |
| gtgagaacag | taacaacaag | agagcaccat | actggaccaa | cacagaaaag | atggaaaagc | 1140 |
| ggctccatgc | tgtgcctgcg | gccaacactg | tcaagtttcg | ctgcccagcc | gggggggaacc | 1200 |
| caatgccaac | catgcggtgg | ctgaaaaacg | ggaaggagtt | taagcaggag | catcgcattg | 1260 |
| gaggctacaa | ggtacgaaac | cagcactgga | gcctcattat | ggaaagtgtg | gtcccatctg | 1320 |
| acaagggaaa | ttatacctgt | gtagtggaga | atgaatacgg | gtccatcaat | cacacgtacc | 1380 |
| acctggatgt | tgtggagcga | tcgcctcacc | ggcccatcct | ccaagccgga | ctgccggcaa | 1440 |
| atgcctccac | agtggtcgga | ggagacgtag | agtttgtctg | caaggtttac | agtgatgccc | 1500 |
| agccccacat | ccagtggatc | aagcacgtgg | aaaagaacgg | cagtaaatac | gggcccgacg | 1560 |
| ggctgccccta | cctcaaggtt | ctcaaggccg | ccggtgttaa | caccacggac | aaagagattg | 1620 |
| aggttctcta | tattcggaat | gtaacttttg | aggacgctgg | ggaatatacg | tgcttggcgg | 1680 |
| gtaattctat | tgggatatcc | tttcactctg | catggttgac | agttctgcca | gcgcctggaa | 1740 |
| gagaaaagga | gattacagct | tccccagact | acctggagat | agccatttac | tgcataggg | 1800 |
| tcttcttaat | cgcctgtatg | gtggtaacag | tcatcctgtg | ccgaatgaag | aacacgacca | 1860 |
| agaagccaga | cttcagcagc | agccggctg | tgcacaagct | gaccaaacgt | atccccctgc | 1920 |
| ggagacaggt | aacagtttcg | gctgagtcca | gctcctccat | gaactccaac | accccgctgg | 1980 |
| tgaggataac | aacacgcctc | tcttcaacgg | cagacacccc | catgctggca | ggggtctccg | 2040 |
| agtatgaact | tccagaggac | ccaaaatggg | agtttccaag | agataagctg | acactgggca | 2100 |
| agcccctggg | agaaggttgc | tttgggcaag | tggtcatggc | ggaagcagtg | ggaattgaca | 2160 |
| aagcaagcc | caaggaggcg | gtcaccgtgg | ccgtgaagat | gttgaaagat | gatgccacag | 2220 |
| agaaagacct | ttctgatctg | gtgtcagaga | tggagatgat | gaagatgatt | gggaaacaca | 2280 |

```
agaatatcat aaatcttctt ggagcctgca cacaggatgg gcctctctat gtcatagttg    2340
agtatgcctc taaaggcaac ctccgagaat acctccgagc ccggaggcca cccgggatgg    2400
agtactccta tgacattaac cgtgttcctg aggagcagat gaccttcaag gacttggtgt    2460
catgcaccta ccagctggcc agaggcatgg agtacttggc ttcccaaaaa tgtattcatc    2520
gagatttagc agccagaaat gttttggtaa cagaaaacaa tgtgatgaaa atagcagact    2580
ttggactcgc cagagatatc aacaatatag actattacaa aaagaccacc aatgggcggc    2640
ttccagtcaa gtggatggct ccagaagccc tgtttgatag agtatacact catcagagtg    2700
atgtctggtc cttcggggtg ttaatgtggg agatcttcac tttaggggc tcgccctacc     2760 cagggattcc cgtggaggaa cttttttaagc tgctgaagga aggacacaga atggataagc    2820
cagccaactg caccaacgaa ctgtacatga tgatgaggga ctgttggcat gcagtgccct    2880
cccagagacc aacgttcaag cagttggtag aagacttgga tcgaattctc actctcacaa    2940
ccaatgagga atacttggac ctcagccaac ctctcgaaca gtattcacct agttaccctg    3000
acacaagaag ttcttgttct tcaggagatg attctgtttt ttctccagac cccatgcctt    3060
acgaaccatg ccttcctcag tatccacaca taaacggcag tgttaaaaca tgaatgactg    3120
tgtctgcctg tccccaaaca ggacagcact gggaacctag ctacactgag cagggagacc    3180
atgcctccca gagcttgttg tctccacttg tatatatgga tcagaggagt aaataattgg    3240
aaaagtaatc agcatatgtg taaagattta tacagttgaa aacttgtaat cttccccagg    3300
aggagaagaa ggtttctgga gcagtggact gccacaagcc accatgtaac ccctctcacc    3360
tgccgtgcgt actggctgtg gaccagtagg actcaaggtg gacgtgcgtt ctgccttcct    3420
tgttaatttt gtaataattg gagaagattt atgtcagcac acacttacag agcacaaatg    3480
cagtatatag gtgctggatg tatgtaaata tattcaaatt atgtataaat atatattata    3540
tatttacaag gagttatttt ttgtattgat tttaaatgga tgtcccaatg cacctagaaa    3600
attggtctct cttttttttaa tagctatttg ctaaatgctg ttcttacaca taatttctta    3660
attttcaccg agcagaggtg gaaaaatact tttgctttca gggaaaatgg tataacgtta    3720
atttattaat aaaattggtaa tatacaaaac aattaatcat ttatagtttt ttttgtaatt    3780
taagtggcat ttctatgcag gcagcacagc agactagtta atctattgct tggacttaac    3840
tagttatcag atcctttgaa aagagaatat ttacaatata tgactaattt ggggaaaatg    3900
aagttttgat ttatttgtgt ttaaatgctg ctgtcagacg attgttctta gacctcctaa    3960
atgccccata ttaaaagaac tcattcatag gaaggtgttt cattttggtg tgcaaccctg    4020
tcattacgtc aacgcaacgt ctaactggac ttcccaagat aaatggtacc agcgtcctct    4080
taaaagatgc cttaatccat tccttgagga cagaccttag ttgaaatgat agcagaatgt    4140
gcttctctct ggcagctggc cttctgcttc tgagttgcac attaatcaga ttagcctgta    4200
ttctcttcag tgaattttga taatggcttc cagactcttt ggcgttggag acgcctgtta    4260
ggatcttcaa gtcccatcat agaaaattga acacagagt tgttctgctg atagttttgg     4320
ggatacgtcc atctttttaa gggattgctt tcatctaatt ctggcaggac ctcaccaaaa    4380
gatccagcct catacctaca tcagacaaaa tatcgccgtt gttccttctg tactaaagta    4440
ttgtgttttg ctttggaaac acccactcac tttgcaatag ccgtgcaaga tgaatgcaga    4500
ttacactgat cttatgtgtt acaaaattgg agaaagtatt taataaaacc tgttaatttt    4560
tatactgaca ataaaaatgt ttctacagat attaatgtta acaagacaaa ataaatgtca    4620
cgcaacttat ttttttaata aaaaaaaaaa aaaa                                4654
```

```
<210> SEQ ID NO 4
<211> LENGTH: 840
<212> TYPE: PRT
<213> ORGANISM: Homo sapiens

<400> SEQUENCE: 4

Met Gly Leu Thr Ser Thr Trp Arg Tyr Gly Arg Gly Pro Gly Ile Gly
  1               5                  10                  15

Thr Val Thr Met Val Ser Trp Gly Arg Phe Ile Cys Leu Val Val
             20                  25                  30

Thr Met Ala Thr Leu Ser Leu Ala Arg Pro Ser Phe Ser Leu Val Glu
             35                  40                  45

Asp Thr Thr Leu Glu Pro Glu Pro Pro Thr Lys Tyr Gln Ile Ser
 50                  55                  60

Gln Pro Glu Val Tyr Val Ala Ala Pro Gly Glu Ser Leu Glu Val Arg
 65                  70                  75                  80

Cys Leu Leu Lys Asp Ala Ala Val Ile Ser Trp Thr Lys Asp Gly Val
                 85                  90                  95

His Leu Gly Pro Asn Asn Arg Thr Val Leu Ile Gly Glu Tyr Leu Gln
                100                 105                 110

Ile Lys Gly Ala Thr Pro Arg Asp Ser Gly Leu Tyr Ala Cys Thr Ala
                115                 120                 125

Ser Arg Thr Val Asp Ser Glu Thr Trp Tyr Phe Met Val Asn Val Thr
130                 135                 140

Asp Ala Ile Ser Ser Gly Asp Asp Glu Asp Thr Asp Gly Ala Glu
145                 150                 155                 160

Asp Phe Val Ser Glu Asn Ser Asn Asn Lys Arg Ala Pro Tyr Trp Thr
                165                 170                 175

Asn Thr Glu Lys Met Glu Lys Arg Leu His Ala Val Pro Ala Ala Asn
                180                 185                 190

Thr Val Lys Phe Arg Cys Pro Ala Gly Gly Asn Pro Met Pro Thr Met
                195                 200                 205

Arg Trp Leu Lys Asn Gly Lys Glu Phe Lys Gln Glu His Arg Ile Gly
210                 215                 220

Gly Tyr Lys Val Arg Asn Gln His Trp Ser Leu Ile Met Glu Ser Val
225                 230                 235                 240

Val Pro Ser Asp Lys Gly Asn Tyr Thr Cys Val Val Glu Asn Glu Tyr
                245                 250                 255

Gly Ser Ile Asn His Thr Tyr His Leu Asp Val Val Glu Arg Ser Pro
                260                 265                 270

His Arg Pro Ile Leu Gln Ala Gly Leu Pro Ala Asn Ala Ser Thr Val
                275                 280                 285

Val Gly Gly Asp Val Glu Phe Val Cys Lys Val Tyr Ser Asp Ala Gln
290                 295                 300

Pro His Ile Gln Trp Ile Lys His Val Glu Lys Asn Gly Ser Lys Tyr
305                 310                 315                 320

Gly Pro Asp Gly Leu Pro Tyr Leu Lys Val Leu Lys Ala Ala Gly Val
                325                 330                 335

Asn Thr Thr Asp Lys Glu Ile Glu Val Leu Tyr Ile Arg Asn Val Thr
                340                 345                 350

Phe Glu Asp Ala Gly Glu Tyr Thr Cys Leu Ala Gly Asn Ser Ile Gly
                355                 360                 365

Ile Ser Phe His Ser Ala Trp Leu Thr Val Leu Pro Ala Pro Gly Arg
370                 375                 380
```

```
Glu Lys Glu Ile Thr Ala Ser Pro Asp Tyr Leu Glu Ile Ala Ile Tyr
385                 390                 395                 400

Cys Ile Gly Val Phe Leu Ile Ala Cys Met Val Val Thr Val Ile Leu
            405                 410                 415

Cys Arg Met Lys Asn Thr Thr Lys Lys Pro Asp Phe Ser Ser Gln Pro
        420                 425                 430

Ala Val His Lys Leu Thr Lys Arg Ile Pro Leu Arg Arg Gln Val Thr
    435                 440                 445

Val Ser Ala Glu Ser Ser Ser Met Asn Ser Asn Thr Pro Leu Val
450                 455                 460

Arg Ile Thr Thr Arg Leu Ser Ser Thr Ala Asp Thr Pro Met Leu Ala
465                 470                 475                 480

Gly Val Ser Glu Tyr Glu Leu Pro Glu Asp Pro Lys Trp Glu Phe Pro
                485                 490                 495

Arg Asp Lys Leu Thr Leu Gly Lys Pro Leu Gly Glu Gly Cys Phe Gly
            500                 505                 510

Gln Val Val Met Ala Glu Ala Val Gly Ile Asp Lys Asp Lys Pro Lys
        515                 520                 525

Glu Ala Val Thr Val Ala Val Lys Met Leu Lys Asp Asp Ala Thr Glu
530                 535                 540

Lys Asp Leu Ser Asp Leu Val Ser Glu Met Glu Met Met Lys Met Ile
545                 550                 555                 560

Gly Lys His Lys Asn Ile Ile Asn Leu Leu Gly Ala Cys Thr Gln Asp
                565                 570                 575

Gly Pro Leu Tyr Val Ile Val Glu Tyr Ala Ser Lys Gly Asn Leu Arg
            580                 585                 590

Glu Tyr Leu Arg Ala Arg Arg Pro Pro Gly Met Glu Tyr Ser Tyr Asp
        595                 600                 605

Ile Asn Arg Val Pro Glu Glu Gln Met Thr Phe Lys Asp Leu Val Ser
    610                 615                 620

Cys Thr Tyr Gln Leu Ala Arg Gly Met Glu Tyr Leu Ala Ser Gln Lys
625                 630                 635                 640

Cys Ile His Arg Asp Leu Ala Ala Arg Asn Val Leu Val Thr Glu Asn
                645                 650                 655

Asn Val Met Lys Ile Ala Asp Phe Gly Leu Ala Arg Asp Ile Asn Asn
            660                 665                 670

Ile Asp Tyr Tyr Lys Lys Thr Thr Asn Gly Arg Leu Pro Val Lys Trp
        675                 680                 685

Met Ala Pro Glu Ala Leu Phe Asp Arg Val Tyr Thr His Gln Ser Asp
    690                 695                 700

Val Trp Ser Phe Gly Val Leu Met Trp Glu Ile Phe Thr Leu Gly Gly
705                 710                 715                 720

Ser Pro Tyr Pro Gly Ile Pro Val Glu Glu Leu Phe Lys Leu Leu Lys
                725                 730                 735

Glu Gly His Arg Met Asp Lys Pro Ala Asn Cys Thr Asn Glu Leu Tyr
            740                 745                 750

Met Met Met Arg Asp Cys Trp His Ala Val Pro Ser Gln Arg Pro Thr
        755                 760                 765

Phe Lys Gln Leu Val Glu Asp Leu Asp Arg Ile Leu Thr Leu Thr Thr
    770                 775                 780

Asn Glu Glu Tyr Leu Asp Leu Ser Gln Pro Leu Glu Gln Tyr Ser Pro
785                 790                 795                 800

Ser Tyr Pro Asp Thr Arg Ser Ser Cys Ser Ser Gly Asp Asp Ser Val
                805                 810                 815
```

Phe Ser Pro Asp Pro Met Pro Tyr Glu Pro Cys Leu Pro Gln Tyr Pro
            820                 825                 830

His Ile Asn Gly Ser Val Lys Thr
            835                 840

<210> SEQ ID NO 5
<211> LENGTH: 3829
<212> TYPE: DNA
<213> ORGANISM: Homo sapiens

<400> SEQUENCE: 5

```
aaggatggca cagggctggt gccctcggag cgtgtcctgg tggggcccca gcggctgcag    60
gtgctgaatg cctcccacga ggactccggg gcctacagct gccggcagcg gctcacgcag   120
cgcgtactgt gccacttcag tgtgcgggtg acagacgctc catcctcggg agatgacgaa   180
gacggggagg acgaggctga ggacacaggt gtggacacag gggcccctta ctggacacgg   240
cccgagcgga tggacaagaa gctgctggcc gtgccggccg ccaacaccgt ccgcttccgc   300
tgcccagccg ctggcaaccc cactccctcc atctcctggc tgaagaacgg cagggagttc   360
cgcggcgagc accgcattgg aggcatcaag ctgcggcatc agcagtggag cctggtcatg   420
gaaagcgtgg tgccctcgga ccgcggcaac tacacctgcg tcgtggagaa caagtttggc   480
agcatccgga gacgtacac gctggacgtg ctggagcgct cccgcaccg gcccatcctg   540
caggcggggc tgccggccaa ccagacggcg gtgctgggca cgacgtgga gttccactgc   600
aaggtgtaca gtgacgcaca gccccacatc cagtggctca gcacgtgga ggtgaatggc   660
agcaaggtgg gcccggacgg cacaccctac gttaccgtgc tcaagacggc gggcgctaac   720
accaccgaca aggagctaga ggttctctcc ttgcacaacg tcacctttga ggacgccggg   780
gagtacacct gcctggcggg caattctatt gggttttctc atcactctgc gtggctggtg   840
gtgctgccag ccgaggagga gctggtggag gctgacgagg cggcagtgt gtatgcaggc   900
atcctcagct acggggtggg cttcttcctg ttcatcctgg tggtggcggc tgtgaccgtc   960
tgccgcctgc gcagcccccc caagaaaggc ctgggctccc ccaccgtgca caagatctcc  1020
cgcttcccgc tcaagcgaca ggtgtccctg gagtccaacg cgtccatgag ctccaacaca  1080
ccactggtgc gcatcgcaag gctgtcctca ggggagggcc ccacgctggc caatgtctcc  1140
gagctcgagc tgcctgccga ccccaaatgg gagctgtctc gggcccggct gaccctgggc  1200
aagcccttg ggagggctg cttcggccag gtggtcatgg cggaggccat cggcattgac  1260
aaggaccggg ccgccaagcc tgtcaccgta gccgtgaaga tgctgaaaga cgatgccact  1320
gacaaggacc tgtcggacct ggtgtctgag atggagatga tgaagatgat cgggaaacac  1380
aaaaacatca tcaacctgct gggcgcctgc acgcagggcg ggcccctgta cgtgctggtg  1440
gagtacgcgg ccaagggtaa cctgcgggag tttctgcggg cgcggcgcc ccgggcctg  1500
gactactcct tcgacacctg caagccgccc gaggagcagc tcaccttcaa ggacctggtg  1560
tcctgtgcct accaggtggc ccggggcatg gagtacttgg cctcccagaa gtgcatccac  1620
agggacctgc tgcccgcaa tgtgctggtg accgaggaca cgtgatgaa gatcgcagac  1680
ttcgggctgg cccgggacgt gcacaacctc gactactaca agaagacaac caacggccgg  1740
ctccccgtga gtggatggc gcctgaggcc ttgtttgacc gagtctacac tcaccagagt  1800
gacgtctggt cctttggggt cctgctctgg gagatcttca cgctgggggg ctccccgtac  1860
cccggcatcc ctgtgaagga gctcttcaag ctgctgaagg agggccaccg catggacaag  1920
cccgccaact gcacacacga cctgtacatg atcatgcggg agtgctggca tgccgcgccc  1980
```

-continued

```
tcccagaggc ccaccttcaa gcagctggtg gaggacctgg accgtgtcct taccgtgacg   2040
tccaccgacg agtacctgga cctgtcggcg cctttcgagc agtactcccc gggtggccag   2100 gacacccca gctccagctc ctcaggggac gactccgtgt ttgcccacga cctgctgccc    2160 ccggcccac ccagcagtgg gggctcgcgg acgtgaaggg ccactggtcc ccaacaatgt    2220
gaggggtccc tagcagccca ccctgctgct ggtgcacagc cactccccgg catgagactc   2280
agtgcagatg gagagacagc tacacagagc tttggtctgt gtgtgtgtgt gtgcgtgtgt   2340
gtgtgtgtgt gcacatccgc gtgtgcctgt gtgcgtgcgc atcttgcctc caggtgcaga   2400
ggtaccctgg gtgtccccgc tgctgtgcaa cggtctcctg actggtgctg cagcaccgag   2460
gggcctttgt tctgggggga cccagtgcag aatgtaagtg ggcccacccg gtgggacccc   2520
gtggggcagg gagctgggcc cgacatggct cggcctctgc ctttgcacca cggacatca    2580 cagggtgcgc tcggccctc ccacacccaa agctgagcct gcagggaagc cccacatgtc    2640
cagcaccttg tgcctggggt gttagtggca ccgcctcccc acctccaggc tttcccactt   2700
cccaccctgc ccctcagaga ctgaaattac gggtacctga agatgggagc ctttaccttt   2760
tatgcaaaag gtttattccg gaaactagtg tacatttcta taaatagatg ctgtgtatat   2820
ggtatatata catatatata tataacatat atggaagagg aaaaggctgg tacaacggag   2880
gcctgcgacc ctgggggcac aggaggcagg catggccctg gcggggcgt gggggggcgt    2940 ggagggaggc cccaggggtc tcacccatgc aagcagagga ccagggcttt tctggcacc    3000 gcagttttgt tttaaaactg gacctgtata tttgtaaagc tatttatggg ccctggcac    3060 tcttgttccc acaccccaac acttccagca tttagctggc cacatggcgg agagttttaa   3120 ttttaactt attgacaacc gagaaggttt atcccgccga tagagggacg gccaagaatg    3180
tacgtccagc ctgccccgga gctggaggat cccctccaag cctaaaaggt tgttaatagt    3240
tggaggtgat tccagtgaag atattttatt tgctttgtcc tttttcagga gaattagatt    3300
tctataggat ttttctttag gagatttatt ttttggactt caaagcaagc tggtatttc    3360 atacaaattc ttctaattgc tgtgtgtccc aggcagggag acggtttcca gggaggggcc    3420
ggccctgtgt gcaggttccg atgttattag atgttacaag tttatatata tctatatata   3480
taatttattg agttttaca agatgtattt gttgtagact taacacttct tacgcaatgc    3540
ttctagagtt ttatagcctg gactgctacc tttcaaagct tggagggaag ccgtgaattc   3600
agttggttcg ttctgtactg ttactgggcc ctgagtctgg gcagctgtcc cttgcttgcc   3660
tgcagggcca tggctcaggg tggtctcttc ttggggccca gtgcatggtg gccagaggtg   3720
tcacccaaac cggcaggtgc gattttgtta acccagcgac gaactttccg aaaaataaag   3780
acacctggtt gctaacctga aaaaaaaaa aaaaaaaaa aaaaaaaa                   3829
```

<210> SEQ ID NO 6
<211> LENGTH: 806
<212> TYPE: PRT
<213> ORGANISM: Homo sapiens

<400> SEQUENCE: 6

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

```
Leu Val Phe Gly Ser Gly Asp Ala Val Glu Leu Ser Cys Pro Pro Pro
     50                  55                  60

Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Ala Glu Asp Thr
            130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
            210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
            450                 455                 460

Trp Glu Leu Ser Arg Ala Arg Leu Thr Leu Gly Lys Pro Leu Gly Glu
465                 470                 475                 480
```

| | | | | | | | | | | | | |
|---|---|---|---|---|---|---|---|---|---|---|---|---|
|Gly|Cys|Phe|Gly|Gln|Val|Val|Met|Ala|Glu|Ala|Ile|Gly|Ile|Asp|Lys|
| | | |485| | | |490| | | |495| |

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
        500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
        530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
            565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
        610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
            645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
        690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
            725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
            755                 760                 765

Gln Tyr Ser Pro Gly Gly Gln Asp Thr Pro Ser Ser Ser Ser Ser Gly
        770                 775                 780

Asp Asp Ser Val Phe Ala His Asp Leu Leu Pro Pro Ala Pro Pro Ser
785                 790                 795                 800

Ser Gly Gly Ser Arg Thr
            805

<210> SEQ ID NO 7
<211> LENGTH: 3040
<212> TYPE: DNA
<213> ORGANISM: Homo sapiens

<400> SEQUENCE: 7

```
ctcgctcccg gccgaggagc gctcgggctg tctgcggacc ctgccgcgtg caggggtcgc      60
ggccggctgg agctgggagt gaggcggcgg aggagccagg tgaggaggag ccaggaaggc     120
agttggtggg aagtccagct tgggtccctg agagctgtga gaggagatg cggctgctgc     180 tggccctgtt gggggtcctg ctgagtgtgc ctgggcctcc agtcttgtcc ctggaggcct     240
```

```
ctgaggaagt ggagcttgag ccctgcctgg ctcccagcct ggagcagcaa gagcaggagc    300
tgacagtagc ccttgggcag cctgtgcgtc tgtgctgtgg gcgggctgag cgtggtggcc    360
actggtacaa ggagggcagt cgcctggcac ctgctggccg tgtacggggc tggaggggcc    420
gcctagagat tgccagcttc ctacctgagg atgctggccg ctacctctgc ctggcacgag    480
gctccatgat cgtcctgcag aatctcacct tgattacagg tgactccttg acctccagca    540
acgatgatga ggaccccaag tcccataggg acccctcgaa taggcacagt tacccccagc    600
aagcacccta ctggacacac ccccagcgca tggagaagaa actgcatgca gtacctgcgg    660
ggaacaccgt caagttccgc tgtccagctg caggcaaccc cacgcccacc atccgctggc    720
ttaaggatgg acaggccttt catggggaga accgcattgg aggcattcgg ctgcgccatc    780
agcactggag tctcgtgatg gagagcgtgg tgccctcgga ccgcggcaca tacacctgcc    840
tggtagagaa cgctgtgggc agcatccgct ataactacct gctagatgtg ctggagcggt    900
ccccgcaccg gccatcctg caggccgggc tcccggccaa caccacagcc gtggtgggca    960
gcgacgtgga gctgctgtgc aaggtgtaca gcgatgccca gccccacatc cagtggctga   1020
agcacatcgt catcaacggc agcagcttcg gagccgacgg tttcccctat gtgcaagtcc   1080
taaagactgc agacatcaat agctcagagg tggaggtcct gtacctgcgg aacgtgtcag   1140
ccgaggacgc aggcgagtac acctgcctcg caggcaattc catcggcctc tcctaccagt   1200
ctgcctggct cacggtgctg ccagaggagg accccacatg gaccgcagca gcgcccgagg   1260
ccaggtatac ggacatcatc ctgtacgcgt cgggctccct ggccttggct gtgctcctgc   1320
tgctggccgg gctgtatcga gggcaggcgc tccacggccg gcaccccgc ccgcccgcca   1380 ctgtgcagaa gctctcccgc ttccctctgg cccgacagtt ctccctggag tcaggctctt   1440
ccggcaagtc aagctcatcc ctggtacgag gcgtgcgtct ctcctccagc ggccccgcct   1500
tgctcgccgg cctcgtgagt ctagatctac ctctcgaccc actatgggag ttcccccggg   1560
acaggctggt gcttgggaag cccctaggcg agggctgctt tggccaggta gtacgtgcag   1620
aggcctttgg catggaccct gcccggcctg accaagccag cactgtggcc gtcaagatgc   1680
tcaaagacaa cgcctctgac aaggacctgg ccgacctggt ctcggagatg gaggtgatga   1740
agctgatcgg ccgacacaag aacatcatca acctgcttgg tgtctgcacc caggaagggc   1800
ccctgtacgt gatcgtggag tgcgccgcca agggaaacct gcgggagttc ctgcgggccc   1860 ggcgccccc aggccccgac ctcagccccg acggtcctcg gagcagtgag gggccgctct   1920
ccttcccagt cctggtctcc tgcgcctacc aggtggcccg aggcatgcag tatctggagt   1980
cccggaagtg tatccaccgg gacctggctg ccgcaatgt gctggtgact gaggacaatg   2040
tgatgaagat tgctgacttt gggctggccc gcggcgtcca ccacattgac tactataaga   2100
aaaccagcaa cggccgcctg cctgtgaagt ggatggcgcc cgaggccttg tttgaccggg   2160
tgtacacaca ccagagtgac gtgtggtctt ttgggatcct gctatgggag atcttcaccc   2220 tcggggctc cccgtatcct ggcatccgg tggaggagct gttctcgctg ctgcgggagg   2280
gacatcggat ggaccgaccc ccacactgcc ccccagagct gtacgggctg atgcgtgagt   2340
gctggcacgc agcgccctcc cagaggccta ccttcaagca gctggtggag gcgctggaca   2400
aggtcctgct ggccgtctct gaggagtacc tcgacctccg cctgaccttc ggaccctatt   2460 cccccctctgg tggggacgcc agcagcacct gctcctccag cgattctgtc ttcagccacg   2520
accccctgcc attgggatcc agctccttcc ccttcgggtc tggggtgcag acatgagcaa   2580
ggctcaaggc tgtgcaggca cataggctgg tggccttggg ccttggggct cagccacagc   2640
```

-continued

```
ctgacacagt gctcgacctt gatagcatgg ggccctggc ccagagttgc tgtgccgtgt    2700
ccaagggccg tgcccttgcc cttggagctg ccgtgcctgt gtcctgatgg cccaaatgtc    2760
agggttctgc tcggcttctt ggaccttggc gcttagtccc catcccgggt ttggctgagc    2820
ctggctggag agctgctatg ctaaacctcc tgcctcccaa taccagcagg aggttctggg    2880
cctctgaacc ccctttcccc acacctcccc ctgctgctgc tgcccagcg tcttgacggg    2940 agcattggcc cctgagccca gagaagctgg aagcctgccg aaaacaggag caaatggcgt    3000
tttataaatt atttttttga aataaaaaaa aaaaaaaaa                          3040
```

<210> SEQ ID NO 8
<211> LENGTH: 802
<212> TYPE: PRT
<213> ORGANISM: Homo sapiens

<400> SEQUENCE: 8

```
Met Arg Leu Leu Leu Ala Leu Leu Gly Val Leu Leu Ser Val Pro Gly
  1               5                  10                  15

Pro Pro Val Leu Ser Leu Glu Ala Ser Glu Glu Val Glu Leu Glu Pro
             20                  25                  30

Cys Leu Ala Pro Ser Leu Glu Gln Gln Glu Gln Glu Leu Thr Val Ala
         35                  40                  45

Leu Gly Gln Pro Val Arg Leu Cys Cys Gly Arg Ala Glu Arg Gly Gly
     50                  55                  60

His Trp Tyr Lys Glu Gly Ser Arg Leu Ala Pro Ala Gly Arg Val Arg
 65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
```

```
            305                 310                 315                 320
Arg Asn Val Ser Ala Glu Asp Ala Gly Glu Tyr Thr Cys Leu Ala Gly
                    325                 330                 335

Asn Ser Ile Gly Leu Ser Tyr Gln Ser Ala Trp Leu Thr Val Leu Pro
                340                 345                 350

Glu Glu Asp Pro Thr Trp Thr Ala Ala Pro Glu Ala Arg Tyr Thr
                355                 360                 365

Asp Ile Ile Leu Tyr Ala Ser Gly Ser Leu Ala Leu Ala Val Leu Leu
            370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
                420                 425                 430

Val Arg Gly Val Arg Leu Ser Ser Gly Pro Ala Leu Leu Ala Gly
                435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
                500                 505                 510

Asp Leu Ala Asp Leu Val Ser Glu Met Glu Val Met Lys Leu Ile Gly
            515                 520                 525

Arg His Lys Asn Ile Ile Asn Leu Leu Gly Val Cys Thr Gln Glu Gly
            530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
            595                 600                 605

Ile His Arg Asp Leu Ala Ala Arg Asn Val Leu Val Thr Glu Asp Asn
        610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
                660                 665                 670

Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
            690                 695                 700

Gly His Arg Met Asp Arg Pro Pro His Cys Pro Glu Leu Tyr Gly
705                 710                 715                 720

Leu Met Arg Glu Cys Trp His Ala Ala Pro Ser Gln Arg Pro Thr Phe
                725                 730                 735
```

```
Lys Gln Leu Val Glu Ala Leu Asp Lys Val Leu Leu Ala Val Ser Glu
                740                 745                 750

Glu Tyr Leu Asp Leu Arg Leu Thr Phe Gly Pro Tyr Ser Pro Ser Gly
                755                 760                 765

Gly Asp Ala Ser Ser Thr Cys Ser Ser Ser Asp Ser Val Phe Ser His
        770                 775                 780

Asp Pro Leu Pro Leu Gly Ser Ser Ser Phe Pro Phe Gly Ser Gly Val
785                 790                 795                 800

Gln Thr

<210> SEQ ID NO 9
<211> LENGTH: 3887
<212> TYPE: DNA
<213> ORGANISM: Homo sapiens

<400> SEQUENCE: 9
```

| | | | | | |
|---|---|---|---|---|---|
| gactgcgcag | gcgtgctcac | ctggcgtgct | ccacccgact | gggcgtccgc | aggctcctcc | 60 |
| cccgggtgtg | gcctccgggc | ggcatggctg | cttcccaggt | gatgccggct | tcagctagtg | 120 |
| gggtctagtt | gaccgttccg | cagccgccag | ggccagcgga | aagccggtca | gggggaaccg | 180 |
| cggcggggct | ggtgtcatga | gcctgaggtg | aacttgaggg | tgcctcctca | gcggtctccc | 240 |
| gccctgccct | gaggggcgcc | gggaccccaa | agagcggagg | aagagcgcca | ccccgacggc | 300 |
| caccgcttcg | gagccagcac | gcggggtacc | ctacggggag | cgcggatgcc | cccgtgttcg | 360 |
| ggcggggacg | gctccacccc | tcctgggccc | tcccttcggg | acagggactg | tcccgcccag | 420 |
| agtgctgaat | acccgcgcga | ccgtctggat | ccccgcccag | gaagcccctc | tgaagcctcc | 480 |
| tcgccgccgt | ttctgagaag | cagggcacct | gttaactggt | accaagaaaa | ggcccaagtg | 540 |
| tttctctggc | atctgatggt | gtctggatcc | accactctac | tctgtctctg | gaaacagccc | 600 |
| ttccacgtct | ctgcattccc | tgtcaccgcg | tcactggcct | tcagacagag | ccaaggtgca | 660 |
| gggcaacacc | tctacaagga | tctgcagcca | tttatattgc | ttaggctact | gatgcctgag | 720 |
| gaaacccaga | cccaagacca | accgatggag | gaggaggagg | ttgagacgtt | cgcctttcag | 780 |
| gcagaaattg | cccagttgat | gtcattgatc | atcaatactt | tctactcgaa | caaagagatc | 840 |
| tttctgagag | agctcatttc | aaattcatca | gatgcattgg | acaaaatccg | gtatgaaagc | 900 |
| ttgacagatc | ccagtaaatt | agactctggg | aaagagctgc | atattaacct | tataccgaac | 960 |
| aaacaagatc | gaactctcac | tattgtggat | actggaattg | gaatgaccaa | ggctgacttg | 1020 |
| atcaataacc | ttggtactat | cgccaagtct | gggaccaaag | cgttcatgga | agctttgcag | 1080 |
| gctggtgcag | atatctctat | gattggccag | ttcggtgttg | gttttattc | tgcttatttg | 1140 |
| gttgctgaga | agtaactgt | gatcaccaaa | cataacgatg | atgagcagta | cgcttgggag | 1200 |
| tcctcagcag | ggggatcatt | cacagtgagg | acagacacag | gtgaacctat | gggtcgtgga | 1260 |
| acaaaagtta | tcctacacct | gaagaagac | caaactgagt | acttggagga | acgaagaata | 1320 |
| aaggagattg | tgaagaaaca | ttctcagttt | attggatatc | ccattactct | ttttgtggag | 1380 |
| aaggaacgtg | ataaagaagt | aagcgatgat | gaggctgaag | aaaaggaaga | caaagaagaa | 1440 |
| gaaaaagaaa | aagaagagaa | agagtcggaa | gacaaacctg | aaattgaaga | tgttggttct | 1500 |
| gatgaggaag | aagaaaagaa | ggatggtgac | aagaagaaga | agaagaagat | taaggaaaag | 1560 |
| tacatcgatc | aagaagagct | caacaaaaca | aagcccatct | ggaccagaaa | tcccgacgat | 1620 |
| attactaatg | aggagtacgg | agaattctat | aagagcttga | ccaatgactg | ggaagatcac | 1680 |
| ttggcagtga | agcatttttc | agttgaagga | cagttggaat | tcagagccct | tctatttgtc | 1740 |

-continued

```
ccacgacgtg ctccttttga tctgtttgaa aacagaaaga aaaagaacaa catcaaattg    1800
tatgtacgca gagttttcat catggataac tgtgaggagc taatccctga atatctgaac    1860
ttcattagag gggtggtaga ctcggaggat ctccctctaa acatatcccg tgagatgttg    1920
caacaaagca aaattttgaa agttatcagg aagaatttgg tcaaaaaatg cttagaactc    1980
tttactgaac tggcggaaga taaagagaac tacaagaaat tctatgagca gttctctaaa    2040
aacataaagc ttggaataca cgaagactct caaaatcgga agaagctttc agagctgtta    2100
aggtactaca catctgcctc tggtgatgag atggtttctc tcaaggacta ctgcaccaga    2160
atgaaggaga accagaaaca tatctattat atcacaggtg agaccaagga ccaggtagct    2220
aactcagcct tgtggaacg tcttcggaaa catggcttag aagtgatcta tatgattgag    2280
cccattgatg agtactgtgt ccaacagctg aaggaatttg aggggaagac tttagtgtca    2340
gtcaccaaag aaggcctgga acttccagag gatgaagaag agaaaaagaa gcaggaagag    2400
aaaaaaacaa agtttgagaa cctctgcaaa atcatgaaag acatattgga gaaaaagtt    2460
gaaaaggtgg ttgtgtcaaa ccgattggtg acatctccat gctgtattgt cacaagcaca    2520
tatggctgga cagcaaacat ggagagaatc atgaaagctc aagccctaag agacaactca    2580
acaatgggtt acatggcagc aaagaaacac ctggagataa accctgacca ttccattatt    2640
gagacccttaa ggcaaaaggc agaggctgat aagaacgaca agtctgtgaa ggatctggtc    2700
atcttgctt atgaaactgc gctcctgtct tctggcttca gtctggaaga tccccagaca    2760
catgctaaca ggatctacag gatgatcaaa cttggtctgg gtattgatga agatgaccct    2820
actgctgatg ataccagtgc tgctgtaact gaagaaatgc caccccttga aggagatgac    2880
gacacatcac gcatggaaga agtagactaa tctctggctg agggatgact tacctgttca    2940
gtactctaca attcctctga taatatattt tcaaggatgt ttttctttat ttttgttaat    3000
attaaaaagt ctgtatggca tgacaactac tttaagggga agataagatt tctgtctact    3060
aagtgatgct gtgataacct aggcactaaa gcagagctag taatgctttt tgagtttcat    3120
gttggtttat tttcacagat tggggtaacg tgcactgtaa gacgtatgta acatgatgtt    3180
aactttgtgg tctaaagtgt ttagctgtca agccggatgc ctaagtagac caaatcttgt    3240
tattgaagtg ttctgagctg tatcttgatg tttagaaaag tattcgttac atcttgtagg    3300
atctactttt tgaactttc attccctgta gttgacaatt ctgcatgtac tagtcctcta    3360
gaaataggtt aaactgaagc aacttgatgg aaggatctct ccacagggct tgttttccaa    3420
agaaagtat tgtttggagg agcaaagtta aagcctacc taagcatatc gtaaagctgt    3480
tcaaaaataa ctcagaccca gtcttgtgga tggaaatgta gtgctcgagt cacattctgc    3540
ttaaagttgt aacaaataca gatgagttaa aagatattgt gtgacagtgt cttatttagg    3600
gggaaagggg agtatctgga tgacagttag tgccaaaatg taaaacatga ggcgctagca    3660
ggagatggtt aaacactagc tgctccaagg gttgacatgg tcttcccagc atgtactcag    3720
caggtgtggg gtggagcaca cgtaggcaca gaaaacagga atgcagacaa catgcatccc    3780
ctgcgtccat gagttacatg tgttctctta gtgtccacgt tgttttgatg ttattcatgg    3840
aataccttct gtgttaaata cagtcactta attccttggc cttaaaa              3887
```

<210> SEQ ID NO 10
<211> LENGTH: 854
<212> TYPE: PRT
<213> ORGANISM: Homo sapiens

<400> SEQUENCE: 10

-continued

```
Met Pro Pro Cys Ser Gly Gly Asp Gly Ser Thr Pro Gly Pro Ser
 1               5                  10                 15

Leu Arg Asp Arg Asp Cys Pro Ala Gln Ser Ala Glu Tyr Pro Arg Asp
                20                  25                  30

Arg Leu Asp Pro Arg Pro Gly Ser Pro Ser Glu Ala Ser Ser Pro Pro
            35                  40                  45

Phe Leu Arg Ser Arg Ala Pro Val Asn Trp Tyr Gln Glu Lys Ala Gln
    50                  55                  60

Val Phe Leu Trp His Leu Met Val Ser Gly Ser Thr Thr Leu Leu Cys
65                  70                  75                  80

Leu Trp Lys Gln Pro Phe His Val Ser Ala Phe Pro Val Thr Ala Ser
                85                  90                  95

Leu Ala Phe Arg Gln Ser Gln Gly Ala Gly Gln His Leu Tyr Lys Asp
            100                 105                 110

Leu Gln Pro Phe Ile Leu Leu Arg Leu Leu Met Pro Glu Glu Thr Gln
        115                 120                 125

Thr Gln Asp Gln Pro Met Glu Glu Glu Val Glu Thr Phe Ala Phe
    130                 135                 140

Gln Ala Glu Ile Ala Gln Leu Met Ser Leu Ile Ile Asn Thr Phe Tyr
145                 150                 155                 160

Ser Asn Lys Glu Ile Phe Leu Arg Glu Leu Ile Ser Asn Ser Ser Asp
                165                 170                 175

Ala Leu Asp Lys Ile Arg Tyr Glu Ser Leu Thr Asp Pro Ser Lys Leu
            180                 185                 190

Asp Ser Gly Lys Glu Leu His Ile Asn Leu Ile Pro Asn Lys Gln Asp
        195                 200                 205

Arg Thr Leu Thr Ile Val Asp Thr Gly Ile Gly Met Thr Lys Ala Asp
210                 215                 220

Leu Ile Asn Asn Leu Gly Thr Ile Ala Lys Ser Gly Thr Lys Ala Phe
225                 230                 235                 240

Met Glu Ala Leu Gln Ala Gly Ala Asp Ile Ser Met Ile Gly Gln Phe
                245                 250                 255

Gly Val Gly Phe Tyr Ser Ala Tyr Leu Val Ala Glu Lys Val Thr Val
            260                 265                 270

Ile Thr Lys His Asn Asp Asp Glu Gln Tyr Ala Trp Glu Ser Ser Ala
        275                 280                 285

Gly Gly Ser Phe Thr Val Arg Thr Asp Thr Gly Glu Pro Met Gly Arg
    290                 295                 300

Gly Thr Lys Val Ile Leu His Leu Lys Glu Asp Gln Thr Glu Tyr Leu
305                 310                 315                 320

Glu Glu Arg Arg Ile Lys Glu Ile Val Lys Lys His Ser Gln Phe Ile
                325                 330                 335

Gly Tyr Pro Ile Thr Leu Phe Val Glu Lys Glu Arg Asp Lys Glu Val
            340                 345                 350

Ser Asp Asp Glu Ala Glu Glu Lys Glu Asp Lys Glu Glu Lys Glu
        355                 360                 365

Lys Glu Glu Lys Glu Ser Glu Asp Lys Pro Glu Ile Glu Asp Val Gly
    370                 375                 380

Ser Asp Glu Glu Glu Glu Lys Lys Asp Gly Asp Lys Lys Lys Lys
385                 390                 395                 400

Lys Ile Lys Glu Lys Tyr Ile Asp Gln Glu Glu Leu Asn Lys Thr Lys
                405                 410                 415

Pro Ile Trp Thr Arg Asn Pro Asp Asp Ile Thr Asn Glu Glu Tyr Gly
            420                 425                 430
```

```
Glu Phe Tyr Lys Ser Leu Thr Asn Asp Trp Glu Asp His Leu Ala Val
            435                 440                 445

Lys His Phe Ser Val Glu Gly Gln Leu Glu Phe Arg Ala Leu Leu Phe
450                 455                 460

Val Pro Arg Arg Ala Pro Phe Asp Leu Phe Glu Asn Arg Lys Lys Lys
465                 470                 475                 480

Asn Asn Ile Lys Leu Tyr Val Arg Arg Val Phe Ile Met Asp Asn Cys
                485                 490                 495

Glu Glu Leu Ile Pro Glu Tyr Leu Asn Phe Ile Arg Gly Val Val Asp
            500                 505                 510

Ser Glu Asp Leu Pro Leu Asn Ile Ser Arg Glu Met Leu Gln Gln Ser
        515                 520                 525

Lys Ile Leu Lys Val Ile Arg Lys Asn Leu Val Lys Lys Cys Leu Glu
530                 535                 540

Leu Phe Thr Glu Leu Ala Glu Asp Lys Glu Asn Tyr Lys Lys Phe Tyr
545                 550                 555                 560

Glu Gln Phe Ser Lys Asn Ile Lys Leu Gly Ile His Glu Asp Ser Gln
                565                 570                 575

Asn Arg Lys Lys Leu Ser Glu Leu Leu Arg Tyr Tyr Thr Ser Ala Ser
            580                 585                 590

Gly Asp Glu Met Val Ser Leu Lys Asp Tyr Cys Thr Arg Met Lys Glu
        595                 600                 605

Asn Gln Lys His Ile Tyr Tyr Ile Thr Gly Glu Thr Lys Asp Gln Val
610                 615                 620

Ala Asn Ser Ala Phe Val Glu Arg Leu Arg Lys His Gly Leu Glu Val
625                 630                 635                 640

Ile Tyr Met Ile Glu Pro Ile Asp Glu Tyr Cys Val Gln Gln Leu Lys
                645                 650                 655

Glu Phe Glu Gly Lys Thr Leu Val Ser Val Thr Lys Glu Gly Leu Glu
            660                 665                 670

Leu Pro Glu Asp Glu Glu Lys Lys Lys Gln Glu Glu Lys Lys Thr
        675                 680                 685

Lys Phe Glu Asn Leu Cys Lys Ile Met Lys Asp Ile Leu Glu Lys Lys
690                 695                 700

Val Glu Lys Val Val Val Ser Asn Arg Leu Val Thr Ser Pro Cys Cys
705                 710                 715                 720

Ile Val Thr Ser Thr Tyr Gly Trp Thr Ala Asn Met Glu Arg Ile Met
                725                 730                 735

Lys Ala Gln Ala Leu Arg Asp Asn Ser Thr Met Gly Tyr Met Ala Ala
            740                 745                 750

Lys Lys His Leu Glu Ile Asn Pro Asp His Ser Ile Ile Glu Thr Leu
        755                 760                 765

Arg Gln Lys Ala Glu Ala Asp Lys Asn Asp Lys Ser Val Lys Asp Leu
770                 775                 780

Val Ile Leu Leu Tyr Glu Thr Ala Leu Leu Ser Ser Gly Phe Ser Leu
785                 790                 795                 800

Glu Asp Pro Gln Thr His Ala Asn Arg Ile Tyr Arg Met Ile Lys Leu
                805                 810                 815

Gly Leu Gly Ile Asp Glu Asp Asp Pro Thr Ala Asp Asp Thr Ser Ala
            820                 825                 830

Ala Val Thr Glu Glu Met Pro Pro Leu Glu Gly Asp Asp Asp Thr Ser
        835                 840                 845

Arg Met Glu Glu Val Asp
```

<210> SEQ ID NO 11
<211> LENGTH: 37
<212> TYPE: PRT
<213> ORGANISM: Homo sapiens

<400> SEQUENCE: 11

Val Ala Ile Lys Glu Leu Arg Glu Ala Thr Ser Pro Lys Ala Asn Lys
1               5                   10                  15

Glu Ile Leu Asp Glu Ala Tyr Val Met Ala Ser Val Asp Asn Pro His
            20                  25                  30

Val Cys Arg Leu Leu
        35

<210> SEQ ID NO 12
<211> LENGTH: 38
<212> TYPE: PRT
<213> ORGANISM: Homo sapiens

<400> SEQUENCE: 12

Val Ala Ile Lys Val Leu Arg Glu Asn Thr Ser Pro Lys Ala Asn Lys
1               5                   10                  15

Glu Ile Leu Asp Glu Ala Tyr Val Met Ala Gly Val Gly Ser Pro Tyr
            20                  25                  30

Val Ser Arg Leu Leu Gly
        35

<210> SEQ ID NO 13
<211> LENGTH: 39
<212> TYPE: PRT
<213> ORGANISM: Homo sapiens

<400> SEQUENCE: 13

Val Ala Val Lys Met Leu Lys Ser Asp Ala Thr Glu Lys Asp Leu Ser
1               5                   10                  15

Asp Leu Ile Ser Glu Met Glu Met Lys Met Ile Gly Lys His Lys
            20                  25                  30

Asn Ile Ile Asn Leu Leu Gly
        35

<210> SEQ ID NO 14
<211> LENGTH: 39
<212> TYPE: PRT
<213> ORGANISM: Homo sapiens

<400> SEQUENCE: 14

Val Ala Val Lys Met Leu Lys Asp Asp Ala Thr Glu Lys Asp Leu Ser
1               5                   10                  15

Asp Leu Val Ser Glu Met Glu Met Lys Met Ile Gly Lys His Lys
            20                  25                  30

Asn Ile Ile Asn Leu Leu Gly
        35

<210> SEQ ID NO 15
<211> LENGTH: 39
<212> TYPE: PRT
<213> ORGANISM: Homo sapiens

<400> SEQUENCE: 15

Val Ala Val Lys Met Leu Lys Asp Asp Ala Thr Asp Lys Asp Leu Ser
1               5                   10                  15

```
Asp Leu Val Ser Glu Met Glu Met Met Lys Met Ile Gly Lys His Lys
            20                  25                  30

Asn Ile Ile Asn Leu Leu Gly
            35

<210> SEQ ID NO 16
<211> LENGTH: 39
<212> TYPE: PRT
<213> ORGANISM: Homo sapiens

<400> SEQUENCE: 16

Val Ala Val Lys Met Leu Lys Asp Asn Ala Thr Asp Lys Asp Leu Ser
 1               5                  10                  15

Asp Leu Val Ser Glu Met Glu Met Met Lys Met Ile Gly Lys His Lys
            20                  25                  30

Asn Ile Ile Asn Leu Leu Gly
            35
```

TREATMENT FOR ACHONDROPLASIA

CROSS-REFERENCE TO RELATED APPLICATION

This application claims the benefit of the filing date of U.S. Provisional Patent Application Ser. No. 61/019,759, filed on Jan. 8, 2008. The contents of this prior application are hereby incorporated by reference in their entirety.

TECHNICAL FIELD

This invention relates to treatments for achondroplasia.

BACKGROUND

Fibroblast growth factor receptors (FGFRs) are a family of tyrosine kinase receptors (e.g., FGFR1, FGFR2, FGFR3 and FGFR4) that bind and are activated by members of the fibroblast growth factors (FGFs) (see, e.g., Horton et al., *Lancet* (2007), 370(9582):162-72; Ornitz and Marie, *Genes & Dev.* (2002), 16: 1446-1465).

Achondroplasia (ACH) is the most common form of short-limb dwarfism. Characteristic features of achondroplasia include a short stature, an average-size trunk, short arms and legs with particularly short upper arms and thighs, limited range of motion at the elbows, and an enlarged head (macrocephaly) with a prominent forehead (see, e.g., OMIM 100800). About 80 percent of achondroplasia cases result from a mutation in the fibroblast growth factor receptor 3 (FGFR3) gene. There are also a number of other skeletal disorders associated with mutations in FGFR3 and other FGFRs.

Heat shock protein-90 (Hsp90) is a eukaryotic chaperone that ensures proper folding of proteins. Hsp90 preferentially stabilizes mutant kinases involved in various tumors, and mutant kinases are more sensitive to the inhibition of Hsp90 than wild-type kinases (see, e.g., Citri et al., *Embo J.*, 21: 2407-17 (2002); Germano et al., *J Biol Chem* 281: 21710-9 (2006)).

SUMMARY

The invention is based, in part, on the discovery that FGFR3 is a client protein of Hsp90, and that Hsp90 inhibitors decrease FGFR3 protein levels and activities in cells. The present application provides, inter alia, therapeutic and screening methods based on these discoveries.

In one aspect, the invention provides methods of reducing fibroblast growth factor receptor (FGFR, e.g., FGFR1, FGFR2, FGFR3, and/or FGFR4) activity, e.g., FGFR protein level, FGFR signaling, or FGFR mediated processes, in a cell by administering a Heat Shock Protein-90 (Hsp90) inhibitor, e.g., 17-AAG, to the cell in an amount sufficient to reduce FGFR activity in the cell and monitoring the cell for reduced FGFR activity.

In another aspect, the invention includes methods of reducing fibroblast growth factor receptor (FGFR, e.g., FGFR1, FGFR2, FGFR3, and/or FGFR4) activity, e.g., FGFR protein level, FGFR signaling, or FGFR mediated processes, in a patient (e.g., a human) by administering a Heat Shock Protein-90 (Hsp90) inhibitor, e.g., 17-AAG, to the patient in an amount sufficient to reduce FGFR activity in the patient. The method could further include identifying a patient in need of reduced FGFR activity, and/or monitoring the patient for reduced FGFR activity.

In yet another aspect, the invention provides methods of promoting bone growth, e.g., linear bone growth, in a patient (e.g., a human) by administering to the patient an amount of a Heat Shock Protein-90 (Hsp90) inhibitor effective to promote bone growth in the patient. The method could further include identifying a patient in need of increased bone growth, and/or monitoring the patient for increased bone growth.

The invention also includes methods of treating an FGFR related disorder in a patient by identifying a patient having an FGFR related disorder, and administering to the patient an amount of a Heat Shock Protein-90 (Hsp90) inhibitor effective to treat the FGFR related disorder in the patient. The FGFR related disorder can be, e.g., achondroplasia (ACH), thanatophoric dysplasia type I (TDI), thanatophoric dysplasia type II (TDII), hypochondroplasia (HCH), Crouzon craniosynostosis, the San Diego form of skeletal dysplasia, Muenke nonsyndromic coronal craniosynostosis, Jackson-Weiss syndrome, Apert syndrome, Pfeiffer syndrome, Crouzon syndrome, Saethre-Chotzen syndrome, osteoglophonic dysplasia, Beare-Stevenson cutis gyrata syndrome, Antley-Bixler syndrome, SADDAN (severe achondroplasia with developmental delay and acanthosis nigricans) syndrome, lacrimoauriculodentodigital (LADD) syndrome, the camptodactyly, tall stature, scoliosis, and hearing loss syndrome (CATSHL syndrome), epidermal nevi, acanthosis nigricans, nonsyndromic cleft lip or palate, B-cell tumor, multiple myeloma, epithelial cancer, bladder cancer, or cervical cancer. For example, the FGFR related disorder can be, e.g., an FGFR3 related disorder, such as achondroplasia.

The present application describes methods of increasing the size or height of a patient, e.g., a human patient, by administering to the patient an amount of a Heat Shock Protein-90 (Hsp90) inhibitor effective to increase the size or height of the patient. The method could further include identifying a patient in need of increased height or size, or monitoring the patient for increased height or size after administration of the Hsp90 inhibitor.

The Hsp90 inhibitor can be, for example, geldanamycin or a derivative thereof. The Hsp90 inhibitor can also include 17-ally-lamino-17-demethoxygeldanamycin (17-AAG), 17-(2-dimethylaminoethyl)amino-17-demethoxygeldanamycin (17-DMAG), tanespimycin, retaspimycin, IPI-493, CNF-1010, alvespimycin, BIIB021, SNX-5422 and STAT-9090.

The present invention provides isolated FGFR, e.g., FGFR1, FGFR2, FGFR3 or FGFR4, polypeptides or Hsp90-binding fragments thereof. The FGFR polypeptide fragment can be an FGFR domain that binds to Hsp-90. The fragment can include, e.g., about 10 to about 60, e.g., about 20 to about 50, about 30 to about 40, e.g., about 39, residues of an FGFR polypeptide. For example, an FGFR polypeptide fragment can include amino acid residues corresponding to about 505 to about 543 of SEQ ID NO:6. As shown in FIG. 1, exemplary FGFR polypeptide fragments useful in the present invention are fragments comprising amino acid residues about 511 to about 549 of FGFR1 (e.g., Accession No. NM_023110), residues about 514 to about 552 of FGFR2 (e.g., Accession No. NP_000132), residues about 505 to about 543 of SEQ ID NO:6, and residues about 500 to 538 of FGFR4 (e.g., Accession No. NM_002011). The FGFR fragment can include an amino acid residue corresponding to G533 of SEQ ID NO:6.

In still another aspect, the invention includes fusion proteins that include (i) a first amino acid sequence comprising the amino acid sequence of an FGFR polypeptide, or an Hsp90-binding fragment thereof, and (ii) a second amino acid sequence unrelated to the first amino acid sequence, wherein the fusion protein displays Hsp90-binding ability.

The invention also include isolated nucleic acid molecules encoding the polypeptides described herein, e.g., FGFR, e.g., FGFR1, FGFR2, FGFR3 or FGFR4, polypeptides, Hsp90-binding fragments thereof, and fusion proteins.

In another aspect, the invention provide cells that include exogenously—introduced nucleic acid molecules that encode the polypeptides described herein, e.g., FGFR, e.g., FGFR1, FGFR2, FGFR3, or FGFR4, an Hsp90-binding fragment thereof, and fusion proteins. In certain embodiments, the cells include nucleic acid molecules that encode Hsp90, e.g., human Hsp90, polypeptides or FGFR-binding fragments thereof.

Also described herein are methods of identifying a candidate Hsp90 inhibitor. The methods include contacting a test compound, an Hsp90 polypeptide or fragment thereof (e.g., an FGFR-binding fragment), and an FGFR polypeptide or fragment thereof (e.g., an Hsp90-binding fragment), e.g., an FGFR1, FGFR2, FGFR3, FGFR4 polypeptide or a fragment thereof, under conditions and for a time sufficient to allow an interaction (e.g., binding or association) between the Hsp90 polypeptide or fragment thereof and the FGFR polypeptide or fragment thereof, and detecting whether the test compound inhibits an interaction between the Hsp90 polypeptide or fragment thereof and the FGFR polypeptide or fragment thereof, wherein a test compound that inhibits an interaction between the Hsp90 polypeptide and the FGFR polypeptide is a candidate Hsp90 inhibitor.

The application also provides methods of identifying a candidate compound for treating an FGFR related disorder, e.g., an FGFR3 related disorder. The methods include contacting a test compound, an Hsp90 polypeptide or fragment thereof (e.g., an FGFR-binding fragment), and an FGFR polypeptide or fragment thereof (e.g., an Hsp90-binding fragment), e.g., an FGFR1, FGFR2, FGFR3, FGFR4 polypeptide or a fragment thereof, under conditions and for a time sufficient to allow an interaction (e.g., binding or association) between the Hsp90 polypeptide or fragment thereof and the FGFR polypeptide or fragment thereof, and detecting whether the test compound inhibits an interaction between the Hsp90 polypeptide or fragment thereof and the FGFR polypeptide or fragment thereof, wherein a test compound that inhibits an interaction between the Hsp90 polypeptide and the FGFR polypeptide is a candidate Hsp90 inhibitor.

The application also provides methods of identifying a candidate compound for treating achondroplasia. The methods include contacting a test compound, an Hsp90 polypeptide or fragment thereof (e.g., an FGFR-binding fragment), and an FGFR polypeptide or fragment thereof (e.g., an Hsp90-binding fragment), e.g., an FGFR1, FGFR2, FGFR3, FGFR4 polypeptide or a fragment thereof, under conditions and for a time sufficient to allow an interaction (e.g., binding or association) between the Hsp90 polypeptide or fragment thereof and the FGFR polypeptide or fragment thereof, and detecting whether the test compound inhibits an interaction between the Hsp90 polypeptide or fragment thereof and the FGFR polypeptide or fragment thereof, wherein a test compound that inhibits an interaction between the Hsp90 polypeptide and the FGFR polypeptide is a candidate Hsp90 inhibitor.

The FGFR polypeptide or fragment thereof or the Hsp90 polypeptide or fragment thereof, or both, used in the methods provided herein can be labeled with any label that will allow its detection, e.g., a radiolabel, a fluorescent agent, biotin, a peptide tag, or an enzyme fragment.

Also included herein are methods for identifying a candidate compound, e.g., a candidate compound that inhibits Hsp90 activity, or for treating an FGFR related disorder, e.g., an FGFR3 related disorder, e.g., achondroplasia. The methods include: (a) providing a polypeptide that: (i) comprises an FGFR protein or a fragment thereof, and (ii) displays Hsp90-binding ability; (b) providing a second polypeptide that: (i) comprises an Hsp90 protein or a fragment thereof; and (ii) displays FGFR-binding ability; (c) contacting the first and second polypeptides in the presence of a test compound; and (d) comparing the level of binding between the first and second polypeptides in the presence of the test compound with the level of binding in the absence of the test compound, wherein a different level of binding in the presence of the test compound than in its absence indicates that the test compound is a candidate compound.

The methods can further include: (e) determining whether the candidate compound reduces Hsp90 activity in vivo or in vitro, wherein reduction indicates that the candidate compound is an Hsp90 inhibitor. The test compound can be, e.g., a polypeptide, a ribonucleic acid, a small molecule and/or a deoxyribonucleic acid.

The first polypeptide can be provided as a fusion protein comprising the polypeptide fused to (i) a transcription activation domain of a transcription factor or (ii) a DNA-binding domain of a transcription factor; the second polypeptide can be provided as a fusion protein comprising the polypeptide fused to (i) a transcription activation domain of a transcription factor or (ii) a DNA-binding domain of a transcription factor, to interact with the fusion protein; and binding of the first and second polypeptides can be detected as reconstitution of a transcription factor.

The FGFR, e.g., FGFR1, FGFR2, FGFR3, FGFR4, or Hsp90 polypeptide or fragment thereof useful for the methods described herein can be an isolated or recombinant polypeptide.

Also provided herein are kits for identifying a candidate Hsp90 inhibitor. The kits can include: (a) an isolated FGFR polypeptide, e.g., an FGFR1, FGFR2, FGFR3, FGFR4 polypeptide or Hsp90-binding fragment thereof; and (b) an isolated Hsp90 polypeptide or FGFR-binding fragment thereof. The kit can optionally include (c) instructional material for using the FGFR polypeptide and Hsp90 polypeptide to identify the candidate Hsp90 inhibitor. For example, the kit can include a composition comprising an FGFR3 polypeptide or fragment thereof In some instances, the kit can comprise multiple FGFR polypeptides. The kit can include other ingredients, e.g., agents, compounds, or materials, for practicing the screening methods for identifying candidate Hsp90 inhibitors. In those instances, the kit can include instructions for using FGFR polypeptides and Hsp90 polypeptides together with the other ingredients. In certain embodiments, the FGFR, e.g., FGFR1, FGFR2, FGFR3, FGFR4, or Hsp90 polypeptide or fragment thereof can be a recombinant polypeptide.

The informational material can be descriptive, instructional, marketing or other material that relates to the screening methods described herein and/or the use of FGFR polypeptides and Hsp90 polypeptides for the screening methods described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF DRAWINGS

FIGS. 2A and 2B show exemplary human FGFR1 nucleic acid (A—SEQ ID NO: 1) and amino acid (B—SEQ ID NO: 2) sequences.

FIGS. 3A and 3B show exemplary human FGFR2 nucleic acid (A—SEQ ID NO: 3) and amino acid (B—SEQ ID NO: 4) sequences.

FIGS. 4A and 4B show exemplary human FGFR3 nucleic acid (A—SEQ ID NO: 5) and amino acid (B—SEQ ID NO: 6) sequences.

FIGS. 5A and 5B show exemplary human FGFR4 nucleic acid (A—SEQ ID NO: 7) and amino acid (B—SEQ ID NO: 8) sequences.

FIGS. 6A and 6B show exemplary human Hsp90 nucleic acid (A—SEQ ID NO: 9) and amino acid (B—SEQ ID NO: 10) sequences.

FIGS. 8A and 8B) and mutant FGFR3 (TDI, TDII and ACH; FIG. 8B) proteins in cells treated with 17-AAG FIG. 8A suggests that the reduction is specific for FGFR3 protein as other bands on the crude cell lysate blot do not change. FIG. 8B suggests that mutant FGFR3s are more sensitive to 17-AAG treatment than WT FGFR3.

FIGS. 16A and 16B are graphs showing femoral length of heterozygous (HET) FGFR3 mutant female mice treated (RX) and untreated (CTR) with 17-AAG. FIG. 16A is without error bars and FIG. 16B is with error bars. n=number of femurs. Also note that each mouse has two femurs, so number of mice measured=n/2. Measurements were made on scanned skeletal X-rays.

FIGS. 17A and 17B are graphs showing femoral length of heterozygous (HET) FGFR3 mutant male mice treated (RX) and untreated (CTR) with 17-AAG. FIG. 17A is without error bars and FIG. 17B is with error bars. n=number of femurs. Also note that each mouse has two femurs, so number of mice measured=n/2. Measurements were made on scanned skeletal X-rays.

DETAILED DESCRIPTION

Figure 1:
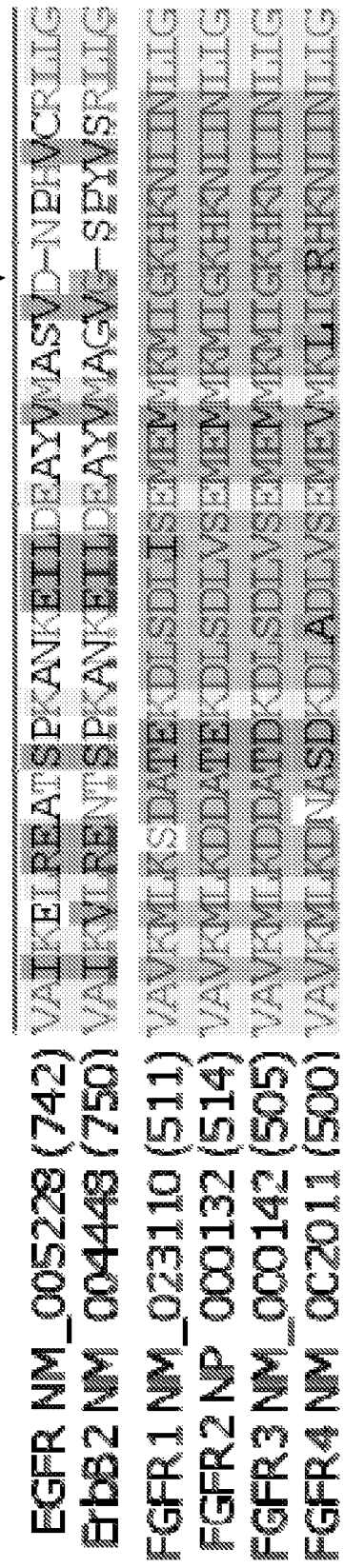
FIG. 1 shows a partial alignment of the amino acid sequences of Hsp90 client proteins SEQ ID NOs 11, 12, 13, 14, 15 and 16, respectively.

The present invention is based, at least in part, on the discovery that FGFR3 is a client protein of the chaperone Hsp90, and that Hsp90 inhibitors decrease FGFR3 protein level and activity in cells. Data provided herein demonstrates that administering an Hsp90 inhibitor increases bone growth in mutant FGFR3 transgenic mice. Other FGFRs, e.g., FGFR1, FGFR2, and FGFR4, are also Hsp90 client proteins. Accordingly, the present application provides, inter alia, methods of treating disorders mediated by FGFRs (e.g., FGFR3), for example, achondroplasia, and methods of screening for Hsp90 inhibitor compounds.

I. FGFR Related Disorders and Treatments Therefor

The invention provides therapeutic methods for treating FGFR related disorders in a patient, e.g., by reducing Hsp90 activity or promoting bone growth, e.g., by administering an Hsp90 inhibitor to the patient. As used herein, an "FGFR related disorder" is a disorder associated with (e.g., caused by, resulting from, attributed to or correlated with, at least in part) mutations in FGFRs, e.g., FGFR1, FGFR2, FGFR3, or FGFR4. FGFR related disorders can include, but are not limited to, various skeletal disorders such as achondroplasia (ACH), thanatophoric dysplasia type I (TDI), thanatophoric dysplasia type II (TDII), hypochondroplasia (HCH), Crouzon craniosynostosis, the San Diego form of skeletal dysplasia, Muenke nonsyndromic coronal craniosynostosis, Jackson-Weiss syndrome, Apert syndrome, Pfeiffer syndrome, Crouzon syndrome, Saethre-Chotzen syndrome, osteoglophonic dysplasia, Beare-Stevenson cutis gyrata syndrome, Antley-Bixler syndrome, severe achondroplasia with developmental delay and acanthosis nigricans (SADDAN) syndrome, lacrimoauriculodentodigital (LADD) syndrome, and the camptodactyly, tall stature, scoliosis, and hearing loss (CATSHL) syndrome. FGFR related disorders can also include epidermal nevi, acanthosis nigricans, nonsyndromic cleft lip or palate, B-cell tumor, multiple myeloma, epithelial cancer, bladder cancer, and cervical cancer.

The invention also provides methods of increasing the height of a patient, e.g., by reducing Hsp90 activity, reducing FGFR3 activity or level, or promoting bone growth, e.g., by administering an Hsp90 inhibitor to the patient.

The terms "patient" is used throughout the specification to describe an animal, human or non-human, rodent or non-rodent, to whom treatment according to the methods of the present invention is provided. Veterinary and non-veterinary applications are contemplated. The term includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Typical patients include humans, farm animals, and domestic pets such as cats and dogs.

Decreasing Hsp90 or FGFR Activity

Hsp90 or FGFR, e.g., FGFR3, activity can be reduced (i.e., decreased, e.g., eliminated) in a patient by any method known to those of ordinary skill in the art. For example, an Hsp90 inhibitor can be administered to the patient. As used herein, an "Hsp90 inhibitor" is a compound that is capable of inhibiting (i.e., decreasing, e.g., eliminating) the activity of Hsp90 toward its client protein, e.g., an FGFR (e.g., FGFR1, 2, 3 or 4). An Hsp90 inhibitor can inhibit or decrease Hsp90 activity, for example, by inhibiting Hsp90 enzymatic activity or interfering with the protein-protein interaction between Hsp90 and its client protein. A number of Hsp90 inhibitors are known in the art. An Hsp90 inhibitor can be, e.g., a small molecule, a protein, or a nucleic acid.

Exemplary Hsp90 inhibitors include geldanamycin and its derivatives (see U.S. Pat. No. 7,259,156), such as 17-allylamino-17-demethoxygeldanamycin (17-AAG), e.g., tanespimycin (Kosan Biosciences); retaspimycin (Infinity/MedImmune/AstraZeneca); IPI-493 (Infinity/MedImmune/AstraZeneca); CNF-1010 (Biogen Idec), and 17-(2-dimethylaminoethyl)amino-17-demethoxygeldanamycin (17-DMAG), e.g., alvespimycin (Kosan Biosciences). Other exemplary Hsp-90 inhibitors include BIIB021 (CNF-2024; Biogen Idec), SNX-5422 (Serenex) and STAT-9090 (Synta Pharmaceuticals). Other Hsp90 inhibitors can be identified by screening methods described herein.

Other art-known methods for decreasing the expression of a particular protein in a patient can be employed in order to, e.g., decrease Hsp90 or FGFR activity by decreasing the amount of Hsp90 or FGFR in a patient. For example, an antisense nucleic acid effective to inhibit expression of an endogenous Hsp90 or FGFR gene can be utilized. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide that hybridizes under physiological conditions to DNA comprising a particular gene or to an mRNA transcript of that gene and, thereby, inhibits the transcription of that gene and/or the translation of that mRNA.

Antisense molecules are designed so as to interfere with transcription or translation of a target gene upon hybridization with the target gene or transcript. The antisense nucleic acid can include a nucleotide sequence complementary to an entire Hsp90 RNA or FGFR RNA, or only a portion of the RNA. The nucleic acid sequences that code for Hsp90 (e.g., human Hsp90) and FGFR (e.g., human FGFR3) are known in the art and are available to skilled practitioners. On one hand, the antisense nucleic acid needs to be long enough to hybridize effectively with Hsp90 or FGFR RNA. Therefore, the minimum length is approximately 12 to 25 nucleotides. On the other hand, as length increases beyond about 150 nucleotides, effectiveness at inhibiting translation may increase only marginally, while difficulty in introducing the antisense nucleic acid into target cells may increase significantly. Accordingly, an appropriate length for the antisense nucleic acid may be from about 15 to about 150 nucleotides, e.g., 20, 25, 30, 35, 40, 45, 50, 60, 70, or 80 nucleotides. The antisense nucleic acid can be complementary to a coding region of Hsp90 or FGFR mRNA or a 5' or 3' non-coding region of the mRNA, or both. One approach is to design the antisense nucleic acid to be complementary to a region on both sides of the translation start site of the Hsp90 or FGFR mRNA.

Based upon known Hsp90 and FGFR sequences, one of ordinary skill in the art can easily choose and synthesize any of a number of appropriate antisense molecules for use in accordance with the present invention. For example, a "gene walk" comprising a series of oligonucleotides of 15-30 nucleotides spanning the length of an Hsp90 or an FGFR nucleic acid can be prepared, followed by testing for inhibition of Hsp90 expression. Optionally, gaps of 5-10 nucleotides can be left between the oligonucleotides to reduce the number of oligonucleotides synthesized and tested.

The antisense nucleic acid can be chemically synthesized, e.g., using a commercial nucleic acid synthesizer according to the vendor's instructions. Alternatively, the antisense nucleic acids can be produced using recombinant DNA techniques. An antisense nucleic acid can incorporate only naturally occurring nucleotides. Alternatively, it can incorporate variously modified nucleotides or nucleotide analogs to increase its in vivo half-life or to increase the stability of the duplex formed between the antisense molecule and its target RNA. Examples of nucleotide analogs include phosphorothioate derivatives and acridine-substituted nucleotides. Given the description of the targets and sequences, the design and production of suitable antisense molecules is within ordinary skill in the art. For guidance concerning antisense nucleic acids, see, e.g., Goodchild, "Inhibition of Gene Expression by Oligonucleotides," in *Topics in Molecular and Structural Biology, Vol.* 12: *Oligodeoxynucleotides* (Cohen, ed.), MacMillan Press, London, pp. 53-77.

Delivery of antisense oligonucleotides can be accomplished by any method known to those of skill in the art. Delivery of antisense oligonucleotides for in vivo applications can be accomplished, for example, via local injection of the antisense oligonucleotides at a selected site. This method has previously been demonstrated for psoriasis growth inhibition and for cytomegalovirus inhibition. See, for example, Wraight et al., (2001). *Pharmacol Ther*. Apr; 90(1):89-104.; Anderson, et al., (1996) *Antimicrob Agents Chemother* 40: 2004-2011; and Crooke et al., *J Pharmacol Exp Ther* 277: 923-937. To resist nuclease degradation, chemical modifications such as phosphorothionate backbones can be incorporated into the molecule.

Similarly, RNA interference (RNAi) techniques can be used to inhibit Hsp90 or FGFR, e.g., FGFR3, in addition or as an alternative to, the use of antisense techniques. For example, small interfering RNA (siRNA) duplexes directed against Hsp90 or FGFR nucleic acids could be synthesized and used to prevent expression of the encoded protein(s).

Another approach to inhibiting Hsp90 activity is the administration of a compound that prevents interaction between Hsp90 and FGFR (e.g., FGFR3), e.g., by binding to Hsp90, FGFR, or both, and interfering with the protein-protein interaction, e.g., binding or association, between the two. Such compounds can be identified, e.g., using screening methods described herein. One example of a compound that can bind to an Hsp90 polypeptide is an Hsp90-binding portion of an FGFR, e.g., an Hsp90-binding fragment of FGFR3, e.g., the middle domain of Hsp90 (e.g., about amino acids 272-617 of human Hsp90) (see, e.g., Pearl and Prodromou, Annu. Rev. Biochem. 2006; 75:271-94; Lotz et al., J. Biol. Chem., 2003; 278(19): 17228-17235). Another example is an FGFR-binding fragment of Hsp90, e.g., about amino acids 500-550 of human FGFR3 (see FIG. 1). Skilled practitioners could obtain an Hsp90-binding fragment of an FGFR protein, e.g., human FGFR3 protein, useful for the methods described herein by using known techniques, e.g., conventional sequence alignment methods. Still another example is an antibody (i.e., an anti-Hsp90 or anti-FGFR antibody) capable of inhibiting the interaction (e.g., binding) between Hsp90 and FGFR, e.g., an antibody that binds to the FGFR-binding region of Hsp90 or to the Hsp90-binding region of an FGFR. All such compounds are considered part of the present invention.

Antibodies described herein can be polyclonal or monoclonal. The antibody can be produced recombinantly, e.g., produced by phage display or by combinatorial methods as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffihs et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982.

As used herein, the term "antibody" refers to a protein comprising at least one, e.g., two, heavy (H) chain variable regions (abbreviated herein as VH), and at least one, e.g., two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917). Each VH and VL is composed of three CDR's and four FRs, arranged from amino-terminus to carboxy-terminus in the following order: FR1, CDR1, FR2, CDR2, FR3, CDR3, FR4.

An anti-Hsp90 or FGFR antibody can further include a heavy and light chain constant region, to thereby form a heavy and light immunoglobulin chain, respectively. The antibody can be a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2, and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

A "binding fragment" of an antibody refers to one or more fragments of a full-length antibody that retain the ability to specifically bind to FGFR or Hsp90 polypeptide or portions thereof. "Specifically binds" means that an antibody or ligand binds to a particular target and not to other unrelated substances, except in an easily reversible or "background" type interaction. Examples of binding fragments of an anti-FGFR or Hsp90 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "binding fragment" of an antibody. These antibody fragments can be obtained using conventional techniques known to those with skill in the art.

Antibodies can be fully human antibodies (e.g., an antibody made in a mouse which has been genetically engineered to produce an antibody from a human immunoglobulin sequence), or a non-human antibody, e.g., a rodent (mouse or rat), goat, primate (e.g., monkey), camel, donkey, porcine, or fowl antibody.

An antibody can be one in which the variable region, or a portion thereof, e.g., a CDR, is generated in a non-human organism, e.g., a rat or mouse. The antibody can also be, for example, a chimeric, CDR-grafted, or humanized antibody. The antibody can also be generated in a non-human organism, e.g., a rat or mouse, and then modified, e.g., in the variable framework or constant region, to decrease antigenicity in a human.

Pharmaceutical Compositions

Compounds useful in treating FGFR related disorders can be incorporated into pharmaceutical compositions. Such compositions typically include the compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent which delays absorption, e.g., aluminum monostearate and gelatin in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the patient to be treated; each unit containing a predetermined quantity of active compound calculated to produce the desired therapeutic effect in association with the required pharmaceutical carrier.

The pharmaceutical compositions can be included in a container, pack, or dispenser together with instructions for administration.

Administration

For Hsp90 inhibitors known in the art (e.g., Tanespimycin), practitioners might generally use in humans and non-human animals the recommended (e.g., FDA approved) dosage for that Hsp90 inhibitor.

For others, toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

While compounds that exhibit toxic side effects may be used, it may be possible to design a delivery system that targets such compounds to the site of affected tissue, e.g., bones or tumors, in order to reduce side effects. For example, the compounds described herein can be prepared such that they are targeted to the bones or cartilage of patients. Methods are known in the art for targeting a compound to bones, or for selectively activating a compound in bones. For example, compounds can be conjugated to bisphosphonates, which have been used successfully to target drugs to bones. Alternatively, prodrugs can be generated such that they are activated by matrix metalloproteinase 9 (MMP-9), which is abundantly produced in osteoclasts and chondroclasts. Using these known methods, Hsp90 inhibitors can be targeted to the bones or cartilage of patients, see, e.g., Uludag et al., *Biotechnol Prog* 16, 1115-8 (2000); Uludag et al., *Biotechnol Prog* 16, 258-67 (2000); Hirabayashi et al., *Clin Pharmacokinet* 42, 1319-30 (2003); Bansal et al., *J Biomed Mater Res A* 74, 618-28 (2005); Gittens et al., *Adv Drug Deliv Rev* 57, 1011-36 (2005); Bansal et al., *J Pharm Sci* 93, 2788-99 (2004); Van Valckenborgh et al., *Leukemia* 19, 1628-33 (2005). Animal models can be used to test whether the compounds are targeted to the bones, and to determine dosages for achieving a range of concentrations in the bones effective for treating FGFR related skeletal disorders or to increase the height of a patient. Localized administration of compounds using methods known the art, e.g., localized injection of compounds into tumors, can also be used to deliver Hsp90 inhibitors to the site of affected tissue.

Data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The terms "effective amount" and "effective to treat," as used herein, refer to an amount or a concentration of Hsp90 inhibitor utilized for a period of time (including acute or chronic administration and periodic or continuous administration) that is effective within the context of its administration for causing an intended effect or physiological outcome. Effective amounts of Hsp90 inhibitors for use in the present invention include, for example, amounts that, e.g., reduce Hsp90 activity or FGFR activity, or generally improve the prognosis of a patient diagnosed with an FGFR related disorder. The term "treat(ment)" is used herein to describe delaying the onset of, inhibiting, or alleviating the detrimental effects of a condition, e.g., an FGFR related disorder.

For the compounds described herein, an effective amount, e.g. of a small molecule, protein or polypeptide (i.e., an effective dosage), ranges from about 0.001 to 30 mg/kg body weight, e.g. about 0.01 to 25 mg/kg body weight, e.g. about 0.1 to 20 mg/kg body weight. The compound can be administered, e.g., one time per week for between about 1 to 10 weeks, e.g. between 2 to 8 weeks, about 3 to 7 weeks, or for about 4, 5, or 6 weeks. In certain cases, the compound can be administered for a period of years, e.g., one to three times per week for between 1 to 20 years, e.g., between 2 to 5 years, about 5 to 8 years, or for about 5, 10, 15, or 20 years. In some cases, e.g., treating FGFR related skeletal disorders such as achondroplasia, the compound can be administered to a patient from the time of diagnosis until the patient reaches late puberty. The skilled artisan will appreciate that certain factors influence the dosage and timing required to effectively treat a patient, including but not limited to the type of patient to be treated, the severity of the disease or disorder, previous treatments, the general health and/or age of the patient, and other disorders present. Moreover, treatment of a patient with a therapeutically effective amount of a protein, polypeptide, antibody, or other compound can include a single treatment or, preferably, can include a series of treatments.

Nucleic acid molecules encoding an Hsp90-binding fragment of an FGFR (e.g., FGFR3) and/or an FGFR (e.g., FGFR3) binding fragment of Hsp90 can be inserted into vectors and used as gene therapy vectors. Gene therapy vectors can be delivered to a patient by, for example, intravenous injection, local administration (see, e.g., U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

If the compound is a small molecule, exemplary doses include milligram or microgram amounts of the small molecule per kilogram of patient or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal patient will depend upon a variety of factors including the activity of the specific compound employed, the age, body weight, general health, gender, and diet of the patient, the time of administration, the route of administration, the rate of excretion, any drug combination, and the degree of expression or activity to be modulated.

For antibodies, a useful dosage is 0.1 mg/kg of body weight (generally 10 mg/kg to 20 mg/kg). Generally, partially human antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described by Cruikshank et al. ((1997) *J. Acquired Immune Deficiency Syndromes and Human Retrovirology* 14:193).

For the treatment methods described herein, a patient can be treated with an Hsp90 inhibitor alone, or in combination with other agents or therapy.

Monitoring of Treatment

Effectiveness of the treatment methods described herein can be determined by monitoring changes in the symptoms, characteristic features, or parameters of the patient being treated. Skilled practitioners will appreciate that the features to be monitored depend on the specific disorder. In general, for skeletal disorders characterized by bone growth deficiency (e.g., achondroplasia and hypochondroplasia), changes in bone length can be monitored to determine effectiveness of the treatment. Bone length can be determined by methods known in the art, for example, by taking skeletal X-rays of a patient and determining individual bone length using conventional methods, such as using an imaging software, e.g., ImageJ software.

Prior to treatment, a patient can optionally be screened for mutations in FGFRs, e.g., FGFR1, FGFR2, FGFR3, or FGFR4, using methods known in the art, for example, polymerase chain reaction (PCR), DNA sequencing and denaturing high-performance liquid chromatography. A number of specific FGFR3 mutations associated with various disorders have been identified (see, e.g., OMIM 134934). Other mutations in FGFR3 can be identified using methods known to those of ordinary skill in the art.

II. Methods of Screening for Hsp90 Inhibitors or Compounds for Treating FGFR Related Disorders The invention provides screening methods (also referred to herein as "screening assays") for identifying compounds (e.g., peptides, peptidomimetics, small molecules or other drugs) that disrupt the ability of Hsp90 to stabilize FGFRs, e.g., FGFR1, FGFR2, FGFR3 or FGFR4, e.g., by inhibiting the formation of FGFR/Hsp90 complexes (e.g., inhibiting binding of a FGFR and Hsp90).

FGFR and Hsp90 Polypeptides

The terms "protein" and "polypeptide" both refer to any chain of amino acids, regardless of length or post-translational modification (e.g., glycosylation or phosphorylation). Thus, the terms "FGFR protein," "Hsp90 protein," "FGFR polypeptide," and "Hsp90 polypeptide" include, e.g., full-length naturally occurring isolated proteins, as well as recombinantly or synthetically produced polypeptides that correspond to the full-length naturally occurring proteins.

All four FGFRs contain an extracellular ligand-binding domain, a transmembrane domain, and an intracellular domain that includes the kinase domains (see, e.g., Horton et al., *Lancet* (2007), 370(9582):162-72; Ornitz and Marie, *Genes & Dev.* (2002), 16: 1446-1465). Data have demonstrated that the αC-β4 loop within the N-terminal lobe of ErbB2, another Hsp90 client protein, is the region that binds to Hsp90 (see, e.g., Citri et al., EMBO Rep, 2004; 5(12): 1165-1170). This region is conserved in other Hsp90 client proteins, including epidermal growth factor receptor (EGFR), FGFR1, FGFR2, FGFR3 and FGFR4 (see FIG. 1).

Soluble FGFR polypeptides, e.g., FGFR1, FGFR2, FGFR3, or FGFR4 polypeptides, are useful in the methods. In addition, nucleic acids encoding full-length FGFR polypeptides or fragments thereof are useful. FGFR polypeptides and nucleic acids encoding them are readily obtained by one of ordinary skill in the art without undue experimentation. For example, various amino acid and nucleic acid sequences of human FGFRs are known (see SEQ ID NOs: 1-8 for exemplary FGFR sequences). A nucleic acid encoding a mammalian, e.g., human, FGFR3 amino acid sequence can be amplified from human cDNA by conventional PCR techniques, using primers upstream and downstream of the coding sequence. FGFR nucleic acid molecules and polypeptides are also commercially available. For example, vectors containing full-length human FGFR cDNAs can be obtained from Invitrogen and OriGene, and purified recombinant human FGFR polypeptides are available from Invitrogen, BIOMOL International LP, and GenWay Biotech, Inc.

Some embodiments of the invention involve the use of full-length FGFR polypeptides or fragments thereof, e.g., a fragment containing the intracellular domain including the tyrosine kinase domains, or a fragment containing the Hsp90-binding region. The FGFR, e.g., FGFR1, FGFR2, FGFR3, or FGFR4, polypeptide fragment can be an FGFR domain that binds to Hsp-90. The fragment can include, e.g., about 10 to about 60, e.g., about 20 to about 50, about 30 to about 40, e.g., about 39, residues of an FGFR polypeptide. For example, an FGFR polypeptide fragment can include amino acid residues corresponding to about 505 to about 543 of SEQ ID NO:6. As shown in FIG. 1, exemplary FGFR polypeptide fragments useful in the present invention are fragments comprising amino acid residues about 511 to about 549 of FGFR1 (e.g., Accession No. NM_023110), residues about 514 to about 552 of FGFR2 (e.g., Accession No. NP_000132), residues about 505 to about 543 of SEQ ID NO:6, and residues about 500 to 538 of FGFR4 (e.g., Accession No. NM_002011). The FGFR fragment can include an amino acid residue corresponding to G533 of SEQ ID NO:6. Some embodiments of the invention involve the use of full-length FGFR polypeptides or fragments thereof containing mutations found in FGFR related disorders. FGFR polypeptides with altered amino acid sequences can be obtained by site-directed mutagenesis using conventional techniques.

One method for producing FGFR polypeptides for use in the invention is recombinant production, which involves genetic transformation of a host cell with a recombinant nucleic acid vector encoding a FGFR polypeptide, expression of the recombinant nucleic acid in the transformed host cell, and collection and purification of the FGFR polypeptide. Guidance concerning recombinant DNA technology can be found in numerous well-known references, including Sambrook et al., 1989, *Molecular Cloning—A Laboratory Manual*, Cold Spring Harbor Press; and Ausubel et al. (eds.), 1994, *Current Protocols in Molecular Biology*, John Wiley & Sons, Inc.

Purification of recombinant FGFR polypeptides can be performed by conventional methods and is within ordinary skill in the art. The purification can include two or more steps, and one step can be affinity chromatography employing anti-FGFR antibodies covalently linked to a solid phase chromatography support (beads) such as crosslinked agarose or polyacrylamide. Other useful purification steps include gel filtration chromatography and ion exchange chromatography.

The structure of Hsp90 has been determined (see, e.g., Pearl and Prodromou, Annu. Rev. Biochem. 2006; 75:271-94). Hsp90 protein includes an N-terminal domain, a middle domain, a C-terminal domain, and a linker linking the N-terminal domain and the middle segment. The N-terminal domain has been shown to include the binding site for ATP. The middle domain of Hsp90 (e.g., about amino acids 272-617 of human Hsp90) has been shown to bind to Hsp90 client proteins (see, e.g., Pearl and Prodromou, Annu. Rev. Biochem. 2006; 75:271-94; Lotz et al., J. Biol. Chem., 2003; 278(19): 17228-17235). The C-terminal domain is essential for Hsp90 dimerization.

Soluble Hsp90 polypeptides are useful in methods of the invention. In addition, nucleic acids encoding full-length Hsp90 polypeptides or fragments thereof are useful in the methods of the invention. Hsp90 polypeptides and nucleic acids encoding them (see SEQ ID NOs: 9-10 for exemplary human Hsp90 amino acid and nucleic acid sequences) are readily obtained by one of ordinary skill in the art without undue experimentation and can be obtained as described above. Human Hsp90 nucleic acid molecules and polypeptides are also available commercially, for example, from Invitrogen and GenWay Biotech, Inc.

Libraries of Test Compounds

In certain embodiments, screens disclosed herein utilize libraries of test compounds. As used herein, a "test compound" can be any chemical compound, for example, a macromolecule (e.g., a polypeptide, a protein complex, glycoprotein, polysaccharide, or a nucleic acid) or a small molecule (e.g., an amino acid, a nucleotide, or an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include peptides, peptidomimetics (e.g., peptoids, retro-peptides, inverso peptides, and retro-inverso peptides), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., Gordon et al., *J. Med. Chem.*, 37:1385-1401 (1994); Hobbes et ale, *Acc. Chem. Res.*, 29:114 (1996); Armstrong, et al., *Acc. Chem. Res.*, (1996) 29:123; Ellman, *Acc. Chem. Res.*, (1996) 29:132; Gordon et al., *Acc. Chem. Res.*, 29:144 (1996); Lowe, *Chem. Soc. Rev.*, 309 (1995); Blondelle et al., *Trends Anal. Chem.*, 14:83 (1995); Chen et al., *J. Am. Chem. Soc.*, 116:2661 (1994); U.S. Pat. Nos. 5,359,115, 5,362,899, and 5,288,514; PCT Publication Nos. WO92/10092, WO93/09668, WO91/07087, WO93/20242, and WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis," 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al. (*Proc. Natl. Acad. Sci. U.S.A.*, 90:6909 (1993)). Other synthesis methods, including the "tea-bag" technique of Houghten (see, e.g., Houghten et al., *Nature*, 354:84-86 (1991)) can also be used to synthesize libraries of compounds according to the subject invention.

Libraries of compounds can be screened to determine whether any members of the library can inhibit Hsp90 protein-protein interactions with FGFRs, e.g., FGFR1, FGFR2, FGFR3 or FGFR4, and, if so, to identify the inhibitory compound. Methods of screening combinatorial libraries have been described (see, e.g., Gordon et al., *J Med. Chem.*, supra). Exemplary assays useful for screening libraries of test compounds are described above.

Test compounds can also include antibodies, e.g. antibodies that bind to FGFRs or Hsp90. Antibodies suitable for screening in the methods disclosed herein include known antibodies as well as new antibodies (discussed more fully below) that selectively bind to FGFR polypeptides or fragments thereof, or Hsp90 polypeptides or fragments thereof.

Screens

Screens for compounds that inhibit Hsp90 can be performed by identifying from a group of test compounds those that, e.g., inhibit Hsp90 protein-protein interactions, e.g., binding or association, with an FGFR polypeptide, e.g., an FGFR1, FGFR2, FGFR3 or FGFR4 polypeptide, or a fragment thereof. Such compounds are candidate compounds that inhibit Hsp90 activity, and the compounds can be further tested for their ability to destabilize wildtype and/or mutant FGFRs, or other Hsp90 client proteins in vitro or in vivo.

Screens for compounds for treating FGFR related disorders can be performed by identifying from a group of test compounds those that, e.g., inhibit Hsp90 protein-protein interactions with an FGFR polypeptide, e.g., FGFR1, FGFR2, FGFR3 or FGFR4 polypeptide, or a fragment thereof. Such compounds are candidate compounds that inhibit the ability of Hsp90 to stabilize FGFRs, and such compounds can be further tested for their ability to destabilize wildtype and/or mutant FGFRs in vitro or in vivo. The compounds can also be further tested for their ability to inhibit or decrease FGFR activity, level, or signaling in vivo or in vitro. Such compounds can also be tested for their ability to promote or increase chondrocyte proliferation or differentiation in vivo or in vitro. Such compounds are candidate compounds that treat FGFR related disorders, and these candidate compounds can be further assayed for their ability to treat FGFR related disorders in animal models.

In other aspects of the new methods, screens for compounds that treat achondroplasia are performed by identifying from a group of test compounds those that, e.g., inhibit Hsp90 protein-protein interactions with an FGFR3 polypeptide, or a fragment thereof. Such compounds are candidate compounds that inhibits the ability of Hsp90 to stabilize FGFR3, and such compounds can be further tested for their ability to destabilize wildtype and/or mutant FGFR3 (e.g., a mutant human FGFR3 polypeptide with the Gly380Arg amino acid substitution found in achondroplasia patients) in vitro or in vivo. Such compounds can also be further tested for their ability to decrease FGFR3, e.g., wildtype and/or mutant FGFR3, activity, level or signaling in vivo or in vitro. Such compounds can also be tested for their ability to promote or increase chondrocyte proliferation or differentiation in vivo or in vitro. Such compounds are candidate compounds that treat achondroplasia, and such candidate compounds can be further assayed for their ability to treat achondroplasia in animal models.

In other aspects of the new methods, screens for compounds for promoting bone growth in a patient are performed by identifying from a group of test compounds those that, e.g., inhibit Hsp90 protein-protein interactions with an FGFR polypeptide, e.g., an FGFR1, FGFR2, FGFR3 or FGFR4 polypeptide, or a fragment thereof. Such compounds are candidate compounds that inhibit the ability of Hsp90 to stabilize FGFRs, and such compounds can be further tested for their ability to destabilize wildtype and/or mutant FGFRs in vitro or in vivo. Such compounds can also be further tested for their ability to inhibit or decrease FGFR biological activity or signaling in vivo or in vitro. Such compounds can also be tested for their ability to promote or increase chondrocyte proliferation or differentiation in vivo or in vitro. Such compounds are candidate compounds that promote bone growth, and such candidate compounds can be further assayed for their ability to promote bone growth in animal models.

In some aspects of the new methods, screens for compounds for increasing height or size of a patient, e.g., by promoting bone growth, are performed by identifying from a group of test compounds those that, e.g., inhibit Hsp90 protein-protein interactions with an FGFR polypeptide, e.g., an FGFR1, FGFR2, FGFR3 or FGFR4 polypeptide, or a fragment thereof Such compounds are candidate compounds that inhibits the ability of Hsp90 to stabilize FGFRs, and such compounds can be further tested for their ability to destabilize wildtype and/or mutant FGFRs in vitro or in vivo. Such compounds can also be further tested for their ability to inhibit or decrease FGFR biological activity or signaling in vivo or in vitro. Such compounds can also be tested for their ability to promote or increase chondrocyte proliferation or differentiation in vivo or in vitro. Such compounds are candidate compounds that increase height or size of a patient, e.g., by promoting bone growth, and such candidate compounds can be further assayed for their ability to promote bone growth in animal models.

Test compounds that inhibit Hsp90 protein-protein interactions with an FGFR polypeptide, e.g., an FGFR1, FGFR2, FGFR3 or FGFR4 polypeptide, or a fragment thereof are referred to herein as "candidate compounds." Hsp90 inhibitors are candidate compounds further tested and found to be capable of inhibiting the ability of Hsp90 to stabilize a wild-type and/or mutant FGFR polypeptide, e.g., an FGFR1, FGFR2, FGFR3, or FGFR4 polypeptide. Assays disclosed herein may be carried out in whole cell preparations and/or in ex vivo cell-free systems.

A method useful for high throughput screening of compounds capable of modulating protein-protein interactions is described in Lepourcelet et al., *Cancer Cell*, 5: 91-102 (2004), which is incorporated herein by reference in its entirety. Typically, a first protein is provided. The first protein is either (i) an FGFR1, FGFR2, FGFR3 or FGFR4 polypeptide, or a fragment thereof, e.g., a fragment of FGFR3 polypeptide containing the intracellular domain or the Hsp90-binding domain, or (ii) the first protein is an Hsp90 polypeptide, or a fragment thereof. A second protein is provided which is different from the first protein and which is labeled. The second protein is either (i) an FGFR polypeptide, e.g., an FGFR1, FGFR2, FGFR3 or FGFR4 polypeptide, or a fragment thereof, e.g., a fragment of FGFR3 polypeptide containing the intracellular domain, or (ii) the second protein is an Hsp90 polypeptide, or a fragment thereof, e.g., a fragment of Hsp90 polypeptide containing the FGFR-binding domain. A test compound is provided. The first protein, second protein, and test compound are contacted with each other. The amount of label bound to the first protein is then determined. A change in protein-protein interaction (e.g., binding) between the first protein and the second protein as assessed by the amount of label bound is indicative of the usefulness of the compound in inhibiting protein-protein interactions between the Hsp90 polypeptide, and the FGFR polypeptide, e.g., the FGFR1, FGFR2, FGFR3 or FGFR4 polypeptide, or a fragment thereof. In some embodiments, the change is assessed relative to the same reaction without addition of the test compound.

In certain embodiments, the first protein is attached to a solid support. Solid supports include, e.g., resins such as agarose, beads, and multiwell plates. In certain embodiments, the method includes a washing step after the contacting step, so as to separate bound and unbound label.

In certain embodiments, a plurality of test compounds is contacted with the first protein and the second protein. The different test compounds can be contacted with the other compounds in groups or separately. In certain embodiments, each of the test compounds is contacted with both the first protein and the second protein in separate wells. For example, the method can screen libraries of test compounds, discussed in detail above. Libraries can include, e.g., natural products, organic chemicals, peptides, and/or modified peptides, including, e.g., D-amino acids, unconventional amino acids, and N-substituted amino acids. Typically, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

In certain embodiments, the first protein is an FGFR polypeptide, e.g., an FGFR1, FGFR2, FGFR3 or FGFR4 polypeptide, or a fragment thereof, and the second protein is an Hsp90 polypeptide, or a fragment thereof In other embodiments, the first protein is an Hsp90 polypeptide, or a fragment thereof, and the second protein is an FGFR polypeptide, e.g., an FGFR1, FGFR2, FGFR3 or FGFR4 polypeptide, or a fragment thereof The solid support to which the first protein is attached can be, e.g., SEPHAROSE™ beads, scintillation proximity assay (SPA) beads (microspheres that incorporate a scintillant) or a multiwell plate. SPA beads can be used when the assay is performed without a washing step, e.g., in a scintillation proximity assay. SEPHAROSE™ beads can be used when the assay is performed with a washing step. The second protein can be labeled with any label that will allow its detection, e.g., a radiolabel, a fluorescent agent, biotin, a peptide tag, or an enzyme fragment. The second protein can also be radiolabeled, e.g., with $^{125}$I or $^3$H.

In certain embodiments, the enzymatic activity of an enzyme chemically conjugated to, or expressed as a fusion protein with, the first or second protein, is used to detect bound protein. A binding assay in which a standard immunological method is used to detect bound protein is also included.

In certain other embodiments, the interaction of a first protein and a second protein is detected by fluorescence resonance energy transfer (FRET) between a donor fluorophore covalently linked to a first protein (e.g., a fluorescent group chemically conjugated to a peptide disclosed herein, or a variant of green fluorescent protein (GFP) expressed as a GFP chimeric protein linked to a peptide disclosed herein) and an acceptor fluorophore covalently linked to a second protein, where there is suitable overlap of the donor emission spectrum and the acceptor excitation spectrum to give efficient nonradiative energy transfer when the fluorophores are brought into close proximity through the protein-protein interaction of the first and second protein. Alternatively, both the donor and acceptor fluorophore can be conjugated at each end of the same peptide, e.g., a FGFR3 peptide. The free peptide has high FRET efficiency due to intramolecular FRET between donor and acceptor sites causing quenching of fluorescence intensity. Upon binding to Hsp90, the intramolecular FRET of the peptide-dye conjugate decreases, and the donor signal increases. In another embodiment, fluorescence polarization (FP) is used to monitor the interaction between two proteins. For example, a fluorescently labeled peptide will rotate at a fast rate and exhibit low fluorescence polarization. When bound to a protein, the complex rotates more slowly, and fluorescence polarization increases.

In other embodiments, the protein-protein interaction is detected by reconstituting domains of an enzyme, e.g., beta-galactosidase (see Rossi et al, *Proc. Natl. Acad. Sci. USA*, 94:8405-8410 (1997)).

In still other embodiments, the protein-protein interaction is assessed by fluorescence ratio imaging (Bacskai et al, *Science*, 260:222-226 (1993)) of suitable chimeric constructs of a first and second protein, or by variants of the two-hybrid assay (Fearon et al, *Proc. Nat'l. Acad. Sci USA*, 89:7958-7962 (1992); Takacs et al, *Proc. Natl. Acad. Sci. USA*, 90:10375-10379 (1993); Vidal et al, *Proc. Nat'l. Acad. Sci. USA*, 93:10315-10320 (1996); Vidal et al, *Proc. Nat'l Acad. Sci USA*, 93:10321-10326 (1996)) employing suitable constructs of first and second protein tailored for a high throughput assay to detect compounds that inhibit the first protein/second protein interaction. These embodiments have the advantage that the cell permeability of compounds that act as modulators in the assay is assured.

For example, in one assay, but not the only assay, an FGFR polypeptide, e.g., an FGFR1, FGFR2, FGFR3 or FGFR4 polypeptide, or a fragment thereof is adsorbed to ELISA plates. The adsorbed polypeptides are then exposed to test compounds, followed by exposure to an Hsp90 polypeptide or a fragment thereof (optionally fused to a reporter peptide such as Glutathione S-transferase). ELISA plates are washed and bound protein is detected using anti-Hsp90 antibody (or an antibody that selectively binds the reporter peptide). The antibody can be detected either directly or indirectly using a secondary antibody. Compounds that interfere with protein-protein interactions yield reduced antibody signal in the ELISA plates.

Candidate compounds can be further tested for their ability to destabilize FGFRs and/or decrease FGFR activity or signaling. Candidate compounds are considered to be capable of destabilizing FGFRs if administration of the compound to cells decreases the level of an FGFR protein, e.g., an FGFR1, FGFR2, FGFR3, or FGFR4 protein, in the cells, and/or increases the ubiquitination of an FGFR protein, e.g., an FGFR1, FGFR2, FGFR3, or FGFR4 protein, in the cells, as compared to untreated cells. Level of an FGFR protein in cells can be determined by conventional methods, e.g., immunoblotting. Level of ubiquitinated FGFR protein in cells can also be assayed by methods well known in the art, e.g., immunoblotting. The ability of a candidate compound to decrease FGFR activity or signaling can be determined by conventional methods, for example, assaying for the amount of phosphorylation of proteins involved in FGFR signaling pathways, e.g., Raf-1, MEK1,2, Erk1,2 MEK⅙, Frs2, and p38, or determining expression levels of FGFR signaling molecules, e.g., Snail1. These assays can be performed with cell lines that endogenously express FGFRs, e.g., RT112 bladder cancer cells that express FGFR3, or cultured chondrocytes or other types of cultured cells lacking endogenous FGFRs engineered to express FGFRs, e.g., Cos7 or HEK293 cells expressing recombinant FGFR3. These assays can be performed with cells expressing wildtype or mutant FGFRs.

Candidate compounds can be further tested for their ability to promote chondrocyte proliferation or differentiation in vivo, e.g., in a animal model, or in vitro, e.g., in cultured chondrocytes. A cultured chondrocyte can be derived from a cell line, such as cell line ATDC5 (RIKEN cell bank, Japan). In some embodiments, detecting increased differentiation includes detecting expression of type X collagen. Detecting expression of type X collagen can include, e.g., reverse transcription PCR using collagen type-specific primers, or immunodetection using an antibody specific for collagen type X.

Primary cultures of mammalian chondrocytes useful for the screening assays described herein include costochondral-derived cells (Boyan, et al., 1988, *Bone* 9:185-194). Resting and growth zones are dissected from rib cages of rats (100-150 g) and incubated overnight in DMEM. They are washed in HBSS and then sequentially digested at 37° with 1% trypsin (Sigma) for 1 hour and collagenase (Worthington, Type II) at 0.02% for 3 hours. Cells are then separated from debris by filtration through 40-mesh nylon, pelleted for 5 minutes at 500 rcf, resuspended in DMEM. Cell viability is assessed by dye exclusion, and the cells are plated in DMEM supplemented with 10% fetal bovine serum, 50 mg/ml ascorbate, and antibiotics. Cells are plated at 10,000 to 25,000 per $cm^2$ in multi-well culture dishes and incubated in a humidified, 5% $CO_2$ atmosphere at 37°. Alternatively, xyphoid cartilage from adult rats may be a suitable source tissue for primary cultures. See Rani, 1999, *Dev. Dyn.* 214:26-33. Cultures are maintained for a maximum of 3 passages. Although the foregoing is a description of primary chondrocyte cultures from rat source tissues, these techniques can be adapted readily for primary culture of chondrocytes from suitable tissue of other mammals, e.g., mice, rabbits and humans.

The presence of col II and col X mRNA in Northern blots or RT-PCR of RNA extracts (Trizol, Life Technologies) can be used to monitor chondrocyte phenotype. Total protein extracts can be made from some cultures by homogenizing in 8M urea containing 2% b-mercaptoethanol and 2% Non-Idet P40, as described in Odgren, 1996, *J. Cell Sci.* 109:2253-2264.

Compounds that alter chondrocyte proliferation or differentiation in an initial screen can be considered candidate compounds, e.g., candidate Hsp90-inhibiting compounds. Candidate compounds can be retested, e.g. on chondrocytes, e.g., in vitro, or tested on animals, e.g., animals that are models for abnormal (excessive or insufficient) cartilage or skeletal growth. Candidate compounds that are positive in a retest can be considered "lead" compounds to be further optimized and derivatized, or may be useful therapeutic or diagnostic compounds themselves.

Medicinal Chemistry

Once a compound (or agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al., *J. Antibiot.* 41:1430-8 (1988). Furthermore, if the biochemical target of the compound (or agent) is known or determined, the structure of the target and the compound can inform the design and optimization of derivatives. Molecular modeling software is commercially available (e.g., Molecular Simulations, Inc.) for this purpose.

III. Kits for Screening for Hsp90 Inhibitors

Provided herein are kits for identifying compounds that disrupt the ability of Hsp90 to stabilize an FGFR, e.g., FGFR1, FGFR2, FGFR3 or FGFR4, e.g., by inhibiting the formation of FGFR/Hsp90 complexes (e.g., inhibiting binding of an FGFR and Hsp90) using, for example, the screening assays described herein. The kit can include, for example, FGFR polypeptides or fragments thereof as described above, and Hsp90 polypeptides or fragments thereof as described above. The kit can further comprise instructions for using the kit to identify compounds that inhibit protein-protein interactions between the FGFR and Hsp90 polypeptides, e.g., instructions for how to perform the screening assays described above.

Kits

FGFR polypeptides, e.g., FGFR1, FGFR2, FGFR3 or FGFR4 polypeptides, or a combination thereof, can be provided in a kit. The kit can also provide Hsp90 polypeptides. A kit can include (a) an FGFR polypeptide or an Hsp90-binding fragment thereof, (b) an Hsp90 polypeptide or FGFR-binding fragment thereof, and optionally (c) informational material. For example, the kit can include an FGFR3 polypeptide or an Hsp90-binding fragment thereof. The kit can include one or more compositions each having a different FGFR polypeptide or an Hsp90-binding fragment thereof, e.g., an FGFR1, FGFR2, FGFR3, or FGFR4 polypeptide. The informational material can be descriptive, instructional, marketing or other material that relates to the screening methods described herein and/or the use of FGFR polypeptides and Hsp90 polypeptides for the screening methods described herein.

The informational material of the kit is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about FGFR and Hsp90 and/or their use in the screening methods described herein. Of course, the informational material can also be provided in any combination of formats.

In addition to FGFR polypeptides and Hsp90 polypeptides, the kit can include other ingredients, such as a solvent or buffer, and/or other agents for practicing the screening methods described herein. In such embodiments, the kit can include instructions for using FGFR polypeptides and Hsp90 polypeptides together with the other ingredients.

FGFR polypeptides and Hsp90 polypeptides can be provided in any form, e.g., liquid, dried or lyophilized form. These can be provided in, e.g., substantially pure and/or sterile form. When FGFR polypeptides and Hsp90 polypeptides are provided in a liquid solution, the liquid solution can be an aqueous solution, e.g., a sterile aqueous solution.

The kit can include one or more containers for the composition containing an FGFR polypeptide or an Hsp90 polypeptide. The kit can include separate containers, dividers or compartments for the composition and informational material. For example, the composition can be contained in a bottle, vial, or syringe, and the informational material can be contained in a plastic sleeve or packet. The separate elements of the kit can be contained within a single, undivided container. For example, the composition can be contained in a bottle, vial or syringe that has attached thereto the informational material in the form of a label. The kit may include a plurality (e.g., a pack) of individual containers, each containing one composition including an FGFR polypeptide or an Hsp90 polypeptide. For example, the kit can include a plurality of syringes, ampoules, foil packets, or blister packs, each containing a composition including an FGFR polypeptide. The containers of the kits can be air tight and/or waterproof.

IV. Transgenic Animals and Animal Models

Animal models, such as mouse models, can be useful tools for practicing the methods described herein. A number of mouse models for FGFR related disorders have been generated. For example, mice homozygous and heterozygous for a lys644-to-glu (K644E) point mutation in the FGFR3 gene (corresponding to the lys650-to-glu mutation (K650E) found in TD2 patients) have been generated (Li et al., *Hum. Molec. Genet.* 8: 35-44, 1999). Homozygosity for this mutant allele produces a severe phenotype similar to TD in humans, while heterozygosity for the mutant allele results in a moderately severe phenotype similar to human achondroplasia. Mouse models for other mutations in the different FGFRs have also been generated (see, e.g., Chen et al., *Hum. Molec. Genet.* 10: 457-465 (2001); Iwata et al., *Hum. Molec. Genet.* 10: 1255-1264 (2001); Colvin et al., *Nature Genet.* 12: 390-397 (1996); Eswarakumar and Schlessinger, *Proc. Nat. Acad. Sci.* 104: 3937-3942 (2007); Zhou et al., *Hum. Mol Genet.*, 9: 2001-2009 (2000)). Transgenic mice having FGFR mutations can also be generated by methods known in the art.

Mice with reporter genes can also be useful for practicing the methods described herein. For example, mice expressing wild-type or mutant FGFRs fused to fluorescent proteins, e.g., mice having a FGFR reporter gene, can be generated by methods known in the art and used to study expression levels and patterns of FGFRs in vivo.

Transgenic animals can be, for example, farm animals (pigs, goats, sheep, cows, horses, rabbits, chickens and the like) rodents (such as rats, guinea pigs, and mice), non-human primates (for example, baboons, monkeys, and chimpanzees), and domestic animals (for example, dogs and cats).

Any technique known in the art can be used to introduce a transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983). Especially useful are the methods described in Yang et al. (*Proc. Natl Acac. Sci. USA* 94:3004-3009, 1997).

Mosaic animals can also be generated, e.g., animals that carry the transgene in some, but not all of their cells. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

Gene targeting is useful when it is desired that a transgene be integrated into the chromosomal site of an endogenous gene. Briefly, when such a technique is to be used, vectors containing some nucleotide sequences homologous to an endogenous gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous gene in only that cell type (Gu et al., *Science* 265:103, 1984). The regulatory sequences required for such a cell-type specific inactivation will depend upon the particular cell type of interest, and will be apparent to those of skill in the art.

Once transgenic animals have been generated, the expression of the recombinant gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of transgene gene-expressing tissue can also be evaluated immunocytochemically using antibodies specific for the reporter gene product.

For a review of techniques that can be used to generate and assess transgenic animals, skilled artisans can consult Gordon (*Intl. Rev. Cytol.* 115:171-229, 1989), and may obtain additional guidance from, for example: Hogan et al. *Manipulating the Mouse Embryo*, Cold Spring Harbor Press, Cold Spring Harbor, N.Y., 1986); Krimpenfort et al. (*Bio/Technology* 9:86, 1991), Palmiter et al. (*Cell* 41:343, 1985), Kraemer et al. (*Genetic Manipulation of the Early Mammalian Embryo*, Cold Spring Harbor Press, Cold Spring Harbor, N.Y., 1985), Hammer et al. (*Nature* 315:680, 1985), Purcel et al. (*Science*, 244:1281, 1986), Wagner et al. (U.S. Pat. No. 5,175,385), and Krimpenfort et al. (U.S. Pat. No. 5,175,384).

EXAMPLES

The invention is illustrated in part by the following examples, which are not to be taken as limiting the invention in any way.

Example 1

FGFR3 is a Client Protein of Hsp90

In this example, FGFR3 was shown to be a client protein of Hsp90. The data strongly suggest that Hsp90 is important for FGFR3 protein stability, and that mutant FGFR3s may be more dependent on it for stability, sensitizing them to Hsp90 inhibition. Wildtype (WT) and mutant mouse FGFR3 genes were used in the example.

Figure 7:
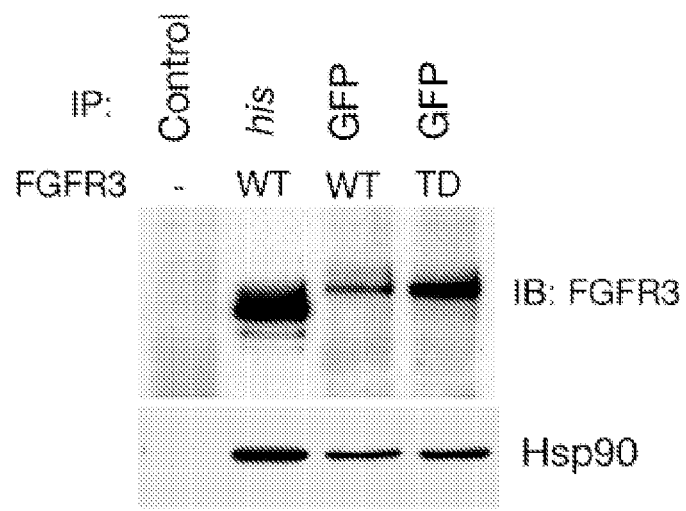
FIG. 7 is a picture of immunoblot showing that V5-his or GFP tagged WT FGFR3 co-immunoprecipitates with Hsp90. Note that V5-his tag is smaller than GFP, but immunoprecipitation is more efficient.

It was demonstrated that Hsp90 and FGFR3 proteins form a complex in cells. GFP or V5-his tagged FGFR3 proteins were immunoprecipitated from Cos7 cells expressing these proteins, and Western blotting was performed to determine whether Hsp90 co-immunoprecipitated with FGFR3. As shown in FIG. 7, Hsp90 co-immunoprecipitated with FGFR3. N-terminal sequencing of a gel purified 90 kDa band that co-immunoprecipitated with FGFR3 confirmed that the band corresponded to Hsp90 β, the constitutively expressed, cytoplasmic isoform of Hsp90 implicated in mutant kinase stabilization.

Figure 8:
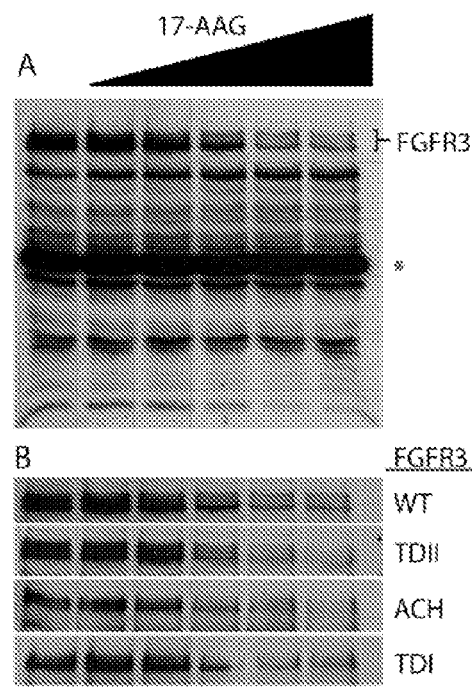
FIGS. 8A and 8B are pictures of immunoblots illustrating 17-AAG dose-dependent reduction in the levels of wildtype (WT.
Figure 9:
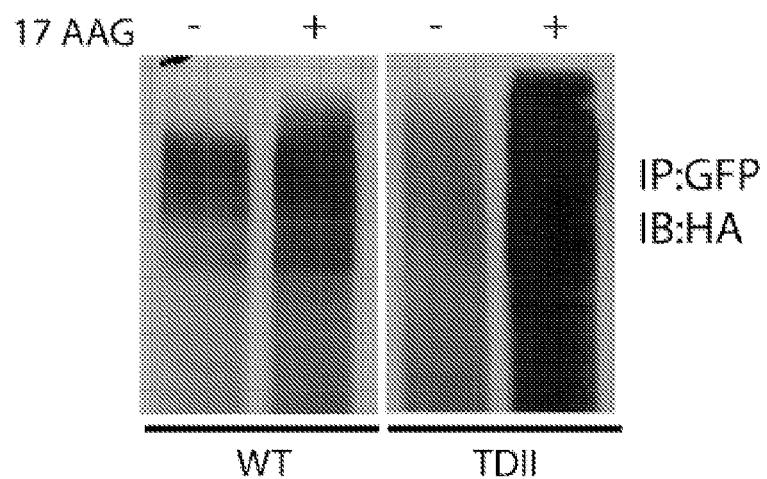
FIG. 9 is a picture of immunoblot showing that 17-AAG induces ubiquitination of WT FGFR3 and TDII FGFR3 proteins.
Figure 10:
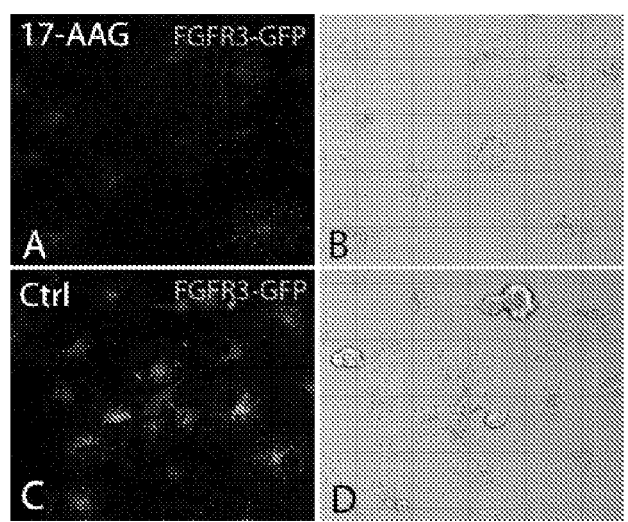
FIG. 10A-10D are confocal microscopy images showing cells expressing TDII FGFR3-GFP treated for 3 hr with 17-AAG (FIGS. 10A and 10B) or not treated with 17-AAG (FIGS. 10C and 10D). B,D-transmitted light images of A,C, respectively.
Figure 11:
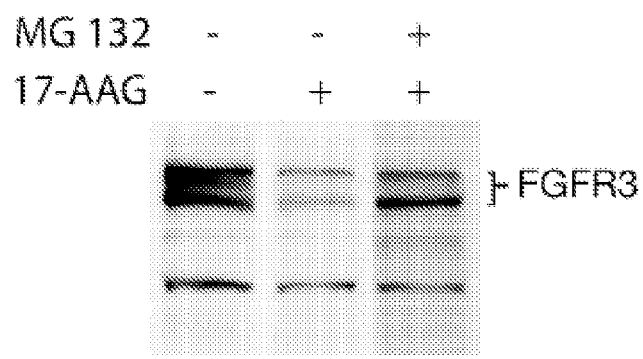
FIG. 11 is a picture of immunoblot demonstrating that 17-AAG-induced decrease in TDII FGFR3 protein level is partially rescued by the proteasome inhibitor MG132. The two FGFR3 bands reflect glycosylation differences.

It was further shown that Hsp90 inhibition increased FGFR3 ubiquitination and reduced FGFR3 protein level in cells, most likely via proteasome degradation. Cos7 cells stably expressing WT FGFR3, FGFR3 with a TDII mutation (TDII FGFR3) and also FGFR3 with a TDI mutation (TDI FGFR3), and FGFR3 with an ACH mutation (ACH FGFR3) were treated with increasing doses of 17-AAG and lysed in sample buffer. Levels of these FGFR3 proteins were determined by Western blotting. FIGS. 8A and 8B document a dose-dependent reduction in the levels of all four FGFR3 proteins and suggest that mutant FGFR3 may be more sensitive to Hsp90 inhibition than WT FGFR3. Notable was that although many background bands could be visualized on lysate blots, only FGFR3 bands decreased indicating that the result was not a non-specific effect of 17-AAG on protein synthesis or saturation of proteasomal degradation as confirmed by actin blotting (FIG. 8A). Further, cells expressing WT FGFR3-GFP or TDII FGFR3-GFP, and HA:ubiquitin were treated with 17-AAG, and FGFR3-GFP was immunoprecipitated from cell lysates and blotted for HA-ubiquitin. As shown in FIG. 9, 17-AAG treatment increased FGFR3 ubiquitination. Of note, baseline ubiquitination of TDII FGFR3 was less than WT FGFR3. However, the mutant receptor is ubiquitinated more than WT FGFR3 in response to 17-AAG. That Hsp90 inhibition induces FGFR3 degradation was also confirmed by confocal microscopy. Three-hour treatment with 17-AAG reduced cellular GFP signal in cells expressing TDII FGFR3-GFP (FIGS. 10A-D; B and D—transmitted light images of A and C). These results predict that proteasome inhibition would reduce FGFR3 protein degradation. This was confirmed by treating cells expressing TDII FGFR3 with MG132 (a proteasome inhibitor), which decreased TDII FGFR3 degradation (FIG. 11).

Figure 12:
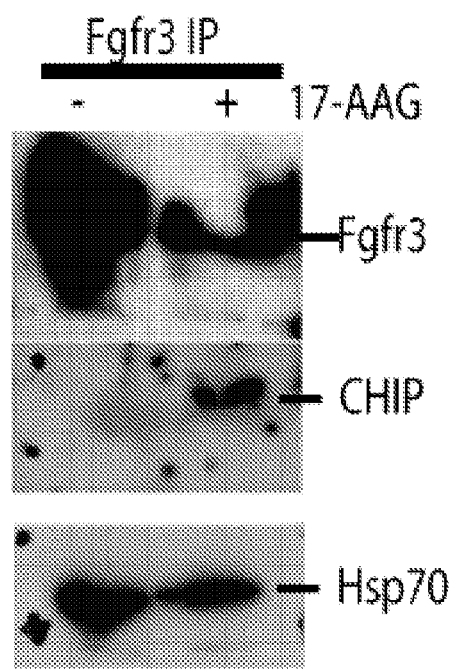
FIG. 12 is a picture of immunoblot illustrating that that CHIP is recruited to the a FGFR3:Hsp90 complex by 17-AAG treatment.
Figure 13:
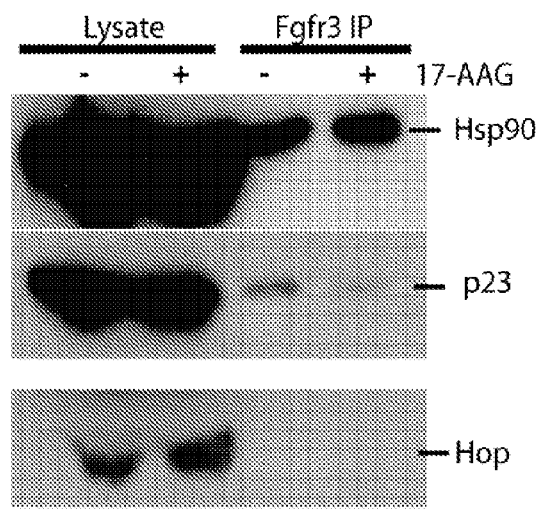
FIG. 13 is a picture of immunoblot illustrating that that p23 is displaced from a FGFR3:Hsp90 complex by 17-AAG treatment.

Hsp90 interacts with its client proteins in a cyclical fashion, which is driven by multiple rounds of ATP hydrolysis (Young et al., *J Cell Biol.*, 154:267-273 (2001)). The chaperone machinery that allows cycling of Hsp90 on its client proteins consists of several cofactors and accessory proteins including Hsp70, CHIP (E-3 ubiquitin ligase), Hsp40, HOP (Hsp90/Hsp70 organizing protein), p23 and immuonophilins. When ATP hydrolysis is disturbed, the protective effect of Hsp90 is lost and client proteins are ubiquitinated by CHIP and targeted to proteasomes for degradation. p23 appears to be required for cycling of ATP and its displacement is associated with loss of Hsp90's ability to stabilize client proteins. It was demonstrated here that p23 is displaced from and CHIP recruited to the FGFR3:Hsp90 complex by 17-AAG treatment (FIGS. 12 and 13). These results further confirm that 17-AAG or other Hsp90 inhibitors destabilize FGFR3 protein leading to its degradation.

Figure 14:
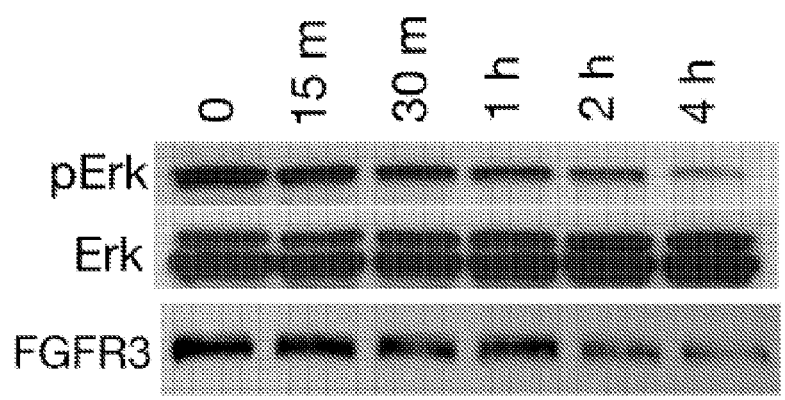
FIG. 14 is a picture of immunoblot showing that 17-AAG dependent reduction in pERK (phosphorylated Erk) level coincides with decreased TDII FGFR3 protein level in cells expressing TDII FGFR3.

Additionally, it was demonstrated that 17-AAG reduces FGFR3 signaling in cells. In a time-dependent experiment, Cos7 cells expressing TDII FGFR3 were treated with 17-AAG and the levels of TDII FGFR3, Erk and phosphorylateed Erk (perk) proteins were determined. As shown in FIG. 13, 17-AAG treatment led to a reduction in pErk and TDII FGFR3 protein levels, indicating a decrease in mutant FGFR3 signaling through the MAPK pathway (FIG. 14).

It expected that endogenous FGFR3 protein, e.g., expressed endogenously in cells, is a client protein of Hsp90 and that Hsp90 inhibitors destabilize endogenous FGFR3 protein.

Example 2

Effects of Treating fgfr3 Mutant Mice with Hsp90 Inhibitors

In this example, mice were treated with an Hsp90 inhibitor and the effect on skeletal growth was investigated.

Mice having a lys644-to-glu (K644E) point mutation in the FGFR3 gene, which corresponds to the lys650-to-glu mutation (K650E) found in TD2 patients (Li et al., *Hum. Molec. Genet.* 8: 35-44, 1999), were used in this example. This mouse is useful because homozygosity for the mutant allele produces a severe phenotype similar to TD in humans, while heterozygosity for the mutant Fgfr3 allele results in a moderately severe phenotype similar to human achondroplasia.

Heterozygote parent mice were mated to produce litters containing a mixture of homozygous wild type (WT), heterozygous mutant (HET) and homozygous mutant (HMZ) mice in each litter. Each entire litter was injected intraperitoneally with either 17-AAG at 25 mg/kg (mouse weight) dissolved in DMSO (Rx) or DMSO alone (control). The dose of 17-AAG used here has been shown to promote degradation of mutant androgen receptor in a mouse model of a neurodegenerative disease (Wasa et al, *Nat Med*, 11: 1088-95 (2005)). Since each litter should contain all three genotypes (WT, HET and HMZ) at least in theory, comparisons could be made between mice within each litter, and between treated and control litters. The WT, HET and HMZ mouse pups were injected three times a week from 2 to 8 weeks of age with periodic measurements and skeletal X-rays at weeks 4, 6 and 8. The X-rays were scanned and femoral lengths measured in triplicate using ImageJ software and results analyzed according to genotype, sex and age using Excel.

Femoral length was used because the proximal limb bones typically exhibit the greatest growth deficiency in human achondroplasia and also because the femurs have landmarks that can consistently be detected on the X-rays (i.e., measurements do not precisely correspond to femoral lengths, but rather to distance between X-ray landmarks that approximated bone lengths).

Figure 15:
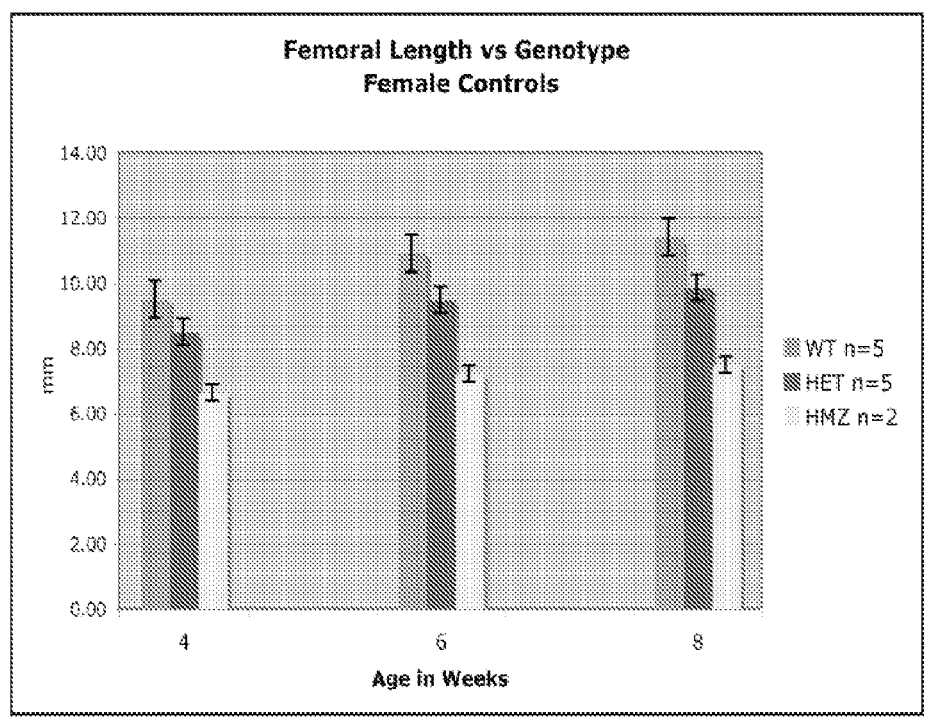
FIG. 15 is a graph showing femoral length in homozygous wild type (WT), heterozygous FGFR3 mutant (HET) and homozygous FGFR3 mutant (HMZ) female mice. Measurements were made on scanned skeletal X-rays.

Several of the pups died—mostly homozygotes for the mutation. However, there were sufficient mice to make a limited number of important comparisons. First, femoral length of females with the three genotypes (homozygous wild type, heterozygous and homozygous mutant) were compared, validating that determining femoral length is adequate to distinguish the genotypes from one another. As shown in FIG. 15, the difference between genotypes increases as the mice grow as would be expected. Femoral lengths between treated and control heterozygous mice of both sexes were also compared (FIGS. 16 and 17). Each figure contains a graph without error bars (FIG. 16A and 17A) and the same graph with error bars (FIGS. 16B and 17B). As shown in these figures, treated mice appear to have increasingly longer femurs over time than untreated mice for both sexes. Although adding error bars suggests that the difference may not be statistically significant, these results nevertheless indicate that Hsp90 inhibitors can potentially be used to treat skeletal disorders such as achondroplasia or to promote bone growth.

What is claimed is:

1. A method of treating achondroplasia in a patient, comprising
    identifying a patient having achondroplasia; and
    administering to the patient an amount of a Heat Shock Protein-90 (Hsp90) inhibitor selected from the group consisting of geldanamycin, 17-allylamino-17-demethoxygeldanamycin (17-AAG), 17-(2-dimethylaminoethyl)amino-17-demethoxygeldanamycin (17-DMAG), tanespimycin, retaspimycin, IPI-493, CNF-1010, alvespimycin, BIIB021, SNX-5422, and STAT-9090 effective to treat achondroplasia in the patient.

2. The method of claim 1, wherein the Hsp90 inhibitor is geldanamycin.

3. The method of claim 1, wherein the patient is a human patient.

4. A method of promoting bone growth in a patient with achondroplasia, comprising:
    administering to the patient an amount of a Heat Shock Protein-90 (Hsp90) inhibitor selected from the group consisting of geldanamycin, 17-allylamino-17-demethoxygeldanamycin (17-AAG), 17-(2-dimethylaminoethyl)amino-17-demethoxygeldanamycin (17-DMAG), tanespimycin, retaspimycin, IPI-493, CNF-1010, alvespimycin, BIIB021, SNX-5422, and STAT-9090 effective to promote bone growth in the patient; and
    monitoring the patient for increased bone growth.

5. The method of claim 4, wherein the patient is a human patient.

6. The method of claim 4, wherein the Hsp90 inhibitor is geldanamycin.

7. The method of claim 1, wherein the Hsp90 inhibitor is 17-allylamino-17-demethoxygeldanamycin (17-AAG).

8. The method of claim 1, wherein the Hsp90 inhibitor is 1742-dimethylaminoethyl)amino-17-demethoxygeldanamycin (17-DMAG).

9. The method of claim 1, wherein the Hsp90 inhibitor is tanespimycin.

10. The method of claim 1, wherein the Hsp90 inhibitor is retaspimycin.

11. The method of claim 1, wherein the Hsp90 inhibitor is IPI-493.

12. The method of claim 1, wherein the Hsp90 inhibitor is CNF-1010.

13. The method of claim 1, wherein the Hsp90 inhibitor is alvespimycin.

14. The method of claim 1, wherein the Hsp90 inhibitor is BIIB021.

15. The method of claim 1, wherein the Hsp90 inhibitor is, SNX-5422.

16. The method of claim 1, wherein the Hsp90 inhibitor is STAT-9090.

17. The method of claim 4, wherein the Hsp90 inhibitor is 17-allylamino-17-demethoxygeldanamycin (17-AAG).

18. The method of claim 4, wherein the Hsp90 inhibitor is 17-(2-dimethylaminoethyl)amino-17-demethoxygeldanamycin (17-DMAG).

19. The method of claim 4, wherein the Hsp90 inhibitor is tanespimycin.

20. The method of claim 4, wherein the Hsp90 inhibitor is retaspimycin.

21. The method of claim 4, wherein the Hsp90 inhibitor is IPI-493.

22. The method of claim 4, wherein the Hsp90 inhibitor is CNF-1010.

23. The method of claim 4, wherein the Hsp90 inhibitor is alvespimycin.

24. The method of claim 4, wherein the Hsp90 inhibitor is BIIB021.

25. The method of claim 4, wherein the Hsp90 inhibitor is, SNX-5422.

26. The method of claim 4, wherein the Hsp90 inhibitor is STAT 9090 STAT-9090.

* * * * *

UNITED STATES PATENT AND TRADEMARK OFFICE
CERTIFICATE OF CORRECTION

PATENT NO. : 8,426,396 B2  
APPLICATION NO. : 12/350940  
DATED : April 23, 2013  
INVENTOR(S) : William A. Horton and Melanie B. Laederich Page 1 of 1

It is certified that error appears in the above-identified patent and that said Letters Patent is hereby corrected as shown below:

In the Claims:

Col. 69, line 59, in Claim 8, delete "1742-" and insert -- 17-(2- --, therefor.

Col. 70, line 35, in Claim 15, delete "is," and insert -- is --, therefor.

Col. 70, line 56, in Claim 25, delete "is," and insert -- is --, therefor.

Col. 70, line 59, in Claim 26, delete "STAT 9090 STAT-9090." and insert -- STAT-9090. --, therefor.

Signed and Sealed this  
Ninth Day of July, 2013

Teresa Stanek Rea  
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,426,396 B2 | Page 1 of 1 |
| APPLICATION NO. | : 12/350940 | |
| DATED | : April 23, 2013 | |
| INVENTOR(S) | : Horton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 581 days.

Signed and Sealed this
Thirtieth Day of December, 2014

Michelle K. Lee
*Deputy Director of the United States Patent and Trademark Office*